(12) United States Patent
Gladwin et al.

(10) Patent No.: US 8,927,030 B2
(45) Date of Patent: Jan. 6, 2015

(54) USE OF NITRITE SALTS FOR THE TREATMENT OF CARDIOVASCULAR CONDITIONS

(75) Inventors: Mark T. Gladwin, Pittsburgh, PA (US); Alan N. Schechter, Bethesda, MD (US); David J. Lefer, Atlanta, GA (US); Rakesh P. Patel, Hoover, AL (US); Christian J. Hunter, Boston, MA (US); Gordon G. Power, Redlands, CA (US); Daniel B. Kim-Shapiro, Winston-Salem, NC (US); Ryszard Marek Pluta, Bethesda, MD (US); Edward H. Oldfield, Philomont, VA (US); Richard O. Cannon, III, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 857 days.

(21) Appl. No.: 12/748,184

(22) Filed: Mar. 26, 2010

(65) Prior Publication Data
US 2010/0247682 A1    Sep. 30, 2010

Related U.S. Application Data

(63) Continuation of application No. 10/563,683, filed as application No. PCT/US2004/022232 on Jul. 9, 2004, application No. 12/748,184, which is a continuation of application No. 10/563,682, filed as application No. PCT/US2004/021985 on Jul. 9, 2004, now abandoned.

(60) Provisional application No. 60/485,959, filed on Jul. 9, 2003, provisional application No. 60/511,244, filed on Oct. 14, 2003.

(51) Int. Cl.
| A01N 59/00 | (2006.01) |
| A61K 33/00 | (2006.01) |
| A01N 37/12 | (2006.01) |
| A01N 37/44 | (2006.01) |
| A61K 45/06 | (2006.01) |

(52) U.S. Cl.
CPC ............. *A61K 45/06* (2013.01); *A61K 33/00* (2013.01)
USPC ................................ 424/718; 514/565

(58) Field of Classification Search
None
See application file for complete search history.

(56) References Cited

U.S. PATENT DOCUMENTS

| 3,865,942 A | 2/1975 | Wirth |
| 4,163,790 A | 8/1979 | Franko et al. |
| 4,211,782 A | 7/1980 | Vane et al. |
| 4,650,484 A * | 3/1987 | Shaw et al. ................. 424/448 |
| 4,849,226 A | 7/1989 | Gale |
| 5,108,754 A | 4/1992 | Wilburn |
| 5,177,208 A | 1/1993 | Wilburn |
| 5,263,473 A | 11/1993 | McWhorter |
| 5,366,997 A | 11/1994 | Keefer et al. |
| 5,385,940 A | 1/1995 | Moskowitz |
| 5,389,675 A | 2/1995 | Christodoulou et al. |
| 5,396,882 A | 3/1995 | Zapol |
| 5,427,797 A | 6/1995 | Frostell et al. |
| 5,485,827 A | 1/1996 | Zapol et al. |
| 5,500,230 A | 3/1996 | Nathanson |
| 5,525,357 A | 6/1996 | Keefer et al. |
| 5,536,241 A | 7/1996 | Zapol |
| 5,570,683 A | 11/1996 | Zapol |
| 5,648,101 A * | 7/1997 | Tawashi ...................... 424/718 |
| 5,650,442 A | 7/1997 | Mitchell et al. |
| 5,683,668 A | 11/1997 | Hrabie et al. |
| 5,770,645 A | 6/1998 | Stamler et al. |
| 5,789,447 A | 8/1998 | Wink, Jr. et al. |
| 5,814,666 A | 9/1998 | Green et al. |
| 5,814,667 A | 9/1998 | Mitchell et al. |
| 5,823,180 A | 10/1998 | Zapol |
| 5,837,736 A | 11/1998 | Mitchell et al. |
| 5,839,433 A | 11/1998 | Higenbottam |
| 5,840,759 A | 11/1998 | Mitchell et al. |
| 5,873,359 A | 2/1999 | Zapol et al. |
| 5,885,621 A | 3/1999 | Head et al. |

(Continued)

FOREIGN PATENT DOCUMENTS

| EP | 1 092 719 | 5/2003 |
| EP | 1336602 | 8/2003 |

(Continued)

OTHER PUBLICATIONS

Thomas et al. Safety of intrathecal sodium nitroprusside for the treatment and prevention of refractory cerebral vasospasm and ischemia in humans. Stroke, 1999, 30: 1409-1416.*

(Continued)

*Primary Examiner* — Anna Pagonakis
(74) *Attorney, Agent, or Firm* — Klarquist Sparkman, LLP

(57) ABSTRACT

It has been surprisingly discovered that administration of nitrite to subjects causes a reduction in blood pressure and an increase in blood flow to tissues. The effect is particularly beneficial, for example, to tissues in regions of low oxygen tension. This discovery provides useful treatments to regulate a subject's blood pressure and blood flow, for example, by the administration of nitrite salts. Provided herein are methods of administering a pharmaceutically-acceptable nitrite salt to a subject, for treating, preventing or ameliorating a condition selected from: (a) ischemia-reperfusion injury (e.g., hepatic or cardiac or brain ischemia-reperfusion injury); (b) pulmonary hypertension (e.g., neonatal pulmonary hypertension); or (c) cerebral artery vasospasm.

17 Claims, 15 Drawing Sheets

(56) References Cited

U.S. PATENT DOCUMENTS

| | | | |
|---|---|---|---|
| 5,904,938 A | 5/1999 | Zapol et al. | |
| 5,912,019 A | 6/1999 | Singh | |
| 5,958,427 A | 9/1999 | Salzman et al. | |
| 5,968,911 A | 10/1999 | Lawson et al. | |
| 5,994,444 A | 11/1999 | Trescony et al. | |
| 6,057,367 A | 5/2000 | Stamler et al. | |
| 6,063,407 A | 5/2000 | Zapol et al. | |
| 6,087,479 A | 7/2000 | Stamler et al. | |
| 6,103,275 A | 8/2000 | Seitz et al. | |
| 6,187,332 B1 | 2/2001 | Gern et al. | |
| 6,187,744 B1 | 2/2001 | Rooney | |
| 6,197,745 B1 | 3/2001 | Stamler | |
| 6,197,762 B1 | 3/2001 | Garvey et al. | |
| 6,258,032 B1 * | 7/2001 | Hammesfahr | 600/454 |
| 6,277,891 B1 | 8/2001 | Sanders et al. | |
| 6,291,424 B1 | 9/2001 | Stamler et al. | |
| 6,314,956 B1 | 11/2001 | Stamler et al. | |
| 6,358,536 B1 | 3/2002 | Thomas | |
| 6,391,895 B1 | 5/2002 | Towart et al. | |
| 6,471,978 B1 | 10/2002 | Stamler et al. | |
| 6,472,390 B1 | 10/2002 | Stamler et al. | |
| 6,476,037 B1 | 11/2002 | Wallace | |
| 6,583,113 B2 | 6/2003 | Stamler et al. | |
| 6,601,580 B1 | 8/2003 | Bloch et al. | |
| 6,627,738 B2 | 9/2003 | Stamler et al. | |
| 6,642,438 B1 | 11/2003 | Clendennen et al. | |
| 6,656,452 B1 | 12/2003 | Zapol et al. | |
| 6,709,681 B2 | 3/2004 | Benjamin et al. | |
| 6,723,703 B2 | 4/2004 | Gaston et al. | |
| 6,796,966 B2 | 9/2004 | Thomas | |
| 6,811,768 B2 | 11/2004 | Zapol et al. | |
| 6,884,773 B1 | 4/2005 | Stamler et al. | |
| 6,935,334 B2 | 8/2005 | Bloch et al. | |
| 6,945,247 B1 | 9/2005 | Stamler et al. | |
| 7,025,869 B2 | 4/2006 | Fine et al. | |
| 7,033,999 B2 | 4/2006 | Stamler et al. | |
| 7,040,313 B2 | 5/2006 | Fine et al. | |
| 7,048,951 B1 | 5/2006 | Seitz et al. | |
| 7,202,340 B2 | 4/2007 | Stamler et al. | |
| 7,335,181 B2 | 2/2008 | Miller et al. | |
| 2001/0034323 A1 | 10/2001 | Rooney | |
| 2002/0037839 A1 | 3/2002 | Stamler et al. | |
| 2002/0090401 A1 | 7/2002 | Tucker et al. | |
| 2002/0095108 A1 | 7/2002 | Tsuchida et al. | |
| 2002/0151255 A1 | 10/2002 | Banerjee et al. | |
| 2002/0155174 A1 | 10/2002 | Benjamin et al. | |
| 2003/0022267 A1 | 1/2003 | Stamler et al. | |
| 2003/0032917 A1 | 2/2003 | Stamler | |
| 2003/0203915 A1 | 10/2003 | Fang et al. | |
| 2004/0037897 A1 | 2/2004 | Benjamin et al. | |
| 2004/0105898 A1 | 6/2004 | Benjamin et al. | |
| 2005/0036949 A1 | 2/2005 | Tucker et al. | |
| 2005/0037093 A1 | 2/2005 | Benjamin | |
| 2005/0069595 A1 | 3/2005 | Chen et al. | |
| 2005/0131064 A1 | 6/2005 | Gaston et al. | |
| 2005/0142218 A1 | 6/2005 | Tucker et al. | |
| 2005/0227912 A1 | 10/2005 | Fronticelli et al. | |
| 2006/0088583 A1 | 4/2006 | Takeoka et al. | |
| 2006/0147553 A1 | 7/2006 | Miller et al. | |
| 2006/0182815 A1 | 8/2006 | Gladwin et al. | |
| 2006/0252671 A1 | 11/2006 | Stamler et al. | |
| 2007/0086954 A1 | 4/2007 | Miller | |
| 2007/0144515 A1 | 6/2007 | Stenzler et al. | |
| 2007/0154569 A1 | 7/2007 | Gladwin et al. | |
| 2007/0167352 A1 | 7/2007 | Winslow et al. | |
| 2007/0190184 A1 | 8/2007 | Montgomery et al. | |
| 2010/0203172 A1 | 8/2010 | Sherman et al. | |

FOREIGN PATENT DOCUMENTS

| | | |
|---|---|---|
| JP | 7-53358 | 2/1995 |
| JP | 9-512523 | 12/1997 |
| JP | 2001-151778 | 6/2001 |
| WO | WO94/00180 | 1/1994 |
| WO | WO94/22499 | 10/1994 |
| WO | WO95/12394 | 5/1995 |
| WO | WO95/22335 | 8/1995 |
| WO | WO 95/26768 | 10/1995 |
| WO | WO 96/25184 | 8/1996 |
| WO | WO96/30006 | 10/1996 |
| WO | WO97/10265 | 3/1997 |
| WO | WO99/02148 | 1/1999 |
| WO | WO 99/20251 | 4/1999 |
| WO | WO99/38472 | 8/1999 |
| WO | WO99/44622 | 9/1999 |
| WO | WO00/30659 | 6/2000 |
| WO | WO00/53193 | 9/2000 |
| WO | WO01/10406 | 2/2001 |
| WO | WO01/26547 | 4/2001 |
| WO | WO01/43805 | 6/2001 |
| WO | WO01/80890 | 11/2001 |
| WO | WO01/89572 | 11/2001 |
| WO | WO01/89617 | 11/2001 |
| WO | WO02/17881 | 3/2002 |
| WO | WO02/17898 | 3/2002 |
| WO | WO02/20026 | 3/2002 |
| WO | WO 02/056904 | 7/2002 |
| WO | WO03/013489 | 2/2003 |
| WO | WO03/032928 | 4/2003 |
| WO | WO03/102575 | 12/2003 |
| WO | WO2004/054433 | 7/2004 |
| WO | WO2005/004884 | 1/2005 |
| WO | WO2005/007173 | 1/2005 |
| WO | WO2006/096774 | 9/2006 |
| WO | WO2006/113540 | 10/2006 |
| WO | WO 2008/060785 | 5/2008 |

OTHER PUBLICATIONS

White et al. Evidence of a possible role for nitric oxide in the modulation of heart activity in *Achatina fulica* and *Helix aspersa*. Comparative Biochemistry and Physiology Part C 137, 2004, 95-108.*

Dalloz et al. In vitro studies of interactions of NO donor drugs with superoxide and hydroxyl radicals. Molecular and Cellular Biochemistry, 177: 193-200, 1997.*

Imai, "Mechanism of Vasodilator Action of So-Called Nitrite Compounds," *J Clin Exp Med.*, vol. 148(2):71-74, 1989.

Matsui et al., "Therapeutic Methods for Cerebral Vasospasm," *Brain and Circulation*, vol. 6(1):69-75, 2001.

Moulds et al., "A Comparison of the Effects of Hydrallazine, Diazoxide, Sodium Nitrite and Sodium Nitroprusside on Human Isolated Arteries and Veins," Br. J. Clin. Pharmac., vol. 1:57-61, 1981.

Nakazawa, "Ischemia-Reperfusion Disorder and NO," *Clinician*, No. 456:76-80, 1996.

Seifter et al., "Effect of Vasoactive Drugs on the Residual Content of Blood in the Brain of Chicks," *Euro. J. Pharmac.*, vol. 11:29-32, 1970.

Tobise, "Pulmonary Hypertension: Recent Progress," *IRYO*, vol. 55(5):212-218, 2001.

Abman et al., "Inhaled ethyl nitrite gas for persistent pulmonary hypertension in infants," *Lancet*, 360:2076-2077 (2002) (Including Author's Reply).

Ali et al. "A Method to Attenuate Pneumoperitoneum-Induced Reductions in Splanchnic Blood Flow," *Annals of Surgery* 241 (2): 256-261 (2005).

Angelo et al. "An S-nitrosothiol (SNO) synthase function of hemoglobin that utilizes nitrite as a substrate," *Proc. Natl. Acad. Sci. USA* 103 (33): 8366-8371 (2006).

Aslan et al., "Oxygen radical inhibition of nitric-oxide dependent vascular function in sickle cell disease," *PNAS*, 98:15215-15220 (2001).

Basireddy et al. "Effects of sodium nitrite on ischemia=reperfusion injury in the rat kidney" *Am J Physiol Renal Physiol* 290: 779-786 (2005).

Bhugra et al., "A study of nitrogen oxide containing vasodilators on guinea pig trachea, a nonvascular smooth muscle," *Indian J. Pharmac.*, 17:92-97 (1985).

Bian et al., "Nitric Oxide (NO)—Biogeneration, regulation, and relevance to human diseases," *Frontiers in Bioscience*, 8:d264-278 (2003).

(56) References Cited

OTHER PUBLICATIONS

Björne et al., "Nitrite in saliva increases gastric mucosal blood flow and mucus thickness," *J. Clin. Invest.*, 113:106-114 (2004).
Bryson, *Comprehensive Review in Toxicology for Emergency Clinicians*, 3rd Edition, p. 361 (1996).
Butler et al., "Therapeutic Uses of Inorganic Nitrite and Nitrate: From the Past to the Future," *Circulation*, 117:2151-2159 (2008).
Cannon et al., "Effects of inhaled nitric oxide on regional blood flow are consistent with intravascular nitric oxide delivery," *J. Clin. Invest.*, 108:279-287 (2001).
Channon, "Tetrahydrobiopterin: Regulator of Endothelial Nitric Oxide Synthase in Vascular Disease," *Trends Cardiovasc. Med.*, 14(8):323-327 (2004).
Cokic et al., "Hydroxyurea induces fetal hemoglobin by the nitric oxide-dependent activation of soluble guanylyl cyclase," *J. Clin. Invest.*, 111:231-239 (2003).
Cosby et al., "Nitrite reduction to nitric oxide by deoxyhemoglobin vasodilates the human circulation," *Nature Medicine*, 9(12):1498-1505 (2003), plus Supplementary matter (5 pages).
Crawford et al., "Vasoactivity of S-nitrosohemoglobin: role of oxygen, heme and NO oxidation states," *Blood*, 101:4408-4415 (2003).
Crawford et al. "Hypoxia, red blood cells, and nitrite regulate NO-dependent hypoxic vasodilation," *Blood* 107 (2): 566-574 (2006).
Deem et al., "Effects of S-Nitrosation of Hemoglobin on Hypoxic Pulmonary Vasoconstriction and Nitric Oxide Flux," *Am. J. Respir. Crit. Care Med.*, 163:1164-1170 (2001).
Deem et al., "Effects of S-Nitrosation and Cross-Linking of Hemoglobin on Hypoxic Pulmonary Vasoconstriction in Isolated Rat Lungs," *Circ. Res.*, 91:626-632 (2002).
Demoncheaux et al., "Circulating nitrite anions are a directly acting vasodilator and are donors for nitric oxide," *Clin. Sci.*, 102:77-83 (2002).
Doyle et al., "Kinetics and Mechanism of the Oxidation of Human Deoxyhemoglobin by Nitrites," *J. Biol. Chem.*, 256(23):12393-12398 (1981).
Duranski et al. "Cytoprotective effects of nitrite during in vivo ischemia-reperfusion of the heart and liver," *Journal of Clinical Investigation* 115 (5): 1232-1240 (2005).
Duriez et al., "A Common Variant in Combination with a Nonsense Mutation in a Member of the Thioredoxin Family Causes Primary Ciliary Dyskinesia," *PNAS*, 104:3336-3341 (2007).
Fox-Robichaud et al., "Inhaled NO as a Viable Antiadhesive Therapy for Ischemia/Reperfusion Injury of Distal Microvascular Beds," *J. Clin. Invest.*, 101:2497-2505 (1998).
Furchgott et al., "Reactions of Strips of Rabbit Aorta to Epinephrine, Isopropylarterenol, Sodium Nitrite and Other Drugs," *J Pharmacol Exp Ther*, 108:129-143 (1952).
Gianetti et al., "Supplemental nitric oxide and its effect of myocardial injury and function in patients undergoing cardiac surgery with extracorporeal circulation," *J. Thorac. Cardiovasc. Surg.*, 127:44-50 (2004).
Gladwin et al., "Inhaled nitric oxide augments nitric oxide transport on sickle cell hemoglobin without affecting oxygen affinity," *J Clin. Invest.*, 104:937-945 (1999).
Gladwin et al., "The Acute Chest Syndrome in Sickle Cell Disease, Possible Role of Nitric Oxide in Its Pathophysiology and Treatment," *Am. J. Respir. Crit. Care Med.*, 159:1368-1376 (1999).
Gladwin et al., "Pathogenesis and treatment of acute chest syndrome of sickle-cell anaemia," *Lancet*, 355:1476-1478 (2000).
Gladwin et al., "Relative role of heme nitrosylation and β-cysteine 93 nitrosation in the transport and metabolism of nitric oxide by hemoglobin in the human circulation," *PNAS*, 97:9943-9948 (2000).
Gladwin et al., "Role of circulating nitrite and S-nitrosohemoglobin in the regulation of regional blood flow in humnas," *PNAS*, 97:11482-11487 (2000).
Gladwin et al., "Nitric oxide therapy in sickle cell disease," *Seminars in Hematology*, 38:333-342 (2001).
Gladwin et al., "Nitric Oxide Transport on Sickle Cell Hemoglobin: Where Does it Bind?" *Free Radic. Res.*, 35:175-180 (2001).
Gladwin et al., "Nitric oxide donor properties of hydroxyurea in patients with sickle cell disease," *British J. Haematology*, 116:436-444 (2002).
Gladwin et al., "S-Nitrosohemoglobin Is Unstable in the Reductive Erythrocyte Environment and Lacks $O_2$/NO-Linked Allosteric Function," *J. Biol. Chem.*, 277:27818-27828 (2002).
Gladwin et al., "Divergent Nitric Oxide Bioavailability in Men and Women With Sickle Cell Disease," *Circulation*, 107:271-278 (2003).
Gladwin et al., "Nitric oxide's reactions with hemoglobin: a view through the SNO-storm," *Nature Medicine*, 9:496-500 (2003).
Gladwin, "Haldane, hot dogs, halitosis, and hypoxic vasodilation: the emerging biology of the nitrite anion," *J. Clin. Invest.*, 113:19-21 (2004).
Gladwin et al., "The emerging biology of the nitrite anion," *Nature Chem. Biol.*, 1(6):308-314 (2005).
Gladwin, "Nitrite as an intrinsic signaling molecule," *Nature Chemical Biology* 1: 245-246 (2005).
Gladwin et al. "Corrigendum: The emerging biology of the nitrite anion," *Nature Chemical Biology* 2: 110 (2006).
Goldfrank et al., *Goldfrank's Toxicological Emergencies*, 7th Edition, p. 1511 (2002).
Gow and Stamler, "Reactions between nitric oxide and haemoglobin under physiological conditions," *Nature* 391: 169-173 (1998) (Abstract Only).
Gow et al. "The oxyhemoglobin reaction of nitric oxide," *Proc. Natl. Acad. Sci. USA* 96: 9027-9032 (1999).
Gruetter et al., "Methylene blue inhibits coronary arterial relaxation and guanylate cyclase activation by nitroglycerin, sodium nitrite, and amyl nitrite," *Can. J. Physiol. Pharmacol.*, 59:150-156 (1981).
Guo et al., "Endothelial Preserving Actions of a Nitric Oxide Donor in Carotid Arterial Intimal Injury," *Meth. Find. Exp. Clin. Pharmacol.*, 16(5):347-354 (1994).
Han et al., "Nitric oxide reaction with red blood cells and hemoglobin under heterogeneous conditions," *PNAS*, 99:7763-7768 (2002).
Head et al., "Low Concentrations of Nitric Oxide Increase Oxygen Affinity of Sickle Erythrocytes In Vitro and In Vivo," *J. Clin. Invest.*, 100(5):1193-1198 (1997).
Henderson and Raskin, "Hot-Dog Headache: Individual Susceptibility to Nitrite[1]," *Lancet*, 300(7788):1162-1163 (1972) (Abstract Only).
Herold and Röck, "Reactions of Deoxy-, Oxy-, and Methemoglobin with Nitrogen Monoxide: Mechanistic Studies of the S-Nitrosothiol Formation Under Different Mixing Conditions," *J. Biol. Chem.*, 278:6623-6634 (2003).
Hobbs et al., "Haemoglobin: NO transporter, NO inactivator or None of the above?" *Trends Pharmacol. Sci.*, 23:406-411 (2002).
Hrinczenko et al., "Effect of nitric oxide and nitric oxide donors on red blood cell oxygen transport," *Br. J. Haematol.*, 110:412-419 (2000).
Hunter et al., "Inhaled nebulized nitrite is a hypoxia-sensitive NO-dependent selective pulmonary vasodilator," *Nat. Med.*, 10(10):1122-1227 (2004).
Ignarro et al., "Endothelium-derived relaxing factor produced and released from artery and vein is nitric oxide," *PNAS*, 84:9265-9269 (1987).
Isbell et al., "Hemoglobin Oxygen fractional saturation regulates nitrite-dependent vasodilation of aortic ring bioassays," *Am J Physiol Heart Circ Physiol*, 293:H2565-H2572 (2007).
Jison and Gladwin, "Hemolytic Anemia-associated Pulmonary Hypertension of Sickle Cell Disease and the Nitric Oxide/Arginine Pathway," *Am. J. Respir. Crit. Care Med.*, 168:3-4 (2003).
Joshi et al., "Nitric oxide is consumed, rather than conserved, by reaction with oxyhemoglobin under physiological conditions," *PNAS*, 99(16):10341-10346 (2002).
Kim-Shapiro et al. "Unraveling the Reaction of Nitric Oxide, Nitrite, and Hemoglobin in Physiology and Therapeutics," *Aterioscler. Thromb. Vasc. Biol.* 26: 697-705 (2006).
King, "A role for nitric oxide in hydroxyurea-mediated fetal hemoglobin induction," *J. Clin. Invest.*, 111:171-172 (2003).
Kohelet, "Nitric Oxide Inhalation and High Frequency Oscillatory Ventilation for Hypoxemic Respiratory Failure in Infants," *Israel Med. Assoc. J.*, 5:19-23 (2003).

(56) References Cited

OTHER PUBLICATIONS

Kozlov et al., "Mechanisms of Vasodilation Induced by Nitrite Instillation in Intestinal Lumen: Possible Role of Hemoglobin," *Antioxid. Redox. Signal.*, 7:515-521 (2005).
Kuo et al., "Nitrosation of cysteine and reduced gluththione by nitrite at physiological pH," *Frontiers in Bioscience*, 8:a62-69 (2003).
Lancaster, "Reaping of nitric oxide by sickle cell disease," *PNAS*, 99:552-553 (2002).
Lauer et al., "Plasma nitrite rather than nitrate reflects regional endothelial nitric oxide synthase activity but lacks intrinsic vasodilator action," *PNAS*, 98:12814-12819 (2001).
Lefer, "Myocardial Protective Actions of Nitric Oxide Donors After Myocardial Ischemia and Reperfusion," *New Horizons*, 3(1):105-112 (1995).
Lefer, "Nitrite therapy for protection against ischemia-reperfusion injury," *Am. J. Physiol. Renal Physiol.*, 290:F777-F778 (2005).
Li et al., "Characterization of the effects of oxygen on xanthine oxidase-mediated nitric oxide formation," *J. Biol. Chem.*, 279(17):16939-16946 (2004).
Liao, "Blood feud: Keeping hemoglobin from nixing NO," *Nature Medicine*, 8(12):1350-1351 (2002).
Luchsinger et al. "Routes to S-nitroso-hemoglobin formation with heme redox and preferential reactivity in the subunits," *Proc. Natl. Acad. Sci. USA* 100 (2): 461-466 (2003).
Luchsinger et al., "Assessments of the chemistry and vasodilatory activity of nitrite with hemoglobin under physiologically relevant conditions," *J. Inorg. Biochem.*, 99:912-921 (2005).
Lyra and Diniz, "The Importance of Surfactant on the Development of Neonatal Pulmonary Diseases," *Clinics*, 62:181-190 (2007).
Matsunaga and Furchgott, "Interactions of light and sodium nitrite in producing relaxation of rabbit aorta," *J. Pharmacol. Exp. Ther.*, 248(2):687-695 (1989).
Matthew, "Vaso-dilators in high blood pressure," *Quarterly Journal of Medicine*, 2:261-278 (1908).
McLean et al., "Inducible expression of the kinin $B_1$ receptor in the endotoxemic heart: mechanisms of des-$Arg^9$bradykinin-induced coronary vasodilation," *Br. J. Pharmacol.*, 128:275-282 (1999).
McMahon et al., "Nitric Oxide in the Human Respiratory Cycle," *Nature Medicine*, 8(7):711-717 (2002).
McMahon et al. "A nitric oxide processing defect of red blood cells created by hypoxia: Deficiency of S-nitrosohemoglobin in pulmonary hypertension," *Proc. Natl. Acad. Sci. USA* 102 (41): 14801-14806 (2005).
Modin et al., "Nitrite-derived nitric oxide: a possible mediator of 'acidic-metabolic' vasodilation," *Acta. Physiol. Scand.*, 171:9-16 (2001).
Moore et al., "Regional Cerebral Hyperperfusion and Nitric Oxide Pathway Dysregulation in Fabry Disease," *Circulation*, 104:1506-1512 (2001).
Moya et al., "Inhaled ethyl nitrite gas for persistent pulmonary hypertension of the newborn," *Lancet*, 360:141-143 (2002).
Nachtsheim, "Sildenafil: A Milestone in the Treatment of Impotence," *West J Med*, 169(2):112-113 (1998).
Nagababu et al., "Active Nitric Oxide Produced in the Red Cell under Hypoxic Conditions by Deoxyhemoglobin-mediated Nitrite Reduction," *J. Biol. Chem.*, 278(47):46349-46356 (2003).
Okamoto et al., "Nitrite-derived nitric oxide formation following ischemia-reperfusion injury in kidney," *Am. J. Physiol. Renal Physiol.* 288:F182-187 (2005).
Park et al., "Combined Effects of Inhaled Nitric Oxide and a Recruitment Maneuver in Patients with Acute Respiratory Distress Syndrome," *Yonsei Med. J.*, 44(2):219-226 (2003).
Pawloski et al., "Export by Red Blood Cells of Nitric Oxide Bioactivity," *Nature*, 409:622-626 (2001).
Pawloski et al., "Impaired vasodilation by red blood cells in sickle cell disease," *PNAS USA*, 102(7):2531-2536 (2005).
Pi et al., "Effects of adenosine on ischaemia-reperfusion injury associated with rat pancreas transplantation," *British J. Surgery*, 88:1366-1375 (2001).
Pluta et al., "Nitrite Infusions to Prevent Delayed Cerebral Vasospasm in a Primate Model of Subarachnoid Hemorrhage," *JAMA*, 293:1477-1484 (2005).
Poderoso et al., "Nitric oxide regulates oxygen uptake and hydrogen peroxide release by the isolated beating rat heart," *Am. J. Physiol.*, 274 (*Cell Physiol*. 43): C112-119 (1998).
Rassaf et al., "Evidence for in vivo transport of bioactive nitric oxide in human plasma," *J. Clin. Invest.*, 109:1241-1248 (2002).
Reiter et al., "Cell-free hemoglobin limits nitric oxide bioavailability in sickle-cell disease," *Nature Medicine*, 8:1383-1389 (2002).
Reiter and Gladwin, "An emerging role for nitric oxide in sickle cell disease vascular homeostasis and therapy," *Curr. Opin. Hematol.*, 10:99-107 (2003).
Schechter et al., "NO solutions?" *J. Clin. Invest.*, 109:1149-1151 (2002).
Schechter and Gladwin, "Hemoglobin and the Paracrine and Endocrine Functions of Nitric Oxide," *N. Engl. J. Med.*, 348(15):1483-1485 (2003).
Schermuly et al., "Reversal of experimental pulmonary hypertension by PDGF inhibition," *J. Clin. Invest.*, 115:2811-2821 (2005).
Shiva et al. "Ceruloplasmin is a NO oxidase and nitrite synthase that determines endocrine NO homeostasis," *Nature Chemical Biology* 2: 486-493 (2006).
Stubbe et al., "Inhaled nitric oxide reduces lung edema during fluid resuscitation in ovine acute lung injury," *Intens. Care Med.*, 29(10):1790-1797 (2003).
Sullivan et al., "Nitric oxide successfully used to treat acute chest syndrome of sickle cell disease in a young adolescent," *Crit. Care Med.*, 27:2563-2568 (1999).
Tiravanti et al., "Nitrosyl-Heme Complexes Are Formed in the Ischemic Heart," *J. Biol. Chem.*, 279(12):11065-11073 (2004).
Tsikas and Frolich, "Is circulating nitrite a directly acting vasodilator?" *Clin. Sci.*, 103:107-110 (2002).
Tsuchiya et al., "Malfunction of Vascular Control in Lifestyle-Related Diseases: Formation of Systemic Hemoglobin-Nitric Oxide Complex (HbNO) From Dietary Nitrite," *J. Pharmacol. Sci.*, 96:395-400 (2004).
Tsuchiya et al., "Nitrite is an alternative source of NO in vivo," *Am. J. Physiol. Heart Circ. Physiol.*, 288:H2163-2170 (2005).
Tucker et al., "Effect of nitric-oxide-generating system on microcirculatory blood flow in skin of patients with severe Raynaud's syndrome: a biological trial," *Lancet*, 354:1670-1675 (1999).
Uga et al., "Nitric oxide inhalation therapy in very low-birth weight infants with hypoplastic lung due to oligohydramnics," *Pediatr. Int.*, 46:10-14 (2004).
Wagner et al., "Nitric Oxide Inhalation in the Treatment of Right Ventricular Infarction," *Eur. Heart J.*, 23:326 Suppl. S P1717 (2002).
Wanstall et al., "Vascular smooth muscle relaxation mediated by nitric oxide donors: a comparison with acetylcholine, nitric oxide and nitroxyl ion," *British Journal of Pharmacology*, 134:463-472 (2001).
Webb et al., "Inorganic nitrite: protector against ischaemia reperfusion injury in the heart," *Br. J. Pharmacol.*, 138 (Proceedings Supplement):20P (Apr. 2003).
Webb et al., "Reduction of nitrite to nitric oxide during ischemia protects against myocardial ischemia-reperfusion damage," *PNAS*, 101(37):13683-13688 (2004).
Weyerbrock et al., "Selective opening of the blood-tumor barrier by a nitric oxide donor and long-term survival in rats with C6 gliomas," *J. Neurosurg.*, 99:728-737 (2003).
Wink, "Ion implicated in blood pact," *Nature Medicine*, 9(12):1460-1461 (2003).
Winslow, "Red Cell Substitutes," *Seminars in Hematology* 44:51-59 (2007).
Wolzt et al., "Biochemical Characterization of S-Nitrosohemoglobin. Mechanisms Underlying Synthesis, NO release, and Biological Activity," *J. Biol. Chem.*, 274:28983-28990 (1999).
Xu et al., "Effects of Iron Nitrosylation on Sickle Cell Hemoglobin Solubility," *J. Biol. Chem.*, 277:36787-36792 (2002).
Yang et al., "Methodologies for the Sensitive and Specific Measurement of S-nitrosothiols, Iron-nitrosyls, and Nitrite in Biological Samples," *Free Radic. Res.*, 37:1-10 (2003).

(56) References Cited

OTHER PUBLICATIONS

Zhang et al., "Nitric oxide donors increase blood flow and reduce brain damage in focal ischemia: evidence that nitric oxide is beneficial in the early stages of cerebral ischemia," *J Cereb. Blood Flow Metab.*, 14(2):217-26 (1994).

Zuzak et al., "Imaging hemoglobin oxygen saturation in sickle cell disease patients using noninvasive visible reflectance hyperspectral techniques: effects of nitric oxide," *Am. J. Physiol. Heart Circ. Physiol.*, 285:H1183-H1189 (2003).

Six letters to the Editor, *N. Engl. J. Med.*, 349(4):402-405 (2003).

The Merck Index, Eleventh Edition, "An encyclopedia of chemicals, drugs, and biologicals," p. 1365 (1989).

Agency for Toxic Substances and Disease Registry, "Case Studies in Environmental Medicine (CSME): Nitrate/Nitrite Toxicity," Course SS3054, ATSDR Publication No. ATSDR-HE-CS-2002-0007, Revision Date: Jan. 2001.

BBC News, www.bbc.co.uk/2/hi/health/516365.stm, published Nov. 12, 1999, printed Mar. 23, 2004. "Gel improves circulation disorder.".

Boston.com, Neergard, "Sodium nitrite could be disease cure," www.boston.com/yourlife/health/diseases/articles/2005/09/05/sodium_nitrite_could . . . printed Sep. 6, 2005.

Mack et al., "Sodium nitrite increases regional blood flow in patients with sickle cell disease," Poster displayed at least as early as Apr. 12, 2005 at 28th Annual Meeting of the National Sickle Cell Disease Program.

Mack et al., "Sodium nitrite increases regional blood flow in patients with sickle cell disease," Abstract for poster displayed at least as early as Apr. 12, 2005 at 28th Annual Meeting of the National Sickle Cell Disease Program.

Hot dog nutrition facts; retrieved from the internet [online] on Apr. 14, 2008; retrieved from http://www.calorie-count.com/claories/item/21118.html; 2 pages.

Wanstall and O'Donnell, "Responses to vasodilator drugs on pulmonary artery preparations from pulmonary hypertensive rats," *Br J Pharmacol* 105:152-158, 1992.

Bryan et al., "Nitrite is a Signaling Molecule and Regulator of Gene Expression in Mammalian Tissues," *Nat. Chem. Biol.*, 1(5):290-297, 2005.

Laustiola et al., "Exogenous GTP Enhances the Effects of Sodium Nitrite on Cyclic GMP Accumulation, Vascular Smooth Muscle Relaxation and Platelet Aggregation," *Pharmacol. Toxicol.*, 68:60-63, 1991.

Minamino et al., "Plasma Levels of Nitrite/Nitrate and Platelet cGMP Levels are Decreased in Patients with Atrial Fibrillation," *Arterioscler. Thromb. Vasc. Biol.*, 17(11):3191-3195, 1997.

Radomski et al., "Endogenous Nitric Oxide Inhibits Human Platelet Adhesion to Vascular Endothelium," *The Lancet*, 2(8567):1057-1058, 1987.

Schäfer et al., "Rapid Regulation of Platelet Activation In Vivo by Nitric Oxide," *Circulation*, 109:1819-1822, 2004.

Schafer et al., "Inhibition of Platelet Function by Organic Nitrate Vasodilators," *Blood*, 55(4):649-654, 1980.

Wilkins, "The George E. Brown Memorial Lecture: The Physiology of the Peripheral Circulation. A review of Personal Experiences over a Period of Twenty-Five Years," *Circulation* 25:437-442, 1962.

Zelis et al., "A Comparison of the Effects of Vasodilator Stimuli on Peripheral Resistance Vessels in Normal Subjects and in Patients with Congestive Heart Failure," *J. Clin. Invest.* 47:960-970, 1968.

\* cited by examiner

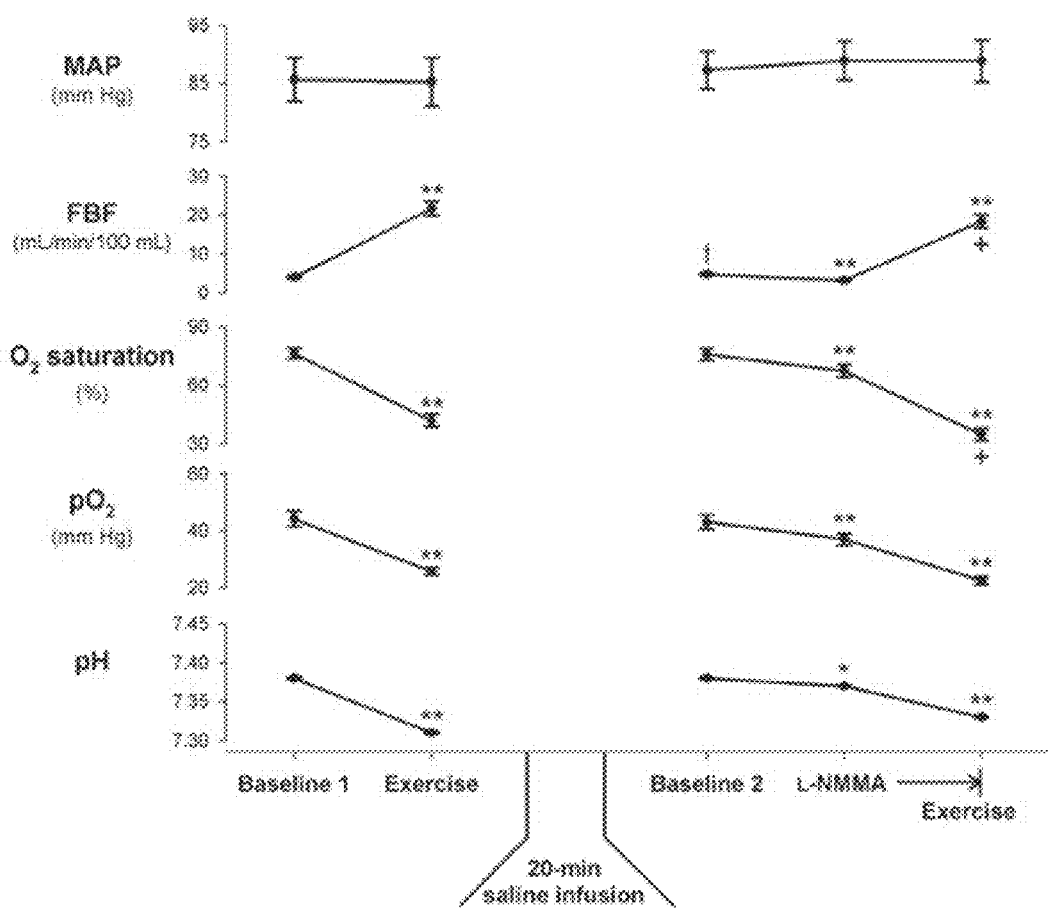

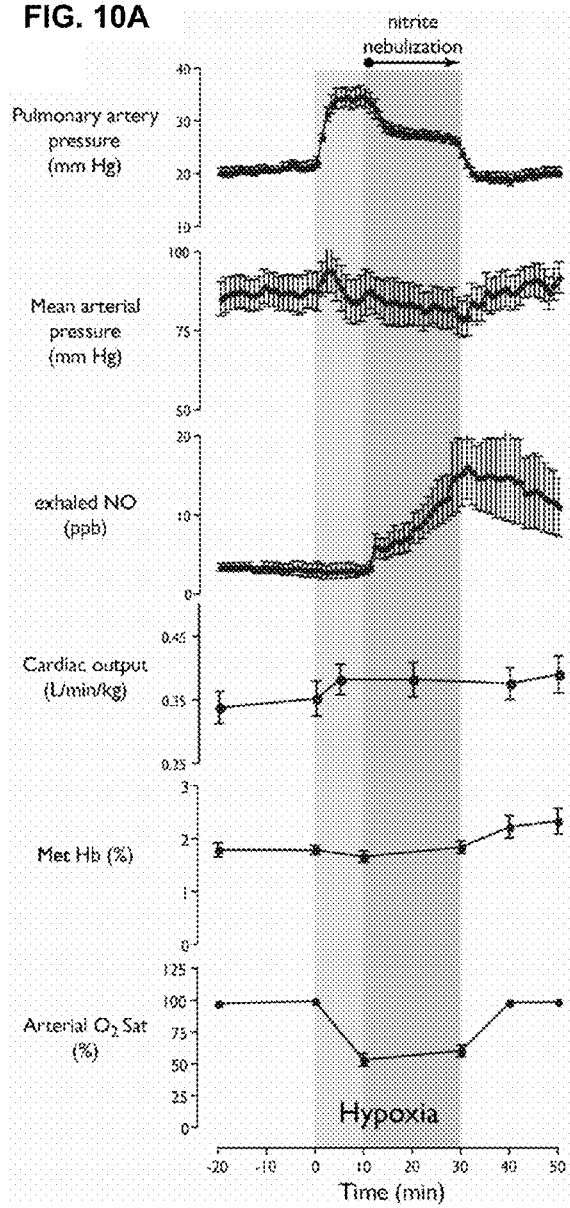
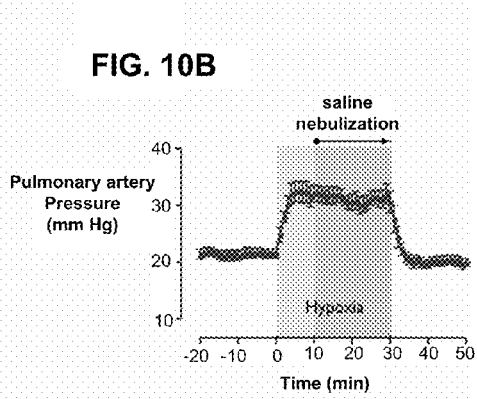
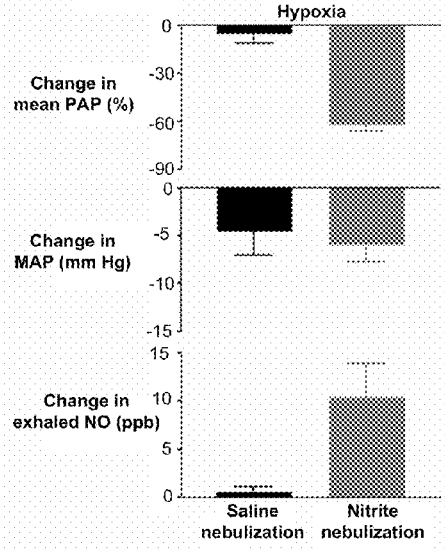

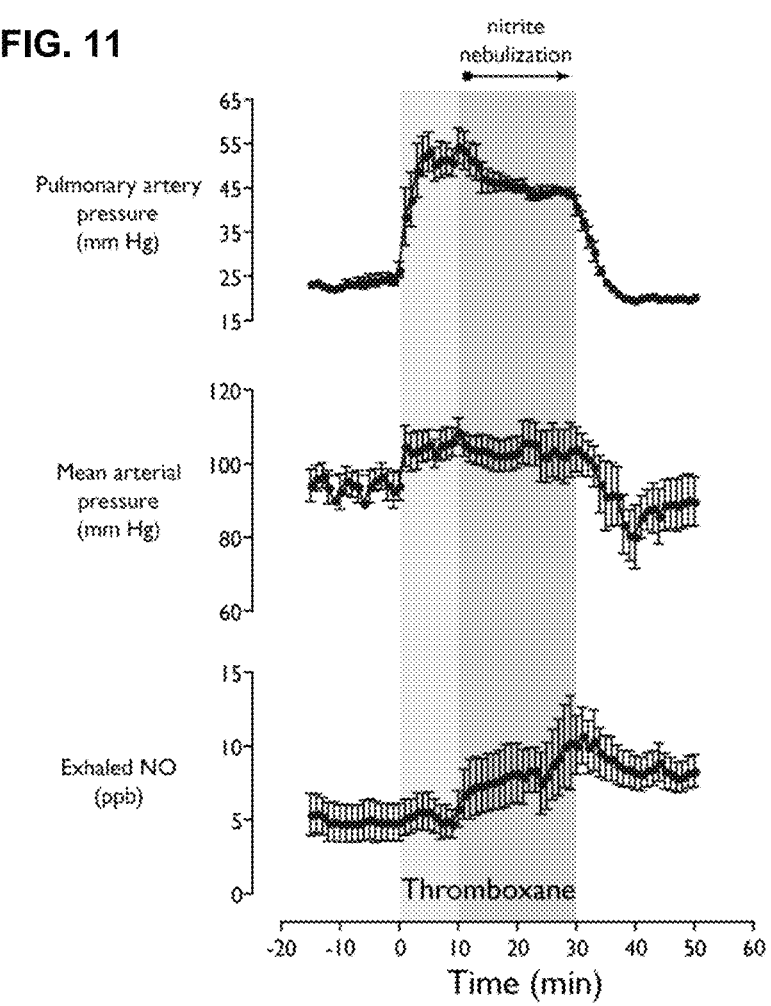

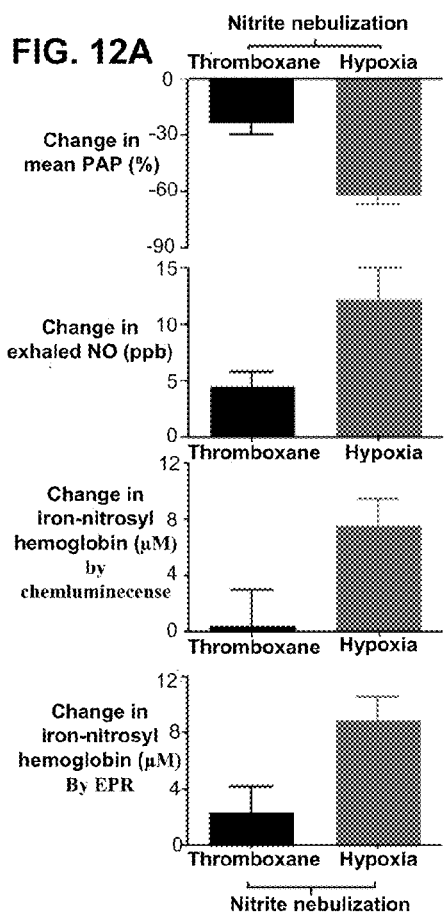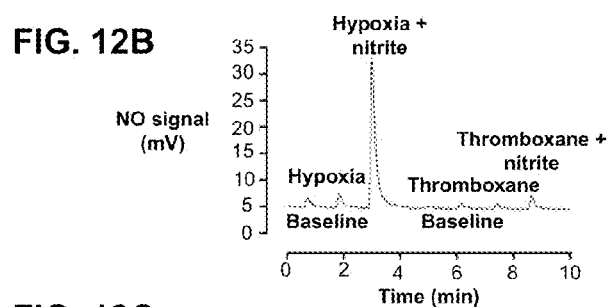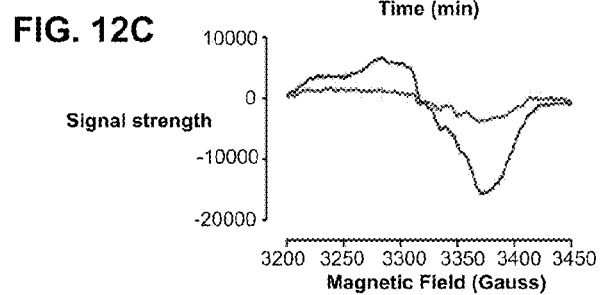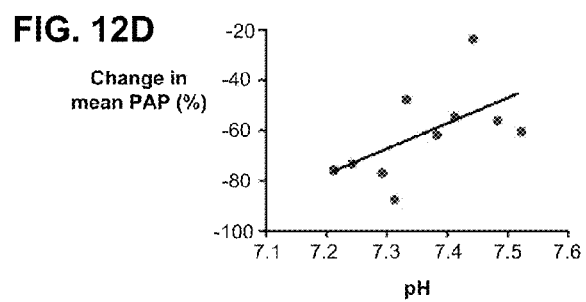
FIG. 12A
FIG. 12B
FIG. 12C
FIG. 12D

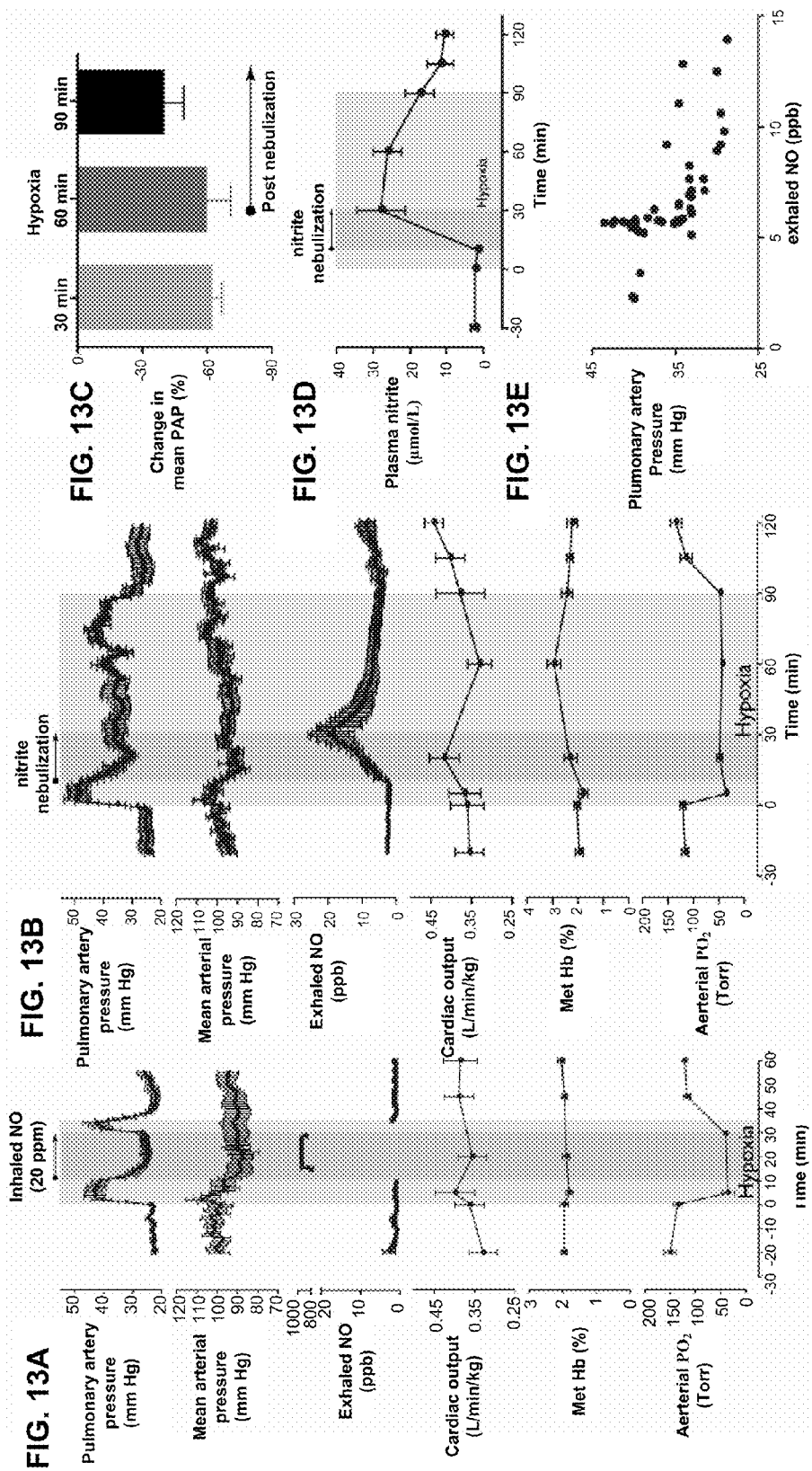

USE OF NITRITE SALTS FOR THE TREATMENT OF CARDIOVASCULAR CONDITIONS

CROSS REFERENCE TO RELATED APPLICATIONS

This is a continuation of U.S. application Ser. No. 10/563,683, filed Oct. 4, 2006, which is the §371 U.S. National Stage of PCT/US2004/022232, filed Jul. 9, 2004, which was published in English under PCT Article 2(2), and which in turn claims the benefit of U.S. Provisional Application No. 60/485,959, filed Jul. 9, 2003, and U.S. Provisional Application No. 60/511,244, filed Oct. 14, 2003. This is also a continuation of U.S. application Ser. No. 10/563,682, filed Jan. 6, 2006 now abandoned, which is the §371 U.S. National Stage of PCT/US2004/021985, filed Jul. 9, 2004, which was published in English under PCT Article 2(2), and which in turn also claims the benefit of U.S. Provisional Application No. 60/485,959, filed Jul. 9, 2003, and U.S. Provisional Application No. 60/511,244, filed Oct. 14, 2003. All of the above-referenced applications are herein incorporated by reference in their entirety.

GOVERNMENT INTEREST STATEMENT

This invention was made with government support under Grant No. HL58091 and Grant No. HL70146, both awarded by the National Institutes of Health. The government has certain rights in the invention. The government also may have certain rights in the invention due to at least one inventor's employment by the National Institutes of Health.

BACKGROUND OF THE DISCLOSURE

The last decade has seen an increase in the understanding of the critical role nitric oxide as a blood vessel dilator contributing to the regulation of blood flow and cardiovascular homeostasis. Nitric oxide may be oxidized in blood to nitrite ($NO_2^-$), an anion considered to be an inert metabolic end product of such nitric oxide oxidation. In vivo plasma levels of nitrite have been reported to range from 150 to 1000 nM, and the nitrite concentration in aortic ring tissue has been reported to be in excess of 10,000 nM (Rodriguez et al., *Proc Natl Acad Sci USA*, 100, 336-41, 2003; Gladwin et al., *Proc Natl Acad Sci USA*, 97, 9943-8, 2000; and Rassaf et al., *Nat Med*, 9, 481-3, 2003). This potential storage pool for NO is in excess of plasma S-nitrosothiols, which have been reported to be less than 10 nM in human plasma (Rassaf et al., *Nat Med*, 9, 481-3, 2003; Rassaf et al., *Free Radic Biol Med*, 33, 1590-6, 2002; Rassaf et al., *J Clin Invest*, 109, 1241-8, 2002; and Schechter et al., *J Clin Invest*, 109, 1149-51, 2002). Mechanisms have been proposed for the in vivo conversion of nitrite to NO, for example, by enzymatic reduction by xanthine oxidoreductase or by non-enzymatic disproportionation/acidic reduction (Millar et al., *Biochem Soc Trans*, 25, 528S, 1997; Millar et al., *FEBS Lett*, 427, 225-8, 1998; Godber et al., *J Biol Chem*, 275, 7757-63, 2000; Zhang et al., *Biochem Biophys Res Commun*, 249, 767-72, 1998 [published erratum appears in *Biochem Biophys Res Commun* 251, 667, 1998]; Li et al., *J Biol Chem*, 276, 24482-9, 2001; Li et al., *Biochemistry*, 42, 1150-9, 2003; Zweier et al., *Nat Med*, 1, 804-9, 1995; Zweier et al., *Biochim Biophys Acta*, 1411, 250-62, 1999; and Samouilov et al., *Arch Biochem Biophys*, 357:1-7, 1998).

Arterial-to-venous gradients of nitrite across the human forearm at rest and during regional NO synthase inhibition have been observed, with increased consumption of nitrite occurring with exercise (Gladwin et al., *Proc Natl Acad Sci USA*, 97, 9943-8, 2000; Gladwin et al., *Proc Natl Acad Sci USA*, 97, 11482-11487, 2000; and Cicinelli et al., *Clin Physiol*, 19:440-2, 1999). Kelm and colleagues have reported that large artery-to-vein gradients of nitrite form across the human forearm during NO synthase inhibition (Lauer et al., *Proc Natl Acad Sci USA*, 98, 12814-9, 2001). Unlike the more simple case of oxygen extraction across a vascular bed, nitrite may be both consumed, as evidenced by artery-to-vein gradients during NO synthase inhibition and exercise, and produced in the vascular bed by endothelial nitric oxide synthase-derived NO reactions with oxygen.

At high concentrations, nitrite has been reported to be a vasodilator in vitro (Ignarro et al., *Biochim Biophys Acta*, 631, 221-31, 1980; Ignarro et al., *J Pharmacol Exp Ther*, 218, 739-49, 1981; Moulds et al., *Br J Clin Pharmacol*, 11, 57-61, 1981; Gruetter et al., *J Pharmacol Exp Ther*, 219, 181-6, 1981; Matsunaga et al., *J Pharmacol Exp Ther*, 248, 687-95, 1989; and Laustiola et al., *Pharmacol Toxicol*, 68, 60-3, 1991). The levels of nitrite shown to vasodilate in vitro have always been in excess of 100,000 nM (100 µM) and usually at millimolar concentrations.

Consistent with the high concentrations of nitrite required to vasodilate in vitro, when Lauer and colleagues infused nitrite into the forearm circulation of human subjects, they reported no vasodilatory effects, even with concentrations of 200 µM in the forearm (Lauer et al., *Proc Natl Acad Sci USA*, 98, 12814-9, 2001). Lauer et al. reported that a "complete lack of vasodilator activity of intraarterial infusions of nitrite clearly rules out any role for this metabolite in NO delivery" and concluded that "physiological levels of nitrite are vasodilator-inactive." Furthermore, Rassaf and colleagues also failed to find a vasodilatory effect in humans following infusion of nitrite (Rassaf et al., *J Clin Invest*, 109, 1241-8, 2002). Thus, in vivo studies have concluded that physiological levels of nitrites do not serve as a source for NO, and that physiological levels of nitrites do not have a role in regulating blood pressure.

Historically, nitrite has been used as a treatment for cyanide poisoning. High concentrations are infused into a subject suffering cyanide poisoning in order to oxidize hemoglobin to methemoglobin, which will bind cyanide. These high concentrations of nitrite produce clinically significant methemoglobinemia, potentially decreasing oxygen delivery. While these high concentrations of nitrite have been shown to decrease blood pressure in humans, the amount of methemoglobin formed precluded a use for nitrite in the treatment of other medical conditions.

Therefore, the state of the art was that nitrite was not a significant vasodilator at concentrations below 100 µM in vitro, and even when infused into humans at concentrations of 200 µM in the forearm. It was also the state of the art that nitrite was not converted to nitric oxide in the human blood stream.

SUMMARY OF THE DISCLOSURE

It has been surprisingly discovered that administration of pharmaceutically-acceptable salts of nitrite is useful in the regulation of the cardiovascular system. It has also been surprisingly discovered that nitrite is reduced to nitric oxide in vivo, and that the nitric oxide produced thereby is an effective vasodilator. These effects surprisingly occur at doses that do not produce clinically significant methemoglobinemia. These discoveries now enable methods to prevent and treat conditions associated with the cardiovascular system, for example, high blood pressure, pulmonary hypertension, cerebral vasospasm and tissue ischemia-reperfusion injury. These discoveries also provide methods to increase blood flow to tissues, for example, to tissues in regions of low oxygen tension. It is particularly surprising that the nitrite does not need to be applied in an acidified condition in order for it to be effective in regulating the cardiovascular system, and more particularly to act as a vasodilator in vivo.

It has now been surprisingly discovered by the inventors that nitrite can serve as a vasodilator in humans at much lower concentrations (as low as 0.9 µM) than have been used in the past for cyanide poisoning. The mechanism is believed to involve a reaction of nitrite with deoxygenated hemoglobin and red blood cells, to produce the vasodilating gas nitric oxide. This potent biological effect is observed at doses of nitrite that do not produce clinically significant methemoglobinemia (for instance, less than 20%, more preferably less than 5% methemoglobin in the subject).

It has been discovered that nitrite is converted to nitric oxide in vivo, and that the nitric oxide produced thereby is an effective vasodilator. Further, it has been surprisingly discovered that administration of nitrite, for instance a pharmaceutically-acceptable salt of nitrite, to a subject causes a reduction in blood pressure and an increase in blood flow to tissues, for example, to tissues in regions of low oxygen tension. These discoveries now enable useful methods to regulate the cardiovascular system, for instance to prevent and treat malconditions associated with the cardiovascular system, for example, high blood pressure, or organs, tissues, or systems suffering a lack of or inadequate blood flow. Non-limiting examples of contemplated malconditions include stroke, heart disease, kidney disease and failure, eye damage including hypertensive retinopathy, diabetes, and migraines.

In one example embodiment, the present disclosure provides a method for decreasing a subject's blood pressure or increasing blood flow, including in a particular embodiment administering to the subject sodium nitrite at about 36 moles per minute into the forearm brachial artery.

The present disclosure additionally provides a method for increasing blood flow to a tissue of a subject, including administering to the subject an effective amount of pharmaceutically-acceptable nitrite, such as a salt thereof, so as to increase blood flow to a tissue of the subject. The blood flow may be specifically increased in tissues in regions of low oxygen tension. The present disclosure also provides a method for decreasing a subject's blood pressure, comprising administering to the subject an effective amount of pharmaceutically-acceptable nitrite so as to decrease the subject's blood pressure.

The present disclosure further provides a method for treating a subject having a condition associated with elevated blood pressure, including administering to the subject an effective amount of pharmaceutically-acceptable nitrite so as to treat at least one vascular complication associated with the elevated blood pressure.

Also provided is a method for treating a subject having a hemolytic condition, including administering to the subject an effective amount of pharmaceutically-acceptable nitrite so as to treat at least one vascular complication associated with the hemolytic condition.

The disclosure further provides a method for treating a subject having a condition associated with elevated blood pressure in the lungs, e.g. pulmonary hypertension, including administering to the subject an effective amount of pharmaceutically-acceptable nitrite. In some embodiments, this includes treating a subject having neonatal pulmonary hypertension. In some embodiments, this includes treating a subject having primary and/or secondary pulmonary hypertension. In some embodiments for treating subjects having a condition associated with elevated blood pressure in the lungs, the nitrite is nebulized.

Also contemplated herein are methods for treating, ameliorating, or preventing other conditions of or associated with blood flow, including vasospasm, stroke, angina, revascularization of coronary arteries and other arteries (peripheral vascular disease), transplantation (e.g., of kidney, heart, lung, or liver), treatment of low blood pressure (such as that seen in shock or trauma, surgery and cardiopulmonary arrest) to prevent reperfusion injury to vital organs, cutaneous ulcers (e.g., with topical, non-acidified nitrite salt), Reynaud's phenomenon, treatment of hemolytic conditions (such as sickle cell, malaria, TTP, and HUS), hemolysis caused by immune incompatibility before and after birth, and other conditions listed herein.

Also provided herein are methods of administering a pharmaceutically-acceptable nitrite salt to a subject, for treating, preventing or ameliorating a condition selected from: (a) ischemia-reperfusion injury (e.g., hepatic or cardiac or brain ischemia-reperfusion injury); (b) pulmonary hypertension (e.g., neonatal pulmonary hypertension); or (c) cerebral artery vasospasm. Also contemplated are methods for treatment, prevention, and/or amelioration of gestational or fetal cardiovascular malconditions.

The foregoing and other features and advantages will become more apparent from the following detailed description of several embodiments, which proceeds with reference to the accompanying figures.

BRIEF DESCRIPTION OF THE FIGURES

FIG. 1 is a graph, depicting hemodynamic and metabolic measurements at baseline and during exercise in 18 subjects. FIG. 1A shows effects on each of the indicated values without inhibition of NO synthesis. FIG. 1B shows effects with inhibition of NO synthesis. Key: MAP—mean arterial pressure, mmHg; FBF—forearm blood flow, mL/min/100 mL; $O_2$ saturation, %; $pO_2$—venous oxyhemoglobin saturation, partial pressure of oxygen, mmHg; pH, units; *=p<0.05 vs. Baseline 1 or 2, respectively; **=p<0.01 vs. Baseline 1 or 2, respectively; †=p<0.05 vs. Baseline 1; ††=p<0.01 vs. Initial Exercise.

FIG. 2 is a graph, depicting effects of infusion of sodium nitrite in bicarbonate-buffered normal saline into the brachial arteries of 18 healthy subjects.

FIG. 3 is a series of graphs, illustrating the effects of infusion of low-dose sodium nitrite into the brachial arteries of 10 healthy subjects at baseline and during exercise, without and with inhibition of NO synthesis.

FIG. 4 is a pair of graphs, showing formation of NO-hemoglobin adducts.

FIG. 6 is a multipanel figure showing nitrite therapy in hepatic ischemia-reperfusion injury. FIG. 7 is a multipanel figure showing nitrite therapy in myocardial ischemia-reperfusion injury.

FIG. 8 is a series of graphs, illustrating blood and liver tissue levels of nitrite, RSNO and RxNO.

FIG. 9 is a multipanel figure, illustrating nitrite mediated hepatoprotection and the nitric oxide and heme oxygenase-1 signaling pathways.

FIG. 10 is a series of panels, showing the effects of nitrite anion inhalation in newborn hypoxic lambs (n=7) (FIG. 10A) on hemodynamic and metabolic measurements. After a hypoxic gas mixture (FiO$_2$=0.12) had been started at time 0, nitrite by aerosol reduced pulmonary artery pressure (PAP) from hypoxic levels by 63+/−3% (P<0.01 versus hypoxic baseline) with little change in mean arterial pressure (MAP), cardiac output, or methemoglobin levels, but a marked increase in exhaled NO (P<0.01 compared to baseline). FIG. 10B illustrates the effect of saline inhalation on pulmonary artery pressure in hypoxic lambs (n=7). FIG. 10C is a multipanel graph, showing maximal effects of nitrite nebulization as compared to saline nebulization on PAP, MAP, and exhaled NO (eNO). Data are mean±SEM.

FIG. 11 illustrates effects of nitrite anion inhalation in newborn lambs during stable, normoxic (SaO$_2$~99%) pulmonary hypertension induced by the infusion of an endoperoxide analog of thromboxane (U46619) (n=6). After infusion of U46619 was started at time 0, nitrite by aerosol reduced pulmonary artery pressure (PAP) from infusion baseline level by 23±6% (P<0.05 compared to infusion baseline) with no measurable change in mean arterial pressure (MAP) and with a moderate increase in exhaled NO (P<0.01 compared to baseline).

FIG. 12A compares the change in pulmonary arterial pressure (PAP), exhaled NO, and iron-nitrosyl-hemoglobin as measured by both chemiluminescence and electron paramagnetic resonance (EPR) after nitrite inhalation in animals with pulmonary hypertension induced with either hypoxia or infusion of the thromboxane analog U46199. Data for iron-nitrosyl-hemoglobin, measured by areas of output peaks after tri-iodide based reductive chemiluminescence (FIG. 12B) and by depth of peak at 3350 Gauss in electron paramagnetic resonance (EPR) (FIG. 12C; red line: drug induced, blue line: hypoxic) measured 20 minutes after nitrite inhalation was begun. FIG. 12D shows change in mean pulmonary artery pressure during hypoxia after inhalation of nebulized sodium nitrite was related to blood pH, with increased vasodilation associated with decreasing pH (r=0.57 P=0.055). Data are mean±SEM.

FIG. 13 is a multipanel figure, showing duration of effect of NO gas inhalation (n=7) (FIG. 13A) or nitrite nebulization (n=7) (FIG. 13B) on hemodynamic and metabolic measurements during hypoxic-induced pulmonary hypertension. Treatment with nitrite aerosol resulted in a rapid sustained reduction in hypoxic-induced pulmonary vasoconstriction and a graded increase in exhaled NO gas concentration with no change in mean arterial blood pressure. These results are contrasted to the rapid return in pulmonary artery pressure to hypoxic baseline after termination of inhaled NO gas (FIG. 13A). Methemoglobin (Met Hb) concentrations increased from 2.1±0.1% during baseline to 2.8±0.2% after nitrite nebulization (P<0.05). Note that the exhaled nitric oxide concentrations in FIG. 13A reach the limit of detection during administration of inhaled nitric oxide (20 ppm). FIG. 13C shows the change in pulmonary artery pressure (PAP) after aerosolization of nebulized nitrite and during the remaining hour of hypoxia following the termination of nitrite nebulization. FIG. 13D shows the arterial plasma nitrite concentrations during the course of the experiment. FIG. 13E shows the relationship between pulmonary artery pressure and exhaled NO after nitrite nebulization during hypoxia. Data are mean±SEM.

DETAILED DESCRIPTION OF THE DISCLOSURE

I. Abbreviations

Figures 2A, 2B:
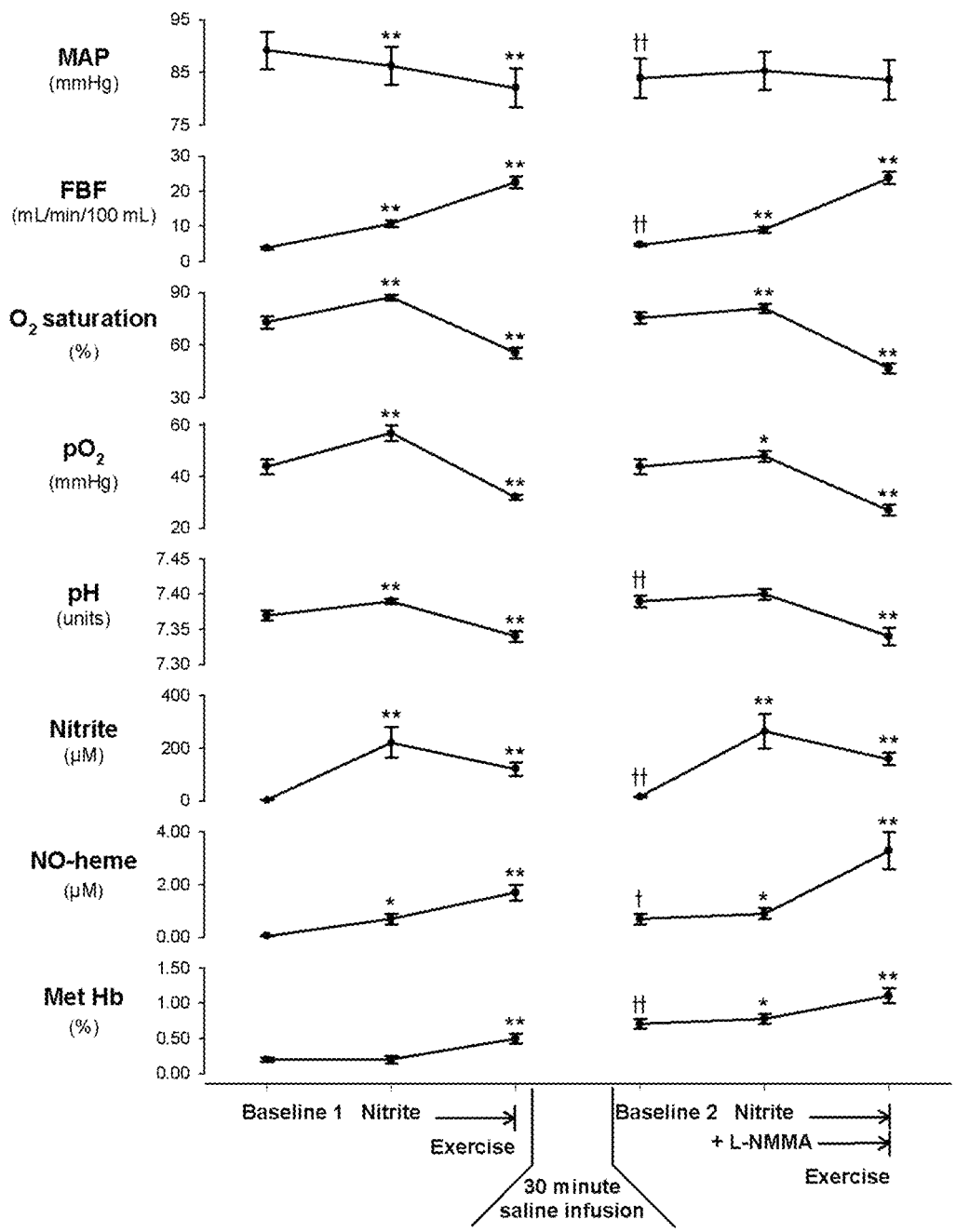
FIG. 2A shows effects on each of the indicated values without inhibition of NO synthesis.
FIG. 2B shows effects with inhibition of NO synthesis. Key as for FIG. 1, plus: Nitrite—venous nitrite, µM; NO-heme—venous iron-nitrosyl-hemoglobin, µM; and MetHb—venous methemoglobin, %; +=p<0.01 vs. Initial Exercise.

ANOVA analysis of variance carboxy-PTIO 2-(4-Carboxyphenyl)-4,4,5,5-tetramethylimidazoline-1-oxyl-3-oxide potassium salt
DCV delayed cerebral vasospasm
deoxy-RBC deoxygenated red blood cells
eNOS endothelial NO synthase
$FiO_2$ fractional concentration of inspired oxygen
FBF forearm blood flow
iNO inhaled nitric oxide
I/R ischemia-reperfusion
LCA main coronary artery
L-NMMA L-NG-monomethyl-arginine
LV left ventricle
NO nitric oxide
NOS nitric oxide synthase
MAP mean arterial pressure
MetHb methemoglobin
oxy-RBC oxygenated red blood cells
PBS phosphate buffered saline
$pO_2$ (or $Po_2$) partial oxygen pressure
SAH subarachnoid hemorrhage
S—NO 5-nitroso-hemoglobin

II. Terms

Unless otherwise noted, terms used herein should be accorded their standard definitions and conventional usage. For example, one of skill in the art can obtain definitions for the terms used herein in dictionaries and reference textbooks, for example: *Stedman's Medical Dictionary* (26th Ed., Williams and Wilkins, Editor M. Spraycar, 1995); *The New Oxford American Dictionary* (Oxford University Press, Eds E. Jewell and F. Abate, 2001); *Molecular Cloning: A Laboratory Manual* (Sambrook et al., 3rd Ed., Cold Spring Harbor Laboratory Press, 2001); and *Hawley's Condensed Chemical Dictionary*, 11th Ed. (Eds. N. I. Sax and R. J. Lewis, Sr., Van Nostrand Reinhold, New York, N.Y., 1987); *Molecular Biology and Biotechnology: a Comprehensive Desk Reference* (VCH Publishers, Inc., 1995 (ISBN 1-56081-569-8)).

In order to facilitate review of the various embodiments, the following explanations of specific terms are provided:

Animal: Living multi-cellular vertebrate organisms, a category that includes, for example, mammals and birds. The term mammal includes both human and non-human mammals.

Cerebral ischemia or ischemic stroke: A condition that occurs when an artery to or in the brain is partially or completely blocked such that the oxygen demand of the tissue exceeds the oxygen supplied. Deprived of oxygen and other nutrients following an ischemic stroke, the brain suffers damage as a result of the stroke.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Stroke can affect people of all ages, including children. Many people with ischemic strokes are older (60 or more years old), and the risk of stroke increases with older ages. At each age, stroke is more common in men than women, and it is more common among African-Americans than white Americans. Many people with stroke have other problems or conditions which put them at higher risk for stroke, such as high blood pressure (hypertension), heart disease, smoking, or diabetes.

Fetal: A term describing the time period in the latter part of pregnancy when organ systems are functional and blood flow patterns are established for central critical organs, such as the heart, brain and lungs.

Hypoxia: Deficiency in the amount of oxygen reaching body tissues.

Injectable composition: A pharmaceutically acceptable fluid composition comprising at least one active ingredient, for example, a salt of nitrite. The active ingredient is usually dissolved or suspended in a physiologically acceptable carrier, and the composition can additionally comprise minor amounts of one or more non-toxic auxiliary substances, such as emulsifying agents, preservatives, pH buffering agents and the like. Such injectable compositions that are useful for use with the compositions of this disclosure are conventional; appropriate formulations are well known in the art.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply.

Ischemia/reperfusion injury: In addition to the immediate injury that occurs during deprivation of blood flow, ischemic/ reperfusion injury involves tissue injury that occurs after blood flow is restored. Current understanding is that much of this injury is caused by chemical products and free radicals released into the ischemic tissues.

When a tissue is subjected to ischemia, a sequence of chemical events is initiated that may ultimately lead to cellular dysfunction and necrosis. If ischemia is ended by the restoration of blood flow, a second series of injurious events ensue producing additional injury. Thus, whenever there is a transient decrease or interruption of blood flow in a subject, the resultant injury involves two components—the direct injury occurring during the ischemic interval and the indirect or reperfusion injury that follows. When there is a long duration of ischemia, the direct ischemic damage, resulting from hypoxia, is predominant. For relatively short duration ischemia, the indirect or reperfusion mediated damage becomes increasingly important. In some instances, the injury produced by reperfusion can be more severe than the injury induced by ischemia per se. This pattern of relative contribution of injury from direct and indirect mechanisms has been shown to occur in all organs.

Methemoglobin: The oxidized form of hemoglobin in which the iron in the heme component has been oxidized from the ferrous (+2) to the ferric (+3) state. This renders the hemoglobin molecule incapable of effectively transporting and releasing oxygen to the tissues. Normally, there is about 1% of total hemoglobin in the methemoglobin form.

Methemoglobinemia: A condition in which a substantial portion of the hemoglobin in the blood of a subject is in the form of methemoglobin, making it unable to carry oxygen effectively to the tissues. Methemoglobinemia can be an inherited disorder, but it also can be acquired through exposure to chemicals such as nitrates (nitrate-contaminated water), aniline dyes, and potassium chlorate. It is not the presence of methemoglobin but the amount that is important in the clinical setting. The following provides rough indications of symptoms associated with different levels of methemoglobin in the blood: <1.7%, normal; 10-20%, mild cyanosis (substantially asymptomatic, though it can result in "chocolate brown" blood); 30-40%, headache, fatigue, tachycardia, weakness, dizziness; >35%, symptoms of hypoxia, such as dyspnea and lethargy; 50-60%, acidosis, arrhythmias, coma, convulsions, bradycardia, severe hypoxia, seizures; >70% usually results in death. Neonate: A term describing the human or animal organism in the time period after birth and extending until the adjustments from fetal to newborn life are completed.

Nitrite: The inorganic anion $^-NO_2$ or a salt of nitrous acid ($NO_2^-$). Nitrites are often highly soluble, and can be oxidized to form nitrates or reduced to form nitric oxide or ammonia. Nitrite may form salts with alkali metals, such as sodium ($NaNO_2$, also known as nitrous acid sodium salt), potassium and lithium, with alkali earth metals, such as calcium, magnesium and barium, with organic bases, such as amine bases, for example, dicyclohexylamine, pyridine, arginine, lysine and the like. Other nitrite salts may be formed from a variety of organic and inorganic bases. In particular embodiments, the nitrite is a salt of an anionic nitrite delivered with a cation, which cation is selected from sodium, potassium, and arginine. Many nitrite salts are commercially available, and/or readily produced using conventional techniques.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Peripheral Vascular Disease (PVD): A condition in which the arteries that carry blood to the arms or legs become narrowed or occluded. This interferes with the normal flow of blood, sometimes causing pain but often causing no readily detectable symptoms at all.

The most common cause of PVD is atherosclerosis, a gradual process in which cholesterol and scar tissue build up, forming plaques that occlude the blood vessels. In some cases, PVD may be caused by blood clots that lodge in the arteries and restrict blood flow. PVD affects about one in 20 people over the age of 50, or 8 million people in the United States. More than half the people with PVD experience leg pain, numbness or other symptoms, but many people dismiss these signs as "a normal part of aging" and do not seek medical help. The most common symptom of PVD is painful cramping in the leg or hip, particularly when walking. This symptom, also known as "claudication," occurs when there is not enough blood flowing to the leg muscles during exercise, such that ischemia occurs. The pain typically goes away when the muscles are rested.

Other symptoms may include numbness, tingling or weakness in the leg. In severe cases, people with PVD may experience a burning or aching pain in an extremity such as the foot or toes while resting, or may develop a sore on the leg or foot that does not heal. People with PVD also may experience a cooling or color change in the skin of the legs or feet, or loss of hair on the legs. In extreme cases, untreated PVD can lead to gangrene, a serious condition that may require amputation of a leg, foot or toes. People with PVD are also at higher risk for heart disease and stroke.

A "pharmaceutical agent" or "drug" refers to a chemical compound or other composition capable of inducing a desired therapeutic or prophylactic effect when properly administered to a subject.

Placenta: A vascular organ that provides for metabolic exchange between mother and fetus in mammals. It delivers oxygen, water, and nutrients to the fetus from the mother's blood and secretes the hormones necessary for successful pregnancy. In addition, it carries wastes away from the fetus to be processed in the mother's body.

Preeclampsia: A disease of unknown cause in pregnant women, characterized by hypertension, abnormal blood vessels in the placenta, and protein in the urine. It often but not always occurs with gestational diabetes or in diabetics. Additional symptoms may include water retention, leading to swelling in the face, hands and feet, and greater weight gain. Also called toxemia. Preeclampsia can lead to eclampsia if not treated. The only known cure for preeclampsia is delivery of the child.

Preventing or treating a disease: "Preventing" a disease refers to inhibiting the full development of a disease. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified nitrite salt preparation is one in which the specified nitrite salt is more enriched than it is in its generative environment, for instance within a biochemical reaction chamber. Preferably, a preparation of a specified nitrite salt is purified such that the salt represents at least 50% of the total nitrite content of the preparation. In some embodiments, a purified preparation contains at least 60%, at least 70%, at least 80%, at least 85%, at least 90%, at least 95% or more of the specified compound, such as a particular nitrite salt.

Reperfusion: Restoration of blood supply to tissue that is ischemic, due to decrease in blood supply. Reperfusion is a procedure for treating infarction or other ischemia, by enabling viable ischemic tissue to recover, thus limiting further necrosis. However, it is thought that reperfusion can itself further damage the ischemic tissue, causing reperfusion injury.

Subject: Living multi-cellular organisms, including vertebrate organisms, a category that includes both human and non-human mammals.

Therapeutic: A generic term that includes both diagnosis and treatment.

Therapeutically effective amount of [a vasodilator]: A quantity of compound, such as a nitrite salt, sufficient to achieve a desired effect in a subject being treated. For instance, this can be the amount necessary to treat or ameliorate relatively high blood pressure, or to measurably decrease blood pressure over a period of time, or to measurably inhibit an increase in blood pressure, in a subject.

An effective amount of a vasodilator may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a pharmaceutically-acceptable salt of nitrite) in blood (in vivo) or a buffer (in vitro) that produces an effect.

By way of example, as described herein it is now shown that pharmaceutically-acceptable salts of nitrite (such as sodium nitrite) are effective as vasodilators at calculated dosages of about 0.6 to about 200 µM final concentration of nitrite in the circulating blood of a subject, which level can be determined empirically or through calculations. Specific levels can be reached, for instance, by providing less than about 200 mg or less nitrite in a single dose, or a dose provided over a period of time (e.g., by infusion or inhalation). For instance, other dosages may be 150 mg, 100 mg, 75 mg, 50 mg or less. Specific example dosages of nitrite salts are provided herein, though the examples are not intended to be limiting. Exact dosage amounts will vary by the size of the subject being treated, the duration of the treatment, the mode of administration, and so forth.

Particularly beneficial therapeutically effective amounts of a vasodilator, such as a pharmaceutically-acceptable nitrite salt (e.g., sodium nitrite), are those that are effective for vasodilation or increasing blood flow, but not so high that a significant or toxic level of methemoglobin is produced in the subject to which the vasodilator is administered. In specific embodiments, for instance, no more than about 25% methemoglobin is produced in the subject. More preferably, no more than 20%, no more than 15%, no more than 10%, no more than 8% or less methemoglobin is produced, for instance as little as 5% or 3% or less, in response to treatment with the vasodilator.

The compounds discussed herein have equal application in medical and veterinary settings. Therefore, the general term "subject being treated" is understood to include all animals (for example, humans, apes, laboratory animals, companion animals, etc.) that are or may be suffering from an aberration in blood pressure, such as hypertension.

Vasoconstriction. The diminution of the caliber or cross-sectional area of a blood vessel, for instance constriction of arterioles leading to decreased blood flow to a body part. This can be caused by a specific vasoconstrictor, an agent (for instance a chemical or biochemical compound) that causes, directly or indirectly, constriction of blood vessels. Such an agent can also be referred to as a vasohypertonic agent, and is said to have vasoconstrictive activity. A representative category of vasoconstrictors is the vasopressor (from the term pressor, tending to increase blood pressure), which term is generally used to refer to an agent that stimulates contraction of the muscular tissue of the capillaries and arteries.

Vasoconstriction also can be due to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus, among others.

Vasodilation. A state of increased caliber of the blood vessels, or the act of dilation of a blood vessel, for instance dilation of arterioles leading to increased blood flow to a body part. This can be caused by a specific vasodilator, an agent (for instance, a chemical or biochemical compound) that causes, directly or indirectly, dilation of blood vessels. Such an agent can also be referred to as a vasohypotonic agent, and is said to have vasodilative activity.

Vasospasm: Another cause of stroke occurs secondary to spasm of blood vessels supplying the brain. This type of stroke typically follows a subarachnoid aneurismal hemorrhage with a delayed development of vasospasm within 2-3 weeks of the bleeding event. A similar type of stroke may complicate sickle cell disease.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

It has been surprisingly discovered that administration of pharmaceutically-acceptable salts of nitrite is useful in the regulation of the cardiovascular system. It has also been surprisingly discovered that nitrite is reduced to nitric oxide in vivo, and that the nitric oxide produced thereby is an effective vasodilator. These effects surprisingly occur at doses that do not produce clinically significant methemoglobinemia. These discoveries now enable methods to prevent and treat conditions associated with the cardiovascular system, for example, high blood pressure, pulmonary hypertension, cerebral vasospasm and tissue ischemia-reperfusion injury. These discoveries also provide methods to increase blood flow to tissues, for example, to tissues in regions of low oxygen tension. It is particularly surprising that the nitrite does not need to be applied in an acidified condition in order for it to be effective in regulating the cardiovascular system, and more particularly to act as a vasodilator in vivo.

Accordingly, the present disclosure provides in one embodiment a method for decreasing a subject's blood pressure, including administering to the subject sodium nitrite at about 36 moles per minute or less into the forearm brachial artery or intravenously.

The present disclosure also provides a method for decreasing a subject's blood pressure, including administering to the subject an effective amount of pharmaceutically-acceptable nitrite so as to decrease (or lower, or reduce) the subject's blood pressure. Another embodiment is a method for treating a subject having a condition associated with elevated blood pressure, including administering to the subject an effective amount of pharmaceutically-acceptable nitrite so as to treat at least one vascular complication associated with the elevated blood pressure. Also provided is a method for treating a subject having a hemolytic condition, including administering to the subject an effective amount of pharmaceutically-acceptable nitrite so as to treat at least one vascular complication associated with the hemolytic condition.

The present disclosure additionally provides a method for increasing blood flow to a tissue of a subject, including administering to the subject an effective amount of pharmaceutically-acceptable nitrite so as to increase blood flow to a tissue of the subject. Also provided is a method for producing an amount of NO in a subject effective the decrease the subject's blood pressure, including administering a pharmaceutically-acceptable nitrite to the subject.

The present disclosure further provides a pharmaceutical composition comprising an effective amount of a pharmaceutically-acceptable nitrite and a carrier.

In some embodiments, the vascular complication is one or more selected from the group consisting of pulmonary hypertension (including neonatal pulmonary hypertension, primary pulmonary hypertension, and secondary pulmonary hypertension), systemic hypertension, cutaneous ulceration, acute renal failure, chronic renal failure, intravascular thrombosis, an ischemic central nervous system event, and death.

In some embodiments, nitrite is administered to neonates to treat pulmonary hypertension.

In some embodiments, the hemolytic condition includes one or more selected from: sickle cell anemia, thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HUS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe *haemophilus influenzae* type b infection, extensive burns, transfusion reaction, rhabdomyolysis (myoglobinemia), transfusion of aged blood, cardiopulomonary bypass, and hemodialysis.

In some embodiments, the decreased blood flow to the tissue is caused directly or indirectly by at least one of the following conditions: sickle cell anemia, thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HUS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe *haemophilus influenzae* type b infection, extensive burns, transfusion reaction, rhabdomyolysis (myoglobinemia), transfusion of aged blood, transfusion of hemoglobin, transfusion of red blood cells, cardiopulmonary bypass, coronary disease, cardiac ischemia syndrome, angina, iatrogenic hemolysis, angioplasty, myocardial ischemia, tissue ischemia, hemolysis caused by intravascular devices, hemodialysis, pulmonary hypertension, systemic hypertension, cutaneous ulceration, acute renal failure, chronic renal failure, intravascular thrombosis, and an ischemic central nervous system event.

In some embodiments, the tissue is an ischemic tissue. In some embodiments, the administration is parenteral, oral, bucal, rectal, ex vivo, or intraocular. In some embodiments, the administration is peritoneal, intravenous, intraarterial, subcutaneous, inhaled, or intramuscular. In some embodiments, the nitrite is administered to the subject in an environment of low oxygen tension, or acts in an area of the subject's body that displays relatively low oxygen tension. In some embodiments, the nitrite is administered as a pharmaceutically-acceptable salt of nitrite, such as, for instance, sodium nitrite, potassium nitrite, or arginine nitrite. In some embodiments, the nitrite is administered in combination with at least one additional active agent. It is specifically contemplated that, in certain embodiments, that the subject is a mammal, for instance, a human.

The disclosure further provides a method for treating a subject having a condition associated with elevated blood pressure in the lungs, e.g. pulmonary hypertension, including administering to the subject an effective amount of pharmaceutically-acceptable nitrite. In some embodiments, this includes treating a subject having neonatal pulmonary hypertension. In some embodiments, this includes treating a subject having primary and/or secondary pulmonary hypertension. In some embodiments for treating subjects having a condition associated with elevated blood pressure in the lungs, the nitrite is nebulized.

The disclosure also provides suggestions for a means of treating hypertension and/or preeclampsia in pregnant women. Such therapy would include action of nitrites on spastic and diseased blood vessels within the placenta.

The disclosure also provides suggestions for treating, in utero, fetuses with cardiovascular anomalies, hypertension, and/or misdirected blood flow. In such approaches, nitrite may be administered by introduction into the amniotic cavity either directly or by osmotic minipumps, the latter to achieve sustained release throughout days and weeks of pregnancy.

Thus, there is provided herein a method for inducing vasodilation and/or increasing blood flow in a subject, which method involves administering to the subject an effective amount of a pharmaceutically-acceptable salt of nitrite for a sufficient period of time to induce vasodilation and/or increase blood flow in the subject. Non-limiting examples of pharmaceutically acceptable salts of nitrite include sodium nitrite, potassium nitrite, and arginine nitrite. In examples of the provided methods, the pharmaceutically-acceptable salt of nitrite reacts in the presence of hemoglobin in the subject to release nitric oxide.

It is a specific advantage of methods provided herein that the effective amount of the pharmaceutically-acceptable salt of nitrite administered to the subject does not induce toxic levels of methemoglobin, and in many embodiments does not induced formation of clinically significant amounts of methemoglobin in the subject. Therefore, contemplated herein are methods in which the effective amount of the pharmaceutically-acceptable salt of nitrite, when administered to the subject, induces production in the subject of no more than about 25% methemoglobin; no more than about 20% methemoglobin; no more than about 10% methemoglobin; no more than about 8% methemoglobin; or no more than about 5% methemoglobin. Beneficially, examples of the provided methods induce production of even less than 5% methemoglobin, for instance no more than about 3% methemoglobin, less than 3%, less than 2%, or even less than 1%.

In one specific example of a method for inducing vasodilation and/or increasing blood flow in a subject, sodium nitrite is administered by injection at about 36 moles per minute for at least five minutes into the forearm brachial artery of the subject.

The effective amount of the pharmaceutically-acceptable salt of nitrite is administered, in various embodiments, to a circulating concentration in the subject of about 0.6 to 240 µM, measured locally to the site of administration or generally in the subject. It is noted that the local level of nitrite is expected to be higher than the general circulating level particularly in short delivery regimens; in long term delivery regimens, such as delivery using a pump or injector, or by inhalation, the system-wide or general nitrite level is expected to near the level measured near the administration site.

Administration of the pharmaceutically-acceptable nitrite can be, for instance, parenteral, oral, bucal, rectal, ex vivo, or intraocular in certain embodiments. In various embodiments, it is also contemplated that the administration of the nitrite can be peritoneal, intravenous, intraarterial, subcutaneous, inhaled, intramuscular, or into a cardiopulmonary bypass circuit. Combinations of two or more routes of administration are also contemplated.

In various embodiments of the method for inducing vasodilation and/or increasing blood flow in a subject, the subject is a mammal. It is particularly contemplated that the subject can be a human.

Combination therapy methods are contemplated, wherein the nitrite is administered in combination with at least one additional agent. By way of non-limiting examples, the additional agent is one or more selected from the list consisting of penicillin, hydroxyurea, butyrate, clotrimazole, arginine, or a phosphodiesterase inhibitor (such as sildenafil).

In another embodiment of the method for inducing vasodilation and/or increasing blood flow in a subject, the subject has elevated blood pressure, and the method is a method for treating at least one vascular complication associated with the elevated blood pressure, or the subject has a hemolytic condition, and the method is a method for treating at least one vascular complication associated with the hemolytic condition. Optionally, the subject may have both elevated blood pressure and a hemolytic condition.

In examples of the methods provided herein, the at least one vascular complication is one or more selected from the group consisting of pulmonary hypertension, systemic hypertension, peripheral vascular disease, trauma, cardiac arrest, general surgery, organ transplantation, cutaneous ulceration, acute renal failure, chronic renal failure, intravascular thrombosis, angina, an ischemia-reperfusion event, an ischemic central nervous system event, and death.

In examples of the methods in which the subject has a hemolytic condition, the hemolytic condition is one or more selected from the group consisting of sickle cell anemia, thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HUS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe *haemophilus influenzae* type b infection, extensive burns, transfusion reaction, rhabdomyolysis (myoglobinemia), transfusion of aged blood, transfusion of hemoglobin, transfusion of red blood cells, cardiopulmonary bypass, coronary disease, cardiac ischemia syndrome, angina, iatrogenic hemolysis, angioplasty, myocardial ischemia, tissue ischemia, hemolysis caused by intravascular devices, and hemodialysis.

In yet another embodiment of the method for inducing vasodilation and/or increasing blood flow in a subject, the subject has a condition associated with decreased blood flow to a tissue, and the method is a method to increase blood flow to the tissue of the subject. For instance, in examples of this method, the decreased blood flow to the tissue is caused directly or indirectly by at least one condition selected from the group consisting of: sickle cell anemia, thalassemia, hemoglobin C disease, hemoglobin SC disease, sickle thalassemia, hereditary spherocytosis, hereditary elliptocytosis, hereditary ovalcytosis, glucose-6-phosphate deficiency and other red blood cell enzyme deficiencies, paroxysmal nocturnal hemoglobinuria (PNH), paroxysmal cold hemoglobinuria (PCH), thrombotic thrombocytopenic purpura/hemolytic uremic syndrome (TTP/HUS), idiopathic autoimmune hemolytic anemia, drug-induced immune hemolytic anemia, secondary immune hemolytic anemia, non-immune hemolytic anemia caused by chemical or physical agents, malaria, falciparum malaria, bartonellosis, babesiosis, clostridial infection, severe *haemophilus influenzae* type b infection, extensive burns, transfusion reaction, rhabdomyolysis (myoglobinemia), transfusion of aged blood, transfusion of hemoglobin, transfusion of red blood cells, cardiopulmonary bypass, coronary disease, cardiac ischemia syndrome, angina, iatrogenic hemolysis, angioplasty, myocardial ischemia, tissue ischemia, hemolysis caused by intravascular devices, hemodialysis, pulmonary hypertension, systemic hypertension, cutaneous ulceration, acute renal failure, chronic renal failure, intravascular thrombosis, and an ischemic central nervous system event.

It is specifically contemplated in examples of this method that the tissue is an ischemic tissue, for instance one or more tissues selected from the group consisting of neuronal tissue, bowel tissue, intestinal tissue, limb tissue, lung tissue, central nervous tissue, or cardiac tissue.

Also provided are methods for inducing vasodilation and/or increasing blood flow in a subject having elevated blood pressure, wherein the elevated blood pressure comprises elevated blood pressure in the lungs. By way of example, it is contemplated that such subject in some instances has neonatal pulmonary hypertension, or primary and/or secondary pulmonary hypertension.

In examples of embodiments where the elevated blood pressure, or need for increased blood flow, in the subject comprises elevated blood pressure or need for increased blood flow in the lungs, the pharmaceutically-acceptable salt of nitrite is nebulized.

By way of example, in various embodiments the pharmaceutically-acceptable salt of nitrite is administered to a circulating concentration in the subject of no more than about 100 $\mu M$; no more than about 50 $\mu M$; no more than about 20 $\mu M$; no more than about 16 $\mu M$; or less than about 16 $\mu M$.

Another embodiment is a method for treating or ameliorating a condition selected from: (a) hepatic or cardiac or brain ischemia-reperfusion injury; (b) pulmonary hypertension; or (c) cerebral artery vasospasm, in a subject by decreasing blood pressure and/or increasing vasodilation in the subject, the method comprising administering sodium nitrite to the subject to decrease the blood pressure and/or increase vasodilation in the subject, thereby treating or ameliorating the condition.

In specific examples of this embodiment, the method is a method for treating or ameliorating hepatic or cardiac or brain ischemia-reperfusion injury. Optionally, the sodium nitrite is administered to the subject via injection, for instance, intravenous injection. In certain examples, the sodium nitrite is administered to a circulating concentration of about 0.6 to 240 $\mu M$.

In other specific examples of this embodiment, the method is a method for treating or ameliorating pulmonary hypertension, such as for instance neonatal pulmonary hypertension. Beneficially, in such methods the sodium nitrite can be administered to the subject by inhalation, for instance it can be nebulized. Optionally, in any of these methods, the sodium nitrite is administered at a rate of 270 $\mu mol/minute$, though other rates and circulating levels are contemplated.

Also provided in other examples of this embodiment are methods for treating or ameliorating cerebral artery vasospasm. Optionally, the sodium nitrite is administered to the subject via injection, for instance, intravenous injection. In examples of such methods, the sodium nitrite is administered at a rate of about 45 to 60 mg/kg.

In examples of the described methods, optionally the sodium nitrite can be administered in combination with at least one additional agent.

In any of the described methods, it is contemplated that the subject can be a mammal, such as for instance a human.

IV. Sodium Nitrite as an In Vivo Vasodilator

Nitrite anions are present in concentrations of about 150-1000 nM in the plasma and about 10 $\mu M$ in aortic tissue. This represents the largest vascular storage pool of nitric oxide (NO), provided physiological mechanisms exist to reduce nitrite to NO. The vasodilator properties of nitrite in the human forearm and the mechanisms extant for its bioactivation have been investigated and results are reported herein. Sodium nitrite was infused at about 36 $\mu moles$ per minute into the forearm brachial artery of 18 normal volunteers, resulting in a regional nitrite concentration of about 222 $\mu M$ and an immediate about 175% increase in resting forearm blood flow. Increased blood flow was observed at rest, during NO synthase inhibition and with exercise, and resulted in increased tissue perfusion, as demonstrated by increases in venous hemoglobin-oxygen saturation, partial pressure of oxygen, and pH. Systemic concentrations of nitrite increased to about 16 $\mu M$ and significantly reduced mean arterial blood pressure. In an additional six subjects, the dose of nitrite was reduced about 2-logs and infused at 360 nmoles per minute, resulting in a forearm nitrite concentration of about 2 $\mu M$ and an about 22% increase in blood flow.

Nitrite infusions were associated with the formation of erythrocyte iron-nitrosyl-hemoglobin, and to a lesser extent, S-nitroso-hemoglobin across the forearm vasculature. The formation of NO-modified hemoglobin appears to result from the nitrite reductase activity of deoxyhemoglobin, linking tissue hypoxia and nitrite bioactivation.

These results indicate that physiological levels of blood and tissue nitrite represent a major bioavailable pool of NO that contributes to vaso-regulation and provides a mechanism for hypoxic vasodilation via reaction of vascular nitrite with deoxygenated heme proteins. Substantial blood flow effects of nitrite infusion into the brachial artery of normal human subjects results from forearm nitrite concentrations as low as about 0.9 $\mu M$.

By way of example, as described herein it is now shown that pharmaceutically-acceptable salts of nitrite (such as sodium nitrite) are effective as vasodilators at calculated dosages of about 0.6 to about 200 $\mu M$ final concentration of nitrite in the circulating blood of a subject. Specific circulating levels (locally or generally in the subject) can be reached, for instance, by providing less than about 200 mg or less nitrite in a single dose, or a dose provided over a period of time (e.g., by infusion or inhalation). For instance, other dosages may be 150 mg, 100 mg, 75 mg, 50 mg or less. Specific example dosages of nitrite salts are provided herein, though the examples are not intended to be limiting. Exact dosage amounts will vary by the size of the subject being treated, the duration of the treatment, the mode of administration, and so forth.

Infusion rates can be calculated, for any given desired target circulating concentration, by using the following equation:

$$\text{Infusion rate } (\mu M/min) = \text{target concentration } (\mu mol/L, \text{ or } \mu M) \times \text{Clearance } (L/min)$$

where Clearance (L/min)=0.015922087×weight of the subject (kg) ↑0.8354
The rate of clearance has been calculated based on empirical results, including those reported herein.

By way of example, when sodium nitrite is infused into a human forearm at 36 micromoles ($\mu Mol$) per minute, the concentration measured coming out of forearm is about 222 µM and about 16 µM in whole body, after 15 minutes infusion. The background level of circulating nitrite in mammals is low, around 150-500 nanoM.

Particularly beneficial therapeutically effective amounts of a vasodilator, such as a pharmaceutically-acceptable nitrite salt (e.g., sodium nitrite), are those that are effective for vasodilation or increasing blood flow, but not so high that a significant or toxic level of methemoglobin is produced in the subject to which the vasodilator is administered. In specific embodiments, for instance, no more than about 25% methemoglobin is produced in the subject. More preferably, no more than 20%, no more than 15%, no more than 10%, no more than 8% or less methemoglobin is produced, for instance as little as 5% or 3% or less, in response to treatment with the vasodilator.

By way of specific example, nitrite can be infused at concentrations less than 40 µMol per minute intravenously or intraarterially, or given by mouth. Importantly, doses used are less than those used for the treatment of cyanide poisoning, which are designed to induce clinically significant methemoglobinemia. Surprisingly, the doses described herein for the treatment/prevention of cardiovascular conditions produce significant and beneficial clinical effects without clinically significant methemoglobin production.

Relatively complex inorganic/organic nitrite compounds and nitrate compounds have been utilized clinically to treat disorders, including angina. These drugs (e.g., glyceryl trinitrate) suffer from tolerance (requiring increases in dosage in order to maintain the same effect), however, and are distinct vasodilators compared to nitrite. For example, the former require cellular thiols for metabolism, whereas nitrite or the nitrite salts discussed herein (e.g., sodium nitrite) do not.

V. A Mechanism of Iron-Nitrosyl- and S-Nitroso-Hemoglobin Formation In Vivo

Figure 4A:
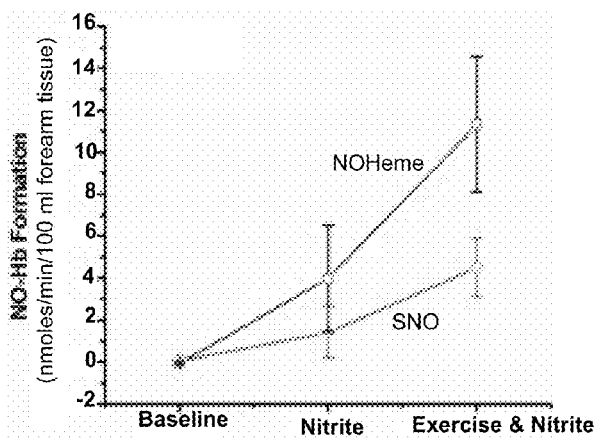
FIG. 4A shows formation of iron-nitrosyl-hemoglobin and S-nitroso-hemoglobin, comparing baseline, with nitrite infusion, and nitrite infusion with exercise.
Figure 4B:
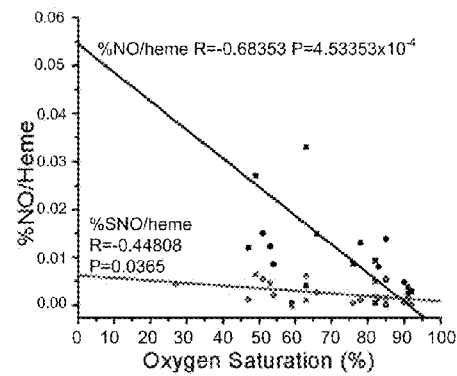
FIG. 4B compares formation of NO-hemoglobin adducts with hemoglobin-oxygen saturation in the human circulation, during nitrite infusion.

The levels of both iron-nitrosyl- and S-nitroso-hemoglobin formed in vivo in this study are striking. During a transit time of less than 10 seconds through the forearm circulation during exercise, infused nitrite (200 µM regional concentration) produced approximately 750 nM iron-nitrosyl-hemoglobin and 200 nM SNO-Hb. The formation of both NO-hemoglobin adducts was inversely correlated with hemoglobin-oxygen saturation, which fell during exercise stress, measured from the antecubital vein by co-oximetry (for iron-nitrosyl-hemoglobin r=−0.7, P<0.0001; for S-nitroso-hemoglobin r=−0.45, P=0.04; FIG. 4B). Addition of 200 µM nitrite to whole blood at different oxygen tensions (0-100%) recapitulated the in vivo data with increasing concentrations of iron-nitrosyl hemoglobin being formed at lower oxygen tensions (for iron-nitrosyl-hemoglobin r=−0.968, P<0.0001; for S-nitroso-hemoglobin r=−0.45, P=0.07), strongly suggesting that the NO and SNO formation was dependent on the reaction of nitrite with deoxyhemoglobin.

These data are consistent with the reaction of nitrite with deoxyhemoglobin to form NO and iron-nitrosyl-hemoglobin (Doyle et al., *J Biol Chem*, 256, 12393-12398, 1981). Nitrite is first reduced to form NO and methemoglobin with a rate constant of 2.9 $M^{-1}sec^{-1}$ (measured at 25° C., pH 7.0). This reaction will be pseudo-first order, governed by the amounts (20 mM) of intra-erythrocytic hemoglobin, and limited by the rate of nitrite uptake by the erythrocyte membrane. NO then binds to deoxyhemoglobin to form iron-nitrosyl-hemoglobin, escapes the erythrocyte, or reacts with other higher oxides, such as $NO_2$, to form $N_2O_3$ and S-nitroso-hemoglobin. Equation series 1

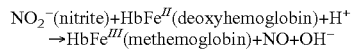
$NO_2^-$(nitrite)+$HbFe^{II}$(deoxyhemoglobin)+$H^+$
→$HbFe^{III}$(methemoglobin)+NO+$OH^-$

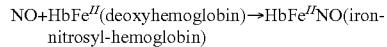
NO+$HbFe^{II}$(deoxyhemoglobin)→$HbFe^{II}$NO(iron-nitrosyl-hemoglobin)

The formation of significant amounts of S-nitroso-hemoglobin in vivo during nitrite infusion was also observed. Luschinger and colleagues (*Proc Natl Acad Sci USA*, 100, 461-6, 2003) recently proposed that nitrite reacts with deoxyhemoglobin to make iron-nitrosyl-hemoglobin, with subsequent "transfer" of the NO to the cysteine 93 to form S-nitroso-hemoglobin mediated by reoxygenation and quaternary T to R transition of hemoglobin. However, a direct transfer of NO from the heme to the thiol requires NO oxidation to NO+ and such "cycling" has not been reproduced by other research groups. Fernandez and colleagues have recently suggested that nitrite catalyzes the reductive nitrosylation of methemoglobin by NO, a process that generates the intermediate nitrosating species dinitrogen teraoxide ($N_2O_3$) (*Inorg Chem*, 42, 2-4, 2003). However, nitrite reactions with hemoglobin provide ideal conditions for NO and S-nitrosothiol generation along the oxygen gradient as nitrite reacts with deoxyhemoglobin to form NO and with oxyhemoglobin to form nitrogen dioxide ($NO_2$) radical. $NO_2$ participates in radical-radical reactions (k=$10^9$ $M^{-1}sec^{-1}$) with NO to form $N_2O_3$ and S-nitrosothiol. Additional chemistry of nitrite with hemoglobin produces reactive oxygen metabolites (such as superoxide and hydrogen peroxide; Watanabe et al., *Acta Med Okayama* 35, 173-8, 1981; Kosaka et al., *Biochim Biophys Acta* 702, 237-41, 1982; and Kosaka et al., *Environ Health Perspect* 73, 147-51, 1987). Chemistry involving such NO radical-oxygen radical reactions provides competitive pathways for S-nitrosothiol formation in the presence of high affinity NO sinks, such as hemoglobin.

VI. Physiological Considerations

The last decade has seen an increase in the understanding of the critical role nitric oxide (NO) plays in vascular homeostasis. The balance between production of NO and scavenging of NO determines NO bioavailability, and this balance is carefully maintained in normal physiology. The homeostatic, vasoregulatory system is apparently fine-tuned to scavenge excess NO to limit gross endocrine actions while allowing for sufficient local NO necessary for regional tonic vasodilation. However, rapid NO scavenging by cell-free hemoglobin disrupts this balance (Reiter et al., *Nat Med* 8, 1383-1389, 2002). Under normal physiological conditions, hemoglobin is rapidly and effectively cleared by the hemoglobin scavenger system. However, chronic hemolytic conditions, such as sickle cell disease, result in the daily release of substantial quantities of hemoglobin into the vasculature, suggesting that cell-free hemoglobin may have major systemic effects on NO bioavailability. A current focus of research attempts to explain and treat the vascular complications common to many chronic hemolytic conditions, such as pulmonary hypertension, cutaneous ulceration and acute and chronic renal failure. Similarly, a number of clinical diseases and therapies such as acute hemolytic crises, hemolysis during cardiopulmonary bypass procedures, transfusion of aged blood, and myoglobinuria following muscle infarction are often complicated by acute pulmonary and systemic hypertension, acute renal failure, intravascular thrombosis, ischemic central nervous system events and/or death.

It is demonstrated herein that nitrite produces vasodilation in humans associated with nitrite reduction to NO by deoxyhemoglobin. Remarkably, systemic levels of 16 µM resulted in systemic vasodilation and decreased blood pressure, and regional forearm levels of only 1-2 µM significantly increased blood flow at rest and with exercise stress. Furthermore, conversion of nitrite to NO and S-nitrosothiol was mediated by reaction with deoxyhemoglobin, providing a mechanism for hypoxia-regulated catalytic NO production by the erythrocyte or endothelial/tissue heme proteins. While high concentrations of hemoglobin in red cells, coupled with the near diffusion-limited reaction rates ($\sim 10^7$ $M^{-1}s^{-1}$) of NO with hemoglobin, seem to prohibit NO from being exported from the red blood cell, the data presented herein argue to the contrary. While not intending to be limiting, perhaps unique characteristics of the erythrocyte membrane, with a submembrane protein and methemoglobin-rich microenvironment, and the relative lipophilic nature of NO, allow compartmentalized NO production at the red blood cell membrane. This, coupled with the small yields of NO necessary for vasodilation, could account for the export of NO despite these kinetic constraints. It is further proposed that in vivo chemistry for the conversion of nitrite to NO and S-nitrosothiol by reaction with deoxyhemoglobin and methemoglobin provides a mechanism for hypoxia-regulated catalytic NO production by the erythrocyte or endothelial tissue heme proteins.

Three factors uniquely position nitrite, rather than S-nitrosothiol, as the major vascular storage pool of NO: 1) Nitrite is present in substantial concentrations in plasma, erythrocytes and in tissues (Rodriguez et al., *Proc Natl Acad Sci USA* 100:336-341, 2003). 2) Nitrite is relatively stable, because it is not readily reduced by intracellular reductants, as are S-nitrosothiols (Gladwin et al., *J Biol Chem* 21:21, 2002) and its reaction rate with heme proteins is 10,000 times less than that of authentic NO. 3) Nitrite is only converted to NO by reaction with deoxyhemoglobin (or presumably deoxy-myoglobin, -cytoglobin, and -neuroglobin) and its "leaving group" is the met(ferric)heme protein which will not scavenge and inactivate NO (Doyle et al., *J Biol Chem* 256:12393-12398, 1981). Therefore, this pool provides the ideal substrate for NO generation during hypoxia, providing a novel mechanism for hypoxic vasodilation.

Because a deoxyhemoglobin-nitrite reductase system would result in NO formation in deoxygenating blood, such a system links hemoglobin oxygenation status to NO generation, the principle previously ascribed to S-nitroso-hemoglobin (Jia et al., *Nature* 380:221-226, 1996). Hemoglobin possesses anionic binding cavities that retain nitrite (Gladwin et al., *J Biol Chem* 21:21, 2002) and nitrite is taken up by erythrocytes through the anion exchange protein (AE1 or Band 3) or through the membrane as nitrous acid (a pH dependent process that accelerates nitrite uptake during tissue hypoxia (Shingles et al., *J Bioenerg Biomembr* 29:611-616, 1997; May et al., *Am I Physiol Cell Physiol* 279:C1946-1954, 2000). Such nitrite would provide a steady source of NO, $NO_2$ and 5-nitrosothiol generation that would occur preferentially in hypoxic vascular territories. Because the AE1 protein binds both deoxyhemoglobin and methemoglobin and may channel nitrite, AE1 could serve to localize catalytic NO and 5-nitrosothiol generation at the erythrocyte membrane, where the relatively lipophilic NO, $NO_2$ and $N_2O_3$ could react in the vicinal lipid bilayer (FIG. 5). The erythrocyte membrane is lined by an unstirred outer diffusion barrier and an inner methemoglobin rich protein matrix that might further promote such NO and $NO_2$ chemistry (Coin et al., *J Biol Chem* 254:1178-1190, 1979; Liu et al., *J Biol Chem* 273:18709-18713, 1998; Han et al., *Proc Natl Acad Sci USA* 99:7763-7768, 2002).

This model is consistent with the in vitro observations of Pawloski and colleagues (Pawloski et al., *Nature* 409:622-626, 2001) showing that 5-nitrosation of hemoglobin and AE1 occurs in the erythrocyte membrane after treatment of deoxygenated red blood cells with NO solutions (which contain significant-more than 50 µM-contaminating nitrite; Fernandez, et al. *Inorg Chem* 42:2-4, 2003). Further, $N_2O_3$ generated at the membrane could directly nitrosate the abundant intra-erythrocytic glutathione, eliminating the requirement of transnitrosation reactions with 5-nitroso-hemoglobin and thus facilitating rapid export of low molecular weight 5-nitrosothiol by simple diffusion across the erythrocyte membrane (FIG. 5). A nitrite-hemoglobin chemistry supports a role for the red cell in oxygen-dependent NO homeostasis and provides a mechanism for the observations of multiple research groups that red blood cells and plasma "loaded" with NO, by exposure to NO in high concentration in solution or to NO gas or donors (in equilibria with high concentrations of nitrite), can export NO and induce vasodilation in vitro and in vivo (Rassaf et al., *J Clin Invest* 109:1241-1248, 2002; Fox-Robichaud et al., *J Glitz Invest* 101:2497-2505, 1998; McMahon et al., *Nat Med* 3:3, 2002; Cannon et al., *J Clin Invest* 108:279-287, 2001; Gladwin et al., *J Biol Chem* 21:21, 2002; Gladwin et al., *Circulation* 107:271-278, 2003; Schechter et al., *N Engl J Med* 348:1483-1485, 2003).

In addition to the reaction of nitrite with deoxyhemoglobin, reactions with deoxy-myoglobin, -cytoglobin and -neuroglobin or with other endothelial cell heme proteins may also be important. Such chemistry would occur between tissue nitrite and deoxy-myoglobin in vascular and skeletal muscle, thus contributing to hypoxic vasodilation and hypoxic potentiation of NO donors. The $P_{50}$ of these globin monomers is approximately 3-5 mm Hg, placing their equilibrium deoxygenation point in the range of tissue $pO_2$ (0-10 mm Hg) during metabolic stress, such as exercise. Such a low oxygen tension reduces oxygen availability as substrate for NO synthesis, however, the tissue nitrite stores could then be reduced to NO and 5-nitrosothiol, thus sustaining critical vasodilation.

VII. Methods of Use

Therapeutic application of nitrite now can be used to provide selective vasodilation in a subject, and particularly to hypoxemic and ischemic tissue in the subject, and will be useful to treat hemolytic conditions such as sickle cell disease, where free hemoglobin released during hemolysis scavenges NO and disrupts NO-dependent vascular function. Nitrite is expected to not only inhibit the ability of free hemoglobin to scavenge NO by oxidizing it to methemoglobin, but also to generate NO in tissue beds with low oxygen tension. Thus, the applied nitrite will preferentially release nitric oxide at areas of low oxygen tension, thereby providing localized vasodilation and/or increased blood flow.

Nitrites can be administered to a subject to increase blood flow to a tissue of the subject, for example, to increase blood flow to a tissue, for instance a tissue with low oxygen tension; to cause vasodilation; to decrease a subject's blood pressure; to treat a subject having a condition associated with elevated blood pressure; to treat a hemolytic condition; to treat vascular complications associated with treatments or conditions that cause hemolysis; to treat pulmonary hypertension, cerebral vasospasm, or low blood flow to organs (such as ischemia reperfusion injury to organs including brain, heart, kidney, placenta, and liver); and/or to treat organs before and after transplantation.

Nitrite has Vasodilatory Properties In Vivo

The vasodilator properties of nitrite and the mechanisms for its bioactivation were investigated as described herein. Sodium nitrite infused at 36 moles per minute into the forearm brachial artery of 18 normal volunteers resulted in a regional nitrite concentration of 222 µM and, surprisingly, a 175% increase in resting forearm blood flow. Increased blood flow was observed at rest, during NO synthase inhibition and with exercise. The nitrite infusion also surprisingly resulted in increased tissue perfusion, as demonstrated by increases in venous hemoglobin-oxygen saturation, partial pressure of oxygen, and pH. Increased systemic concentrations of nitrite (16 µM) significantly reduced mean arterial blood pressure.

In an additional ten subjects, the dose of nitrite was reduced 2-logs, resulting in a forearm nitrite concentration of 2 µM at rest and 0.9 µM during exercise (FIG. 3). These concentrations of nitrite surprisingly significantly increased blood flow at rest and during NO synthase inhibition, with and without exercise.

Nitrite infusions were associated with the rapid formation of erythrocyte iron-nitrosyl-hemoglobin, and to a lesser extent, S-nitroso-hemoglobin across the forearm vasculature. Formation of these NO-Hb adducts was inversely proportional to the oxyhemoglobin saturation. Additionally, vasodilation of rat aortic rings and the formation of both NO gas and NO-modified hemoglobin from the nitrite reductase activity of deoxyhemoglobin and deoxygenated erythrocytes was observed, a result that links tissue hypoxia, hemoglobin allostery, and nitrite bioactivation. These results indicate that physiological levels of blood and tissue nitrite are a major bioavailable pool of NO that contributes to vaso-regulation and provide a mechanism for hypoxic vasodilation via reaction of vascular nitrite with deoxygenated heme proteins in tissue and/or the erythrocyte.

The findings described herein that administration of nitrite reduces blood pressure and increases blood flow are unexpected and surprising because published reports to date teach the person of ordinary skill in the art that pharmacological levels of nitrites (below about 100-200 µM), when administered to subjects, lack intrinsic vasodilatory properties (Lauer et al., *Proc Natl Acad Sci USA*, 98:12814-9, 2001).

It is also believed that pharmaceutically acceptable salts of nitrite can be infused into patients with hemolytic disease, such as sickle cell disease, to improve blood flow, limit ischemia-reperfusion tissue injury, and oxidize cell-free plasma Hb. These effects should be useful in the treatment of sickle cell vaso-occlusive pain crisis, stroke (brain ischemia) and the acute chest syndrome.

Cytoprotective Effects of Nitrite During Ischemia-Reperfusion of the Heart and Liver The anion nitrite ($NO_2^-$) forms as a consequence of nitric oxide (NO) oxidation and is present at concentrations of 0.3-1.0 µM in plasma and 1-20 µM in tissue (Gladwin et al., *Proc Natl Acad Sci USA* 97:11482-11487, 2000; Rodriguez et al., *Proc Natl Acad Sci USA* 100:336-341, 2003; Rassaf et al., *Nat Med* 9:481-483, 2003; Bryan et al., *Proc Natl Acad Sci USA.*, 2004; Gladwin et al., *J Clin Invest* 113:19-21, 2004). Nitrite has been historically considered an inert metabolic end product with limited intrinsic biological activity (Lauer et al., *Proc Natl Acad Sci USA* 98:12814-12819, 2001; McMahon, *N Engl J Med* 349:402-405; author reply 402-405, 2003; Pawloski, *N Engl J Med* 349:402-405; author reply 402-405, 2003). Recent data from our group and others suggest that nitrite may be reduced to NO during hypoxia and acidosis (Gladwin et al., *Proc Natl Acad Sci USA* 97:11482-11487, 2000; Bryan et al., *Proc Nail Acad Sci USA.*, 2004; Cosby et al., *Nat Med* 9:1498-1505, 2003; Nagababu et al., *J Biol Chem* 278:46349-46356, 2003; Tiravanti et al., *J Biol Chem* 279:11065-11073, 2004). At extremely low tissue pH and $PO_2$, nitrite may be reduced to NO by disproportionation (acidic reduction; Zweier et al., *Nat Med* 1:804-809, 1995) or by the enzymatic action of xanthine oxidoreductase (Millar et al., *FEBS Lett* 427:225-228, 1998; Zhang et al., *Biochem Soc Trans* 25:524 S, 1997; Godber et al., *J Biol Chem* 275:7757-7763, 2000; Li et al., *J Biol Chem* 276:24482-24489, 2001).

Nitrite represents a circulating and tissue storage form of nitric oxide (NO) whose bioactivation is mediated by the nitrite reductase activities of deoxyhemoglobin. Because the rate of NO generation from nitrite is linearly dependent on reductions in oxygen and pH, we hypothesized that nitrite would be reduced to NO in ischemic tissue and exert NO-dependent protective effects. Solutions of sodium nitrite were administered in the setting of hepatic and cardiac ischemia-reperfusion (I/R) injury in mice. In hepatic I/R, nitrite exerted profound dose dependent protective effects on cellular necrosis and apoptosis with highly significant protective effects observed at near-physiological nitrite concentrations (0.6 µM). In myocardial I/R injury, nitrite reduced cardiac infarct size by 67% and significantly improved post-ischemic left ventricular ejection fraction. Consistent with hypoxia dependent nitrite bioactivation, nitrite was reduced to NO, S-nitrosothiols, N-nitrosamines and iron-nitrosylated heme proteins within 1-30 minutes of reperfusion. Nitrite-mediated protection was dependent on NO generation and independent of eNOS and HO-1. These results suggest that nitrite is a biological storage reserve of NO subserving a critical function in tissue protection from ischemic injury. These studies evince an unexpected and novel therapy for diseases such as myocardial infarction, organ preservation and transplantation, and shock states.

Although reperfusion of ischemic tissues provides oxygen and metabolic substrates necessary for the recovery and survival of reversibly injured cells, reperfusion itself actually results in the acceleration of cellular necrosis (Braunwald et al., *J. Clin. Invest.* 76:1713-1719, 1985). Ischemia-reperfusion is characterized by the formation of oxygen radicals upon reintroduction of molecular oxygen to ischemic tissues resulting in widespread lipid and protein oxidative modifications of cellular proteins, mitochondrial injury, and tissue apoptosis and necrosis (McCord et al., *Adv Myocardiol* 5:183-189, 1985). In addition, following reperfusion of ischemic tissues blood flow may not return uniformly to all portions of the ischemic tissues, a phenomenon that has been termed the "no-reflow" phenomenon (Kloner et al., *J Clin Invest* 54:1496-1508, 1974). Reductions in blood flow following reperfusion are thought to contribute to cellular injury and necrosis (Kloner et al., *J Clin Invest* 54:1496-1508, 1974). The sudden re-introduction of blood into ischemic tissue also results in a dramatic increase in calcium delivery to the previously ischemic tissue (i.e., "calcium paradox") resulting in massive tissue disruption, enzyme release, reductions in high energy phosphate stores, mitochondrial injury, and necrosis (Nayler, *Amer. J. Path.* 102:262, 1981; Shen et al., *Amer. J. Path* 67:417-440, 1972). Recent studies have also indicated that the ischemia-reperfusion injury is also characterized by an inappropriate inflammatory response in the microcirculation resulting in leukocyte-endothelial cell interactions that are mediated by the upregulation of both leukocyte and endothelial cell adhesion molecules (Lefer et al., *Cardiovasc Res* 32:743-751, 1996; Entman et al., *Faseb J* 5:2529-2537, 1991). Intensive research efforts have been focused on ameliorating various pathophysiological components of ischemia-reperfusion injury to limit the extent of tissue injury and necrosis.

NO, NO donors, and NO synthase activation or transgenic over-expression have been shown to exert protective effects on this process in a number of models (Lefer et al., *New Horiz* 3:105-112, 1995; Lefer et al., *Circulation* 88:2337-2350, 1993; Nakanishi et al., *Am J Physiol* 263:H1650-1658, 1992; Jones et al., *Am J Physiol Heart Circ Physiol* 286:H276-282, 2004; Jones et al., *Proc Natl Acad Sci USA* 100:4891-4896. 2003; Kanno et al., *Circulation* 101:2742-2748, 2000), but in other models appears harmful (Flogel et al., *J Mol Cell Cardiol* 31:827-836. 1999; Menezes et al., *Am J Physiol* 277: G144-151, 1999; Woolfson et al., *Circulation* 91:1545-1551, 1995; Schulz, R. et al., *Cardiovasc Res* 30:432-439, 1995). Evaluation of these studies suggests a critical effect of dose and duration of NO exposure, resulting in a narrow therapeutic safety window for NO in ischemia-reperfusion pathophysiology (Bolli, *J. Mol. Cell. Cardio.* 33:1897-1918, 2001; Wink et al., *Am J Physiol Heart Circ Physiol* 285:H2264-2276, 2003). An additional limitation is that NO formation from NO synthase requires oxygen as substrate, a molecule whose availability becomes limited during ischemia.

We therefore considered the use of nitrite in this context for the following reasons: (1) It is a naturally occurring substance with no potentially toxic "leaving group" (2), it is selectively reduced to NO in tissues with low oxygen tension and low pH (Bryan et al., *Proc Natl Acad Sci USA.*, 2004; Cosby et al., *Nat Med* 9:1498-1505, 2003; Nagababu et al., *J Biol Chem* 278: 46349-46356, 2003; Tiravanti et al., *J Biol Chem* 279:11065-11073, 2004; Doyle et al., *J Biol Chem* 256:12393-12398, 1981; Luchsinger et al., *Proc Natl Acad Sci USA* 100:461-466, 2003), (3) its activation does not require molecular oxygen (Cosby et al., *Nat Med* 9:1498-1505, 2003), and (4) NO is known to maintain heme proteins in a reduced and liganded state (Herold et al., *Free Radic Biol Med* 34:531-545, 2003; Herold et al., *J Biol Inorg Chem* 6:543-555, 2001; Fernandez et al., *Inorg Chem* 42:2-4, 2003), limit free iron and heme mediated oxidative chemistry (Kanner et al., *Arch Biochem Biophys* 237:314-321, 1985; Kanner et al., *Lipids* 20:625-628, 1985; Kanner et al., *Lipids* 27:46-49, 1992), transiently inhibit cytochome c oxidase and mitochondrial respiration (Tones et al., *FEBS Lett* 475:263-266, 2000; Brown et al., *FEBS Lett* 356:295-298, 1994; Cleeter et al., *FEBS Lett* 345: 50-54, 1994; Rakhit et al., *Circulation* 103:2617-2623, 2001), and modulate apoptotic effectors (Mannick et al., *Science* 284:651-654, 1999), all mechanisms that might participate in cytotoxicity following severe ischemia.

Nitric oxide has been shown to quench oxygen free radicals in a transient ischemia and reperfusion injury animal models (Mason et al., *J Neurosurg* 93: 99-107, 2000), significantly limiting volume of stroke (Pluta et al., *Neurosurgery*, 48:884-892, 2001). Therefore, nitrite via releasing NO in the area of reperfusion may also have the same beneficial effect on stroke via limiting oxygen free radicals presence after reperfusion.

Furthermore, the selective opening of blood-tumor barrier by NO facilitates penetration of chemotherapeutic agents into the brain tumor (Weyerbrock et al., *J. Neurosurgery*, 99:728-737, 2003); it is believed that this will also enhance penetration of other agents, particularly therapeutic agents such as radiation therapy, brain cancer. Therefore, due to hypoxic conditions within the brain tumor it is possible that nitrite can also selectively open the blood-tumor barrier providing beneficial effect in combination with chemotherapy.

Inhaled Nebulized Nitrite is a Pulmonary Vasodilator

Persistent pulmonary hypertension of the newborn occurs with an incidence of 0.43-6.8/1,000 live births and is associated with mortality rates between 10-20% (Walsh-Sukys et al., *Pediatrics* 105, 14-20, 2000). Survivors may develop neurodevelopmental and audiological impairment (46%), cognitive delays (30%), hearing loss (19%) and a high rate of rehospitalization (22%) (Lipkin et al., *J Pediatr* 140, 306-10, 2002).

Pulmonary hypertension occurs as a primary or idiopathic disease (Runo & Loyd, *Lancet* 361:1533-44, 2003; Trembath & Harrison, *Pediatr Res* 53:883-8, 2003), as well as secondary to a number of systemic and pulmonary diseases (Rubin, *N Engl J Med* 336:111-7, 1997). Regardless of etiology, pulmonary hypertension is associated with substantial morbidity and mortality. Newborn infants and adults with pulmonary disease often develop systemic hypoxemia, reduced oxyhemoglobin saturation and increased pulmonary vascular resistance (Rubin, *N Engl J Med* 336:111-7, 1997; Haworth, *Heart* 88:658-64, 2002). Therapeutically administered inhaled nitric oxide (NO) decreases pulmonary vascular resistance in newborns and adults and improves ventilation-to-perfusion matching and oxygenation; in newborns, inhaled NO reduces chronic lung damage and reduces the need for extracorporeal membrane oxygenation. Randomized placebo-controlled trials of inhaled NO therapy for term and near-term newborns with severe hypoxic respiratory failure demonstrated an improvement in hypoxemia and reduced need for extracorporal membrane oxygenation (Clark et al., *N Engl J Med* 342, 469-74, 2000; Roberts et al., *N Engl J Med* 336, 605-10, 1997; The Neonatal Inhaled Nitric Oxide Study Group. *N Engl J Med* 336, 597-604, 1997). A recent randomized placebo-controlled trial in premature infants with respiratory distress syndrome indicated that treatment with inhaled NO reduced the combined endpoint of death and chronic lung disease (Schreiber et al., *N Engl J Med* 349, 2099-107, 2003).

Despite the encouraging results regarding treatment of persistent pulmonary hypertension of the newborn with inhaled NO, the therapy does have several significant limitations (Martin, *N Engl J Med* 349, 2157-9, 2003): considerable cost (Jacobs et al., *Crit Care Med* 30, 2330-4, 2002; Pierce et al., *Bmj* 325, 336, 2002; Subhedar et al., *Lancet* 359, 1781-2, 2002; Angus et al., *Pediatrics* 112, 1351-60, 2003), technical difficulties involved in adapting NO delivery systems for neonatal transport (Kinsella et al., *Pediatrics* 109, 158-61, 2002), and the lack of availability in small community hospitals and developing countries. In addition, NO reacts with oxygen, forming the toxic nitrogen dioxide, and thus must be stored and delivered in nitrogen at high flow rates. The gas and delivery systems are costly and the requisite delivery technology is not universally available. Therefore, alternative NO-based therapies for the treatment of pulmonary hypertension are highly desirable.

The relationship between nitrite and nitric oxide has been appreciated for close to a century, with Haldane and later Hoagland recognizing that iron-nitrosylated myoglobin (NO bound to heme) formed as an end-product during nitrite-based meat curing (Gladwin, *J Clin Invest* 113, 19-21, 2004). More than fifty years ago, Furchgott and Bhadrakom reported that nitrite vasodilated aortic ring preparations in vitro (Furchgott & Bhadrakom, *J Pharmacol Exp Ther* 108, 129-43, 1953); this observation was later explored by Ignarro's group in experiments evaluating the role of soluble guanylyl cyclase in endothelium-dependent vasodilation (Ignarro et al., *J Pharmacol Exp Ther* 218, 739-49, 1981). However, the high concentrations of nitrite, typically in the millimolar range, required to elicit vasodilation in aortic ring in vitro bioassays precluded consideration of nitrite as a physiological vasodilator (Lauer et al., *Proc Natl Acad Sci USA* 98, 12814-9, 2001; Pawloski, *N Engl J Med* 349, 402-5; author reply 402-5, 2003; McMahon, *N Engl J Med* 349, 402-5; author reply 402-5, 2003).

Two decades later, in human physiological studies, we observed artery-to-vein differences for nitrite across the human forearm with increased extraction occurring during NO inhalation and exercise stress with concomitant NO synthase inhibition (Gladwin et al., *Proc Natl Acad Sci USA* 97, 11482-7, 2000). This finding suggested that nitrite was being metabolized across the forearm with increased consumption during exercise. Based on these observations along with data from a number of investigators that identified mechanisms for non-enzymatic (nitrite disproportionation) (Zweier et al., *Nat Med* 1, 804-9, 1995) and enzymatic (xanthine oxidoreductase) (Zweier et al., *Nat Med* 1, 804-9, 1995; Millar et al., *FEBS Lett* 427, 225-8, 1998; Tiravanti et al., *J Biol Chem* 279:11065-11073, 2004; Li et al., *J Biol Chem*, 279(17): 16939-16946, 2004) reduction of nitrite to NO, we hypothesized that nitrite is reduced in vivo to NO in tissues under conditions of low $Po_2$ or pH. We found support for this hypothesis in studies of normal human volunteers wherein nitrite infusion into the forearm resulted in marked vasodilation even under basal conditions at near-physiological nitrite concentrations (Example 1; Cosby et al., *Nat Med* 9, 1498-505, 2003). The mechanism of this vasodilation was consistent with a reaction of nitrite with deoxygenated hemoglobin to form NO, methemoglobin (Cosby et al., *Nat Med* 9, 1498-505, 2003; Nagababu et al., *J Biol Chem* 278, 46349-56, 2003) and other NO adducts.

This nitrite reductase activity of deoxyhemoglobin was extensively characterized by Doyle and colleagues in 1981 (Doyle et al., *J Biol Chem* 256, 12393-8, 1981): nitrite appears to react with deoxyhemoglobin and a proton to form NO and methemoglobin. Such chemistry is ideally suited for hypoxic generation of NO from nitrite, as the reaction is enhanced by hemoglobin deoxygenation and acid, providing a graded production of NO from nitrite linked to physiological changes in oxygen and $pH/CO_2$. The observation in this current example that inhaled nitrite generates iron-nitrosyl-hemoglobin, exhaled NO gas, and produces vasodilation in proportion to decreasing levels of oxygenation and pH further indicates that nitrite is a bioavailable storage pool of NO and that hemoglobin may have a physiological function as a nitrite reductase, potentially contributing to hypoxic vasodilation (see Example 1). In addition to these mechanistic considerations, this example supports another therapeutic application of nitrite, extending beyond its well-established role in the treatment of cyanide poisoning.

We show herein (Example 3) that this biochemical reaction can be harnessed for the treatment of neonatal pulmonary hypertension, an NO-deficient state characterized by pulmonary vasoconstriction, right-to-left shunt pathophysiology, ventilation/perfusion inhomogeneity and systemic hypoxemia. We delivered inhaled sodium nitrite by aerosol to newborn lambs with hypoxic and normoxic pulmonary hypertension. Inhaled nitrite elicited a rapid and sustained reduction (~60%) in hypoxia induced pulmonary hypertension, a magnitude approaching that of the effects of 20 ppm NO gas inhalation and which was associated with the immediate appearance of increasing levels of NO in expiratory gas. Pulmonary vasodilation elicited by aerosolized nitrite was deoxyhemoglobin- and pH-dependent and was associated with increased blood levels of hemoglobin iron-nitrosylation. Significantly, from a therapeutic standpoint, short term delivery of nitrite, dissolved in saline, via nebulization produced selective and sustained pulmonary vasodilation with no appreciable increase in blood methemoglobin levels. These data support the paradigm that nitrite is a vasodilator acting via conversion to NO, a process coupled to hemoglobin deoxygenation and protonation, and further evince a novel, simple and inexpensive potential therapy for neonatal pulmonary hypertension.

Aerosolized nitrite is an effective vasodilatory in the described newborn lamb model (Example 3). It can be readily administered by nebulization, and appears to exhibit a wide therapeutic-to-safety margin, with limited systemic hemodynamic changes and methemoglobin production. This presents an attractive therapeutic option to inhaled NO. Nitrite is an ideal "NO producing" agent in that it 1) is a naturally occurring compound in blood, alveolar lining fluid, and tissue, and 2) has no parent-compound leaving group, such as the diazenium diolates, that requires extensive toxicological study prior to translation to human disease.

Inhaled nitrite is a potent and selective vasodilator of pulmonary circulation of the newborn lamb. This further supports the paradigm that nitrite is an NO-dependent vasodilator whose bioactivation is coupled to hemoglobin deoxygenation and protonation. This has clinical applications in veterinary and medical situations, including pulmonary hypertension and other pulmonary syndromes with apparent NO deficiencies. Based on the data presented herein, it is believed that inhaled nitrite will have efficacy in all known and tested applications of inhaled NO.

Prevention of Cerebral Artery Vasospasm after Subarachnoid Hemorrhage

Further, it has been discovered that nitrite infusion can be used to prevent cerebral artery vasospasm after aneurismal hemorrhage (Example 4). Subarachnoid hemorrhage (SAH) due to the rupture of intracranial aneurysms affects 28,000 Americans annually. Almost 70% of patients with aneurysmal SAH develop severe spasm of the cerebral arteries on the seventh day after SAH. Despite aggressive medical therapy, neurological deficits resulting from vasospasm continue to be a major cause of morbidity and mortality. Although the etiology of cerebral vasospasm is poorly understood, there is increasing evidence that erythrocyte hemolysis in the cerebrospinal fluid and decreased availability of nitric oxide (NO), a potent vasodilator, plays a significant role. Reversal of vasospasm by NO or NO prodrugs has been documented in several animal models.

Delayed cerebral vasospasm (DCV) remains the single cause of permanent neurological deficits or death in at least fifteen percent of patients following otherwise successful endovascular or surgical treatment for ruptured intracranial aneurysm. Decreased bioavailability of nitric oxide (NO) has been mechanistically associated with the development of DCV. A primate model system for cerebral artery vasospasm was used to determine whether infusions of nitrite, a naturally occurring anion that reacts with deoxyhemoglobin to form NO and S-nitrosothiol, might prevent DCV via reactions with perivascular hemoglobin.

Figure 16:
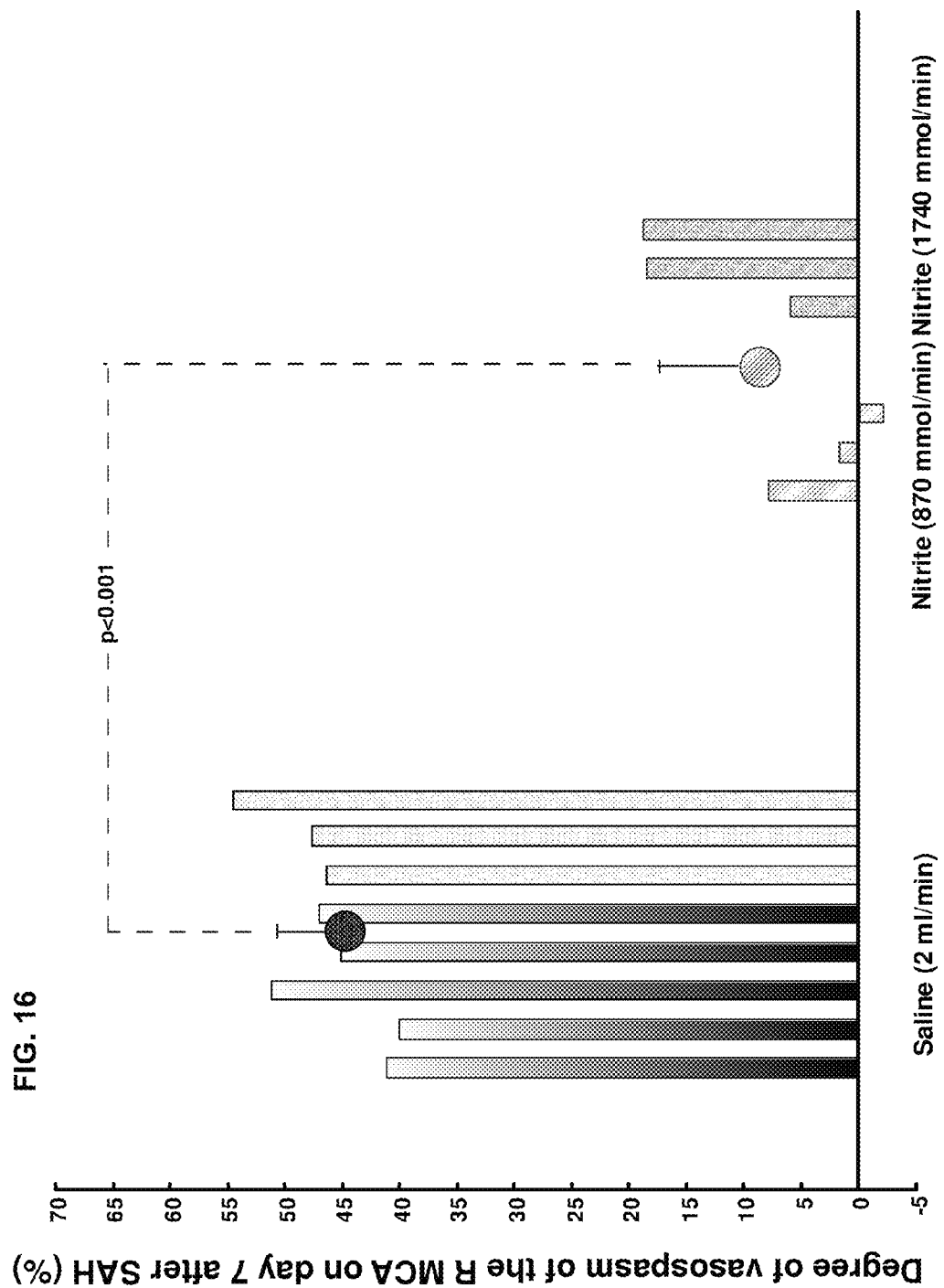
FIG. 16 depicts degree of vasospasm of the right middle cerebral artery (R MCA) in each animal from all experimental groups (8 control, 3 low dose, and 3 high dose of nitrite). R MCA vasospasm was assessed as the area of the proximal 14-mm segment of the right MCA by three blinded examiners using a computerized image analysis system (NIH Image 6.21). Arteriographic vasospasm was quantified relative to each animal baseline arteriogram. The mean values for saline vs. nitrite groups are represented by the circles; bars represent standard deviations. Statistical significance $p<0.001$.

As described in Example 4, nitrite infusions (45 mg/kg and 60 mg/kg per day) that produced blood levels of nitrite ranging from 10-60 microM with no clinically significant methemoglobin formation (<5%) were associated with increases in plasma cerebrospinal fluid nitrite and modest increases in blood methemoglobin concentrations (2% or less) without systemic hypotension, and significantly reduced the severity of vasospasm (FIGS. 15 and 16). No animals infused with sodium nitrite developed significant vasospasm; mean reduction in the R MCA area on day 7 after SAH was 8±9% versus 45±5%; P<0.001) Pharmacological effects of nitrite infusion were associated with bioconversion of cerebrospinal fluid nitrite to S-nitrosothiol, a potent vasodilating NO donor intermediate of nitrite bioactivation. There was no clinical or pathological evidence of nitrite toxicity.

Subacute sodium nitrite infusions prevent DCV in a primate model of SAH, and do so without toxicity. These data evince a novel, safe, inexpensive, and rationally designed therapy for DCV, a disease for which no current preventative therapy exists.

The results presented herein suggest that sodium nitrite therapy may prevent tissue injury produced by metabolic products of hemoglobin, either by vascular spasm, or by other mechanisms of tissue injury by these metabolic products.

Treatment or Amelioration of Gestational or Fetal Cardiovascular Malconditions

Based on results presented herein, it is believed that nitrite, particularly pharmaceutically acceptable salts of nitrite as described herein, can be used to treat hypertension and preeclampsia during pregnancy. Such therapy would include action of nitrites on spastic and diseased blood vessels within the placenta.

Also suggested are methods for treating fetuses in utero, particularly those afflicted with cardiovascular anomalies, hypertension, and misdirected blood flow. It is believed that it may be possible to add nitrites to the amniotic fluid, and thus indirectly to the fetus, to achieve vasodilation and redistribution of blood flow before birth. By this means, fetal cardiovascular system development and function could be altered, for instance with promotion of blood flow to the brain and heart. To be effective longer term, it is envisioned that embodiments of such fetal therapy would include the introduction of one or more mini-osmotic pumps, containing nitrite (e.g., sodium nitrite), into the amniotic cavity to thereby achieve sustained, slow release. For instance, such minipumps could be used to achieve sustained release throughout days and weeks of pregnancy.

Also suggested are methods for treating fetuses in whom plasma nitrite levels may be depressed by immune incompatibility and associated hemolytic anemias. Such fetal treatment may be extended into the neonatal period. Administrated in the fetal period may include implantation of nitrite-charged osmotic minipumps into the amniotic cavity and could include aerosol inhalation after birth.

VIII. Formulations and Administration

Nitrites, including their salts, are administered to a subject in accordance to methods provided herein, in order to decrease blood pressure and/or increase vasodilation in a subject. Administration of the nitrites in accordance with the present disclosure may be in a single dose, in multiple doses, and/or in a continuous or intermittent manner, depending, for example, upon the recipient's physiological condition, whether the purpose of the administration is therapeutic or prophylactic, and other factors known to skilled practitioners. The administration of the nitrites may be essentially continuous over a preselected period of time or may be in a series of spaced doses. The amount administered will vary depending on various factors including, but not limited to, the condition to be treated and the weight, physical condition, health, and age of the subject. Such factors can be determined by a clinician employing animal models or other test systems that are available in the art.

To prepare the nitrites, nitrites are synthesized or otherwise obtained and purified as necessary or desired. In some embodiments of the disclosure, the nitrite is a pharmaceutically-acceptable salt of nitrite, for example, sodium nitrite. In some embodiments of the disclosure, the nitrite is not ethyl nitrite. In some embodiments of the disclosure, the sodium nitrite is not on a medical devise, for example, not on a stent. In some embodiments of the disclosure, the nitrite is not in the form of a gel. The nitrites can be adjusted to the appropriate concentration, and optionally combined with other agents. The absolute weight of a given nitrite included in a unit dose can vary. In some embodiments of the disclosure, the nitrite is administered as a salt of an anionic nitrite with a cation, for example, sodium, potassium, or arginine.

One or more suitable unit dosage forms including the nitrite can be administered by a variety of routes including topical, oral (for instance, in an enterically coated formulation), parenteral (including subcutaneous, intravenous, intramuscular and intraperitoneal), rectal, intraamnitic, dermal, transdermal, intrathoracic, intrapulmonary and intranasal (respiratory) routes.

The formulations may, where appropriate, be conveniently presented in discrete unit dosage forms and may be prepared by any of the methods known to the pharmaceutical arts. Such methods include the step of mixing the nitrite with liquid carriers, solid matrices, semi-solid carriers, finely divided solid carriers or combinations thereof, and then, if necessary, introducing or shaping the product into the desired delivery system. By "pharmaceutically acceptable" it is meant a carrier, diluent, excipient, and/or salt that is compatible with the other ingredients of the formulation, and not deleterious or unsuitably harmful to the recipient thereof. The therapeutic compounds may also be formulated for sustained release, for example, using microencapsulation (see WO 94/07529, and U.S. Pat. No. 4,962,091).

The nitrites may be formulated for parenteral administration (e.g., by injection, for example, bolus injection or continuous infusion) and may be presented in unit dose form in ampoules, pre-filled syringes, small volume infusion containers or in multi-dose containers. Preservatives can be added to help maintain the shelve life of the dosage form. The nitrites and other ingredients may form suspensions, solutions, or emulsions in oily or aqueous vehicles, and may contain formulatory agents such as suspending, stabilizing and/or dispersing agents. Alternatively, the nitrites and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers and vehicles that are available in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add other ingredients such as antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

The pharmaceutical formulations of the present disclosure may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present disclosure include water and physiologically acceptable buffered saline solutions, such as phosphate buffered saline solutions. Merely by way of example, the buffered solution can be at a pH of about 6.0-8.5, for instance about 6.5-8.5, about 7-8.

The nitrites can also be administered via the respiratory tract. Thus, the present disclosure also provides aerosol pharmaceutical formulations and dosage forms for use in the methods of the disclosure. In general, such dosage forms include an amount of nitrite effective to treat or prevent the clinical symptoms of a specific condition. Any attenuation, for example a statistically significant attenuation, of one or more symptoms of a condition that has been treated pursuant to the methods of the present disclosure is considered to be a treatment of such condition and is within the scope of the disclosure.

For administration by inhalation, the composition may take the form of a dry powder, for example, a powder mix of the nitrite and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984). Nitrites may also be administered in an aqueous solution, for example, when administered in an aerosol or inhaled form. Thus, other aerosol pharmaceutical formulations may include, for example, a physiologically acceptable buffered saline solution. Dry aerosol in the form of finely divided solid compound that is not dissolved or suspended in a liquid is also useful in the practice of the present disclosure.

For administration to the respiratory tract, for example, the upper (nasal) or lower respiratory tract, by inhalation, the nitrites can be conveniently delivered from a nebulizer or a pressurized pack or other convenient means of delivering an aerosol spray. Pressurized packs may include a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker). The nitrites may also be delivered via an ultrasonic delivery system. In some embodiments of the disclosure, the nitrites may be delivered via an endotracheal tube. In some embodiments of the disclosure, the nitrites may be delivered via a face mask.

The present disclosure further pertains to a packaged pharmaceutical composition such as a kit or other container. The kit or container holds a therapeutically effective amount of a pharmaceutical composition of nitrite and instructions for using the pharmaceutical composition for treating a condition.

IX. Combination Therapies

Furthermore, the nitrite may also be used in combination with other therapeutic agents, for example, pain relievers, anti-inflammatory agents, antihistamines, and the like, whether for the conditions described or some other condition. By way of example, the additional agent is one or more selected from the list consisting of penicillin, hydroxyurea, butyrate, clotrimazole, arginine, or a phosphodiesterase inhibitor (such as sildenafil).

Generally, it is believed that therapies that have been suggested or demonstrated to be effective when combined with NO therapy, may also be effective when combined with nitrite administration. All combination therapies that have been are being studied with NO therapy (inhaled or otherwise) are likely to be worthy of study in combination with nitrite therapy. See, for instance, Uga et al., *Pediatr. Int.* 46 (1): 10-14, 2004; Gianetti et al., *J Thorac. Cardiov. Sur.* 127 (1): 44-50, 2004; Stubbe et al., *Intens. Care Med.* 29 (10): 1790-1797, 2003; Wagner et al., *Eur. Heart J* 23: 326-326 Suppl. 2002; Park et al., *Yonesi Med J* 44 (2):219-226, 2003; Kohele, *Israel Med. Assoc. J.* 5:19-23, 2003, for discussions of combination therapies used with NO.

Furthermore, pharmaceutically-acceptable nitrite salts (such as, for instance, sodium nitrite) may be used in combinations with drugs and agents that limit the elimination rate of administered nitrites. This combination could serve to prolong the duration of action of nitrite and would include antagonists and inhibitors of enzymes affecting the elimination of nitrites or their conversion to NO.

Alternatively, the nitrite may be used in combinations with drugs and agents that augment the action of nitrites. This combination could serve to increase the strength of responses to administered nitrites.

Recombinant tissue plasminogen activator (rt-PA) and urokinase are the only drugs that have proven to open occluded brain arteries in ischemic stroke. It is believed possible that using nitrite via quenching oxygen free radicals produced in response to reperfusion may provide an additional beneficial effect.

The following examples are provided to illustrate certain particular features and/or embodiments. These examples should not be construed to limit the invention to the particular features or embodiments described.

Example 1

Nitrite has Vasodilatory Properties In Vivo

This example provides a demonstration that nitrite, administered by infusion to the forearm of human subjects, is an effective vasodilator.

Methods

Human Subjects Protocol.

The protocol was approved by the Institutional Review Board of the National Heart, Lung and Blood Institute, and informed consent was obtained from all volunteer subjects. Nine men and nine women, with an average age of 33 years (range 21-50 years), participated in the study. An additional 10 subjects returned three-six months later for a second series of experiments with low dose nitrite infusion. Volunteers had a normal hemoglobin concentration, and all were in excellent general health without risk factors for endothelial dysfunction (fasting blood sugar>120 mg/dL, low-density lipoprotein cholesterol>130 mg/dl, blood pressure>145/95 mmHg, smoking within two years, cardiovascular disease, peripheral vascular disease, coagulopathy, or any other disease predisposing to vasculitis or Reynaud's phenomenon). Subjects with G6PD deficiency, known cytochrome B5 deficiency or a baseline methemoglobin level>1% were excluded (no screened subjects met these exclusion criteria). Lactating and pregnant females were excluded (one subject with positive HCG levels was excluded). No volunteer subject was allowed to take any medication (oral contraceptive agents allowed), vitamin supplements, herbal preparations, nutriceuticals or other "alternative therapies" for at least one month prior to study and were not be allowed to take aspirin for one week prior to study.

Forearm Blood Flow Measurements

Brachial artery and antecubital vein catheters were placed into the arm, with the intra-arterial catheter connected to a pressure transducer for blood pressure measurements and an infusion pump delivering normal saline at 1 mL/min. After 20 minutes of rest, baseline arterial and venous blood samples were obtained and forearm blood flow measurements were made by strain gauge venous-occlusion plethysmography, as previously reported (Panza et al., *Circulation,* 87, 1468-74, 1993). A series of 7 blood flow measurements were averaged for each blood flow determination. A series of measurements termed Parts I and II were performed in randomized order to minimize a time effect on the forearm blood flow response during nitrite infusion.

Measurement of Blood Flow and Forearm Nitrite Extraction During NO Blockade and Repetitive Exercise Part I:

Following 20 minutes of 0.9% NaCl (saline) solution infusion at 1 mL/min into the brachial artery, arterial and venous blood samples were obtained for the assays described below and forearm blood flow measured. Exercise was performed by repetitive hand-grip at one-third of the predetermined maximum grip strength using a hand-grip dynamometer (Technical Products Co.) (Gladwin et al., *Proc Natl Acad Sci USA,* 97, 9943-8, 2000; Gladwin et al., *Proc Natl Acad Sci USA,* 97, 11482-11487, 2000; Cannon et al., *J Clin Invest,* 108, 279-87, 2001). Each contraction lasted for 10 seconds followed by relaxation for 5 seconds. Following 5 minutes of exercise, forearm blood flow measurements were obtained during relaxation phases of exercise, and arterial and venous samples collected. Following a 20-minute rest period with continued infusion of saline into the brachial artery, repeated baseline blood samples and forearm blood flow measurements were obtained. L-NMMA was then infused at a rate of 1 mL/min (8 μmol/min) into the brachial artery. Following 5 minutes of L-NMMA infusion, forearm blood flow was measured, and arterial and venous blood samples obtained. Forearm exercise was then initiated in that arm during continued L-NMMA infusion. Forearm blood flow was measured and blood samples obtained after 5 minutes of exercise during continued L-NMMA infusion (FIG. 1).

Part II:

After a 30 minute rest period with continued infusion of saline, baseline measurements were obtained, the saline infusion was then stopped, and infusion of nitrite (NaNO$_2$ 36 μmol/ml in 0.9% saline) at 1 ml/min was started. Sodium nitrite for use in humans was obtained from Hope Pharmaceuticals (300 mg in 10 ml water) and 286 mg was diluted in 100 ml 0.9% saline by the Pharmaceutical Development Service to a final concentration of 36 μmol/ml. For the final 9 subjects studied, 0.01-0.03 mM sodium bicarbonate was added to the normal saline, so as to titrate pH to 7.0-7.4. The nitrite solution was light protected and nitrite levels and free NO gas in solution measured by reductive chemiluminescence after all experiments (Gladwin et al., *J Biol Chem,* 21, 21, 2002). Only 50.5±40.5 nM NO was present in nitrite solutions and was unaffected by bicarbonate buffering. There was no correlation between NO levels in nitrite solutions and blood flow effects of nitrite (r=−0.23; P=0.55). After 5 minutes of nitrite infusion, forearm blood flow measurements and blood samples were obtained, with brief interruption of the nitrite infusion to obtain the arterial sample. With continued nitrite infusion, exercise was performed as described previously, with forearm blood flow measurements and blood samples obtained as described above. The nitrite infusion was stopped and saline infusion re-started during the subsequent 30-minute rest period. Following second baseline measurements, the nitrite infusion was re-initiated, along with L-NMMA at 8 μmol/min. Five minutes later, forearm blood flow measurements were performed and blood samples obtained followed by 5 minutes of exercise with continuation of nitrite and L-NMMA infusions. Final forearm blood flow measurements and blood samples obtained. At all time points during part II, blood samples were obtained from the contralateral arm antecubital vein for determination of methemoglobin and systemic levels of NO-modified hemoglobin (FIGS. 2, 3, and 4). The total dose of sodium nitrite infused was 36 μmol/min×15 minutes×2 infusions=1.08 mmol=75 mg (MW NaNO$_2$=69).

In additional studies in 10 subjects the same stages of Parts I and II protocol were followed with infusion of low dose nitrite (NaNO$_2$ 0.36 μmol/ml in 0.9% saline, infused at 1 ml/min).

Arterial and venous pH, pO$_2$, and pCO$_2$, were measured at the bedside using the i-STAT system (i-STAT Corporation, East Windsor, N.J.) and methemoglobin concentration and hemoglobin oxygen saturation measured by co-oximetry.

Measurement of Red Blood Cell S-Nitroso-Hemoglobin and Iron-Nitrosyl-Hemoglobin.

S-nitroso-hemoglobin is unstable in the reductive red blood cell environment and rapidly decays in a temperature and redox dependent fashion, independent of oxygen tension (Gladwin et al., *J Biol Chem,* 21:21, 2002). To stabilize the S-nitroso-hemoglobin for measurement, the red blood cell must be rapidly oxidized with ferricyanide. Before and during nitrite infusions, blood was drawn from both the brachial artery and antecubital vein and the whole blood immediately (at the bedside to eliminate processing time) lysed 1:10 in an NO-hemoglobin "stabilization solution" of PBS containing 1% NP-40 (to solubilize membranes), 8 mM NEM (to bind free thiol and prevent artefactual 5-nitrosation), 0.1 mM DTPA (to chelate trace copper), and 4 mM ferricyanide and cyanide (to stabilize 5-nitrosohemoglobin and prevent artefactual ex-vivo iron-nitrosylation during processing). The samples were desalted across a 9.5 mL bed volume Sephadex G25 column to eliminate nitrite and excess reagents and partially purify hemoglobin (99% hemoglobin preparation). The hemoglobin fraction was quantified by the method of Drabkin, and hemoglobin fractions reacted with and without mercuric chloride (1:5 HgCl$_2$:heme ratio—used to differentiate 5-nitrosothiol which is mercury labile versus iron-nitrosyl which is mercury stable) and then in 0.1 M HCL/0.5% sulfanilamide (to eliminate residual nitrite; Marley et al., *Free Radic Res,* 32, 1-9, 2000). The samples were then injected into a solution of tri-iodide (I$_3^-$) in-line with a chemiluminescent nitric oxide analyzer (Sievers, Model 280 NO analyzer, Boulder, Colo.). The mercury stable peak represents iron-nitrosyl-hemoglobin. This assay is sensitive and specific for both 5-nitroso-hemoglobin and iron-nitrosyl-hemoglobin to 5 nM in whole blood (0.00005% S—NO per heme) (Gladwin et al., *J Biol Chem,* 21, 21, 2002).

Analysis was initially performed using red blood cell pellet, however, despite placing the sample in ice and immediately separating plasma from erythrocyte pellet, NO formed in the venous blood ex vivo. To measure the true in vivo levels, whole blood was mixed at the bedside 1:10 in the "NO-hemoglobin stabilization solution". Plasma 5-nitroso-albumin formation was negligible during nitrite infusion so this bedside whole blood assay was used to limit processing time and thus more accurately characterize the in vivo chemistry. In a series of validation experiments, both 5-nitroso-hemoglobin and iron-nitrosyl-hemoglobin were stable in the "NO-hemoglobin stabilization solution" for 20 minutes at room temperature with no artifactual formation or decay of NO-modified species (n=6).

Chemiluminescent Detection of NO Gas Released from Deoxyhemoglobin and Deoxygenated Erythrocytes Following Nitrite Addition.

To determine whether free NO radical can form from the reaction of nitrite and deoxyhemoglobin, 100 and 200 µM nitrite was mixed with 5 mL of 660 and 1000 µM deoxygenated erythrocytes in a light protected reaction vessel purged with helium or oxygen (both 21% and 100%) in-line with a chemiluminescent NO analyzer (Seivers, Boulder, Colo.). After allowing equilibration for 5 minutes, nitrite was injected and the rate of NO production measured. Nitrite was injected into PBS as a control and into 100 µM hemoglobin to control for the hemolysis in the 660 and 1000 µM deoxygenated erythrocyte solutions. At the end of all experiments the visible absorption spectra of the supernatant and erythrocyte reaction mixture was analyzed and hemoglobin composition deconvoluted using a least-squares algorithm. There was less than 100 µM hemolysis in the system, no hemoglobin denaturation, and significant formation of iron-nitrosyl-hemoglobin. The NO production from erythrocyte suspensions exceeded that produced from the hemolysate control, consistent with NO export from the erythrocyte.

Statistical Analysis.

An a priori sample size calculation determined that 18 subjects would be necessary for the study to detect a 25% improvement in forearm blood flow during nitrite infusion when forearm NO synthesis had been inhibited by L-NMMA compared with normal saline infusion control values (alpha=0.05, power=0.80). Two-sided P values were calculated by paired t-test for the pair-wise comparisons between baseline and L-NMMA infusion values, between baseline and exercise values, and between nitrite and saline control values at comparable time-points of the study. Repeated measures ANOVA were performed for artery-to-vein gradients of NO species during basal, L-NMMA infusion, and exercise conditions. Measurements shown are mean±SEM.

Results and Discussion

Eighteen healthy subjects (9 males, 9 females; age range 21 to 50 years) were enrolled in a physiological study to determine if nitrite is a vasodilator and to examine nitrite's in vivo chemistry. Part I of the protocol was designed to measure the normal hemodynamic and metabolic responses to exercise and to inhibition of NO synthesis within the forearm as a control for Part II of the protocol, in which these interventions were performed during nitrite infusion. Initial baseline measurements included a mean blood pressure of 85.6±3.7 mm Hg and forearm blood flow of 4.0±0.3 ml/min per 100 mL tissue (FIG. 1A). Repetitive hand-grip forearm exercise increased blood flow approximately 600% over resting values, and significantly decreased ipsilateral venous hemoglobin oxygen saturation, $O_2$, and pH, consistent with increased oxygen consumption and $CO_2$ generation. Following a 20-minute rest period, repeat hemodynamic measurements showed an approximate 10% higher forearm blood flow, but no change in systemic blood pressure or forearm venous hemoglobin oxygen saturation, $pO_2$ and pH values compared with the initial baseline values (FIG. 1B). The NO synthase inhibitor L-NMMA was then infused into the brachial artery at 8 µmol/min for 5 minutes, significantly reducing forearm blood flow by approximately 30% and significantly reducing venous hemoglobin oxygen saturation, $pO_2$ and pH values. Repeated forearm exercise during continued L-NMMA infusion increased blood flow, but to a significantly lower peak value compared with exercise alone (P<0.001). In addition, hemoglobin oxygen saturation, $pO_2$ and pH were significantly lower during exercise with L-NMMA than with exercise without regional NO synthase inhibition (P<0.001, P<0.005 and P=0.027, respectively). Mean arterial blood pressure was unchanged during all components of Part I of the protocol.

FIG. 1 depicts hemodynamic and metabolic measurements at baseline and during exercise, without (FIG. 1A) and with (FIG. 1B) inhibition of NO synthesis in 18 subjects. Mean arterial pressure (MAP), forearm blood flow (FBF), and venous oxyhemoglobin saturation, partial pressure of oxygen ($pO_2$), and pH are shown for all experimental conditions. These interventions and measurements (part I of the protocol) served as a control for Part II of the protocol, in which these interventions were performed during nitrite infusion.

To determine whether nitrite has vasoactivity in humans, in Part II of the protocol sodium nitrite in bicarbonate-buffered normal saline (final concentration 36 µmol/ml) was infused into the brachial arteries of these 18 subjects to achieve an estimated intravascular concentration of approximately 200 µM (Lauer et al., *Proc Natl Acad Sci USA*, 98, 12814-9, 2001). Following repeat baseline measurements and infusion of sodium nitrite at 1 mL/min for 5 minutes, nitrite levels in the ipsilateral antecubital vein increased from 3.32±0.32 to 221.82±57.59 µM (FIG. 2A). Forearm blood flow increased 175% over resting values; venous hemoglobin oxygen saturation, $pO_2$ and pH levels significantly increased over preinfusion values, consistent with increased perfusion of the forearm.

Systemic levels of nitrite were 16 µM as measured in the contralateral arm and were associated with a systemic effect of decreased mean blood pressure of approximately 7 mm Hg. Consistent with immediate NO generation from nitrite during an arterial-to-venous transit, iron-nitrosylated-hemoglobin in the ipsilateral antecubital vein increased from 55.7±11.4 to 693.4±216.9 nM during the nitrite infusion. During forearm exercise with continuation of the nitrite infusion, blood flow increased further, with evidence of metabolic stress by virtue of reduction in forearm venous hemoglobin oxygen saturation, $pO_2$ and pH levels from baseline values. Venous nitrite levels declined, consistent with increased blood flow to the forearm diluting the concentration of infused nitrite. Despite decreasing forearm nitrite concentrations during exercise, iron-nitrosyl-hemoglobin levels increased (FIG. 2A).

Following cessation of nitrite infusion and substitution of saline as the intra-arterial infusate for 30 minutes, repeat baseline measurements showed persistent elevations in systemic levels of nitrite, iron-nitrosyl-hemoglobin and methemoglobin (FIG. 2B) over values obtained prior to the infusion of nitrite almost one hour before. In addition, persistence of a vasodilator effect was also apparent, as forearm blood flow was significantly higher (4.79±0.37 versus 3.94±0.38 mL/min per 100 mL tissue, P=0.003) and systemic blood pressure significantly lower (82.1±3.7 versus 89.2±3.5 mm Hg, P=0.002) than initial pre-nitrite infusion values. During re-infusion into the brachial artery of sodium nitrite 36 µmol/ml, combined with L-NMMA 8 µmol/min in order to again inhibit regional synthesis of NO, similar vasodilator effects of nitrite on resting and exercise forearm blood flow were seen as during nitrite infusion without L-NMMA (FIG. 2B). This stands in contrast to the vasoconstrictor effect of NO synthase inhibition with L-NMMA observed in Part I of the protocol (FIG. 1B). Venous nitrite and iron-nitrosyl-hemoglobin levels followed similar patterns during NO inhibition as during the initial nitrite infusion.

FIG. 2 depicts the effects of infusion of sodium nitrite ($NaNO_2$) in bicarbonate-buffered normal saline (0.9%; final concentration 36 μmol/ml) into the brachial arteries of 18 healthy subjects at 1 ml/min for 5 minutes at baseline and continued during exercise. FIG. 2A depicts the effects without inhibition of NO synthesis. FIG. 2B depicts the effects with inhibition of NO synthesis. Values for mean arterial blood pressure (MAP), forearm blood flow (FBF), venous oxyhemoglobin saturation, partial pressure of oxygen ($pO_2$) and pH, venous nitrite, venous iron-nitrosyl-hemoglobin and venous methemoglobin are shown for all experimental interventions.

Figure 3A:
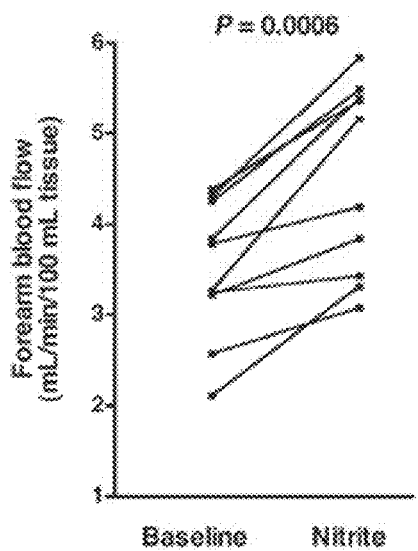
FIG. 3A shows forearm blood flow at baseline and following a five-minute infusion of $NaNO_2$.
Figure 3B:
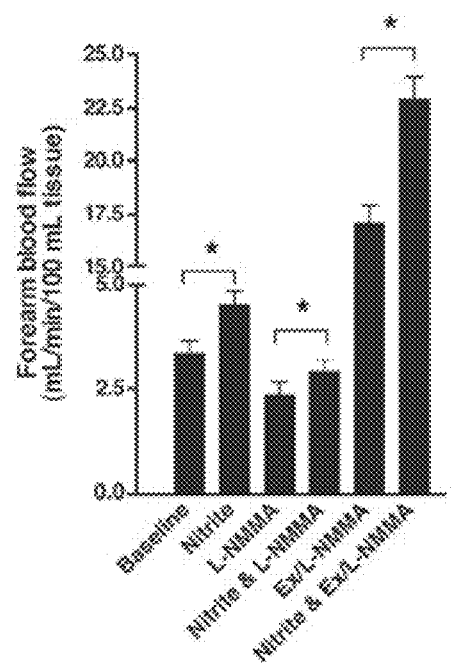
FIG. 3B shows forearm blood flow with and without low-dose nitrite infusion at baseline and during L-NMMA infusion with and without exercise stress.
Figure 3C:
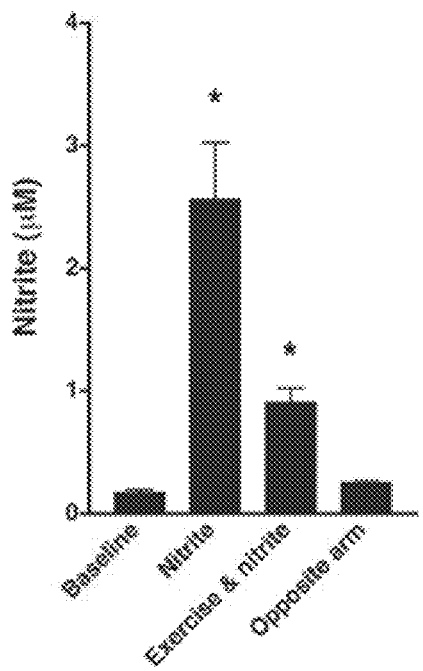
FIG. 3C shows venous levels of nitrite from the forearm circulation at the time of blood flow measurements.
Figure 3D:
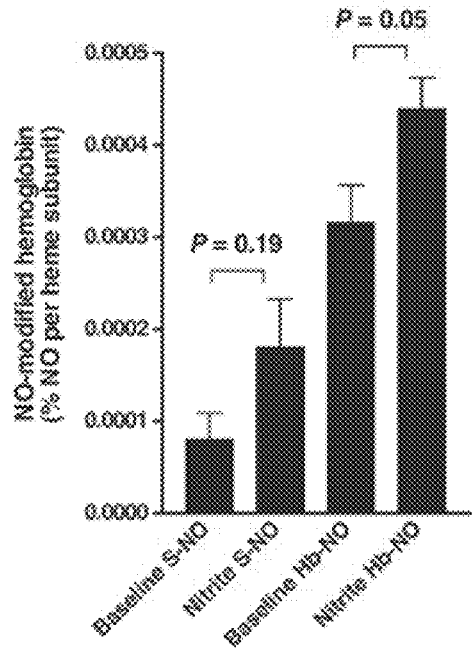
FIG. 3D shows venous levels of S-nitroso-hemoglobin (S—NO) and iron-nitrosyl-hemoglobin (Hb-NO) at baseline and following nitrite infusion during exercise stress.

As a test of the physiological relevance of vascular nitrite as a vasodilator, nitrite concentrations were decreased by 2-logs to 400 nmol/mL. An infusion of 1 mL/min for five minutes in 10 subjects significantly increased forearm blood flow in all ten subjects from 3.49±0.24 to 4.51±0.33 ml/min per 100 mL tissue (FIG. 3A; P=0.0006). Blood flow significantly increased at rest and during NO synthase inhibition with and without exercise (FIG. 3B; P<0.05 during all conditions). Mean venous nitrite levels increased from 176±17 nM to 2564±462 nM following a five-minute infusion and exercise venous nitrite levels decreased to 909±113 nM (secondary to dilutional effects of increased flow during exercise; FIG. 3C). Again, the vasodilator effects of nitrite were paralleled with an observed formation of both iron-nitrosyl-hemoglobin and S-nitroso-hemoglobin across the forearm circulation (FIG. 3D; described below). These data indicate that basal levels of nitrite, from 150-1000 nM in plasma to 10,000 nM in vascular tissue, contribute to resting vascular tone and hypoxic vasodilation.

FIG. 3 depicts the effects of infusion of low-dose sodium nitrite in bicarbonate-buffered normal saline into the brachial arteries of 10 healthy subjects at baseline and during exercise, without and with inhibition of NO synthesis. FIG. 3A depicts forearm blood flow at baseline and following a five-minute infusion of $NaNO_2$ (0.36 μmol/ml in 0.9% saline, infused at 1 ml/min) FIG. 3B depicts forearm blood flow with and without low-dose nitrite infusion at baseline and during L-NMMA infusion with and without exercise stress. FIG. 3C depicts venous levels of nitrite from the forearm circulation at the time of blood flow measurements. FIG. 3D depicts venous levels of S-nitroso-hemoglobin (S—NO) and iron-nitrosyl-hemoglobin (Hb-NO) at baseline and following nitrite infusion during exercise stress.

The vasodilatory property of nitrite during basal blood flow conditions, when tissue $pO_2$ and pH are not exceedingly low, was unexpected. These results indicate that the previously hypothesized mechanisms for nitrite reduction, nitrite disproportionation and xanthine oxidoreductase activity, both of which require extremely low $pO_2$ and pH values not typically encountered in normal physiology, are complemented in vivo by additional factors that serve to catalyze nitrite reduction. While ascorbic acid and other reductants, present in abundance in blood, can provide necessary electrons for nitrous acid reduction, such that the reaction might occur at physiologically attainable pH levels, it is herein reported that deoxyhemoglobin effectively reduces nitrite to NO, within one half-circulatory time. This mechanism provides a graded production of NO along the physiological oxygen gradient, tightly regulated by hemoglobin oxygen desaturation.

Intravascular Formation of NO and S-Nitrosothiol by Reaction of Nitrite with Intraerythrocytic Deoxyhemoglobin Before and during nitrite infusions, blood was drawn from both the brachial artery and antecubital vein and the whole blood immediately (at the bedside to eliminate processing time) lysed 1:10 in an NO-hemoglobin "stabilization solution" and the iron-nitrosyl-hemoglobin and S-nitroso-hemoglobin content determined by tri-iodide-based reductive chemiluminescence and electron paramagnetic resonance spectroscopy as described in Methods. The baseline levels of S-nitroso-hemoglobin and iron-nitrosyl-hemoglobin were at the limits of detection (<50 nM or 0.0005% NO per heme) with no artery-to-vein gradients. Following nitrite infusion in Part II of the protocol venous levels of both iron-nitrosyl-hemoglobin and 5-nitroso-hemoglobin rose strikingly (FIG. 4A). The formation of both NO-hemoglobin adducts occurred across the vascular bed, a half-circulatory time of less than 10 seconds. The rate of NO formation, measured as iron-nitrosyl and S-nitroso-hemoglobin and quantified by subtraction of the arterial from the venous levels with the difference being multiplied by blood flow, increased greatly during exercise, despite a significant decrease in the venous concentration of nitrite secondary to increasing blood flow diluting the regional nitrite concentration (FIG. 4A; P=0.006 for iron-nitrosyl-hemoglobin and P=0.02 for S-nitroso-hemoglobin by repeated measures ANOVA).

FIG. 4A depicts formation of iron-nitrosyl-hemoglobin (black squares) and S-nitroso-hemoglobin (red circles) during nitrite infusion at baseline, during nitrite infusion and during nitrite infusion with exercise, quantified by subtraction of the arterial from the venous levels and multiplying the result by blood flow. The formation of both NO-hemoglobin adducts was inversely correlated with hemoglobin-oxygen saturation in the human circulation during nitrite infusion (for iron-nitrosyl-hemoglobin p<0.0001, for S-nitroso-hemoglobin r=−0.45, p=0.04) (FIG. 4B). Hemoglobin oxygen saturation was measured from the antecubital vein by co-oximetry. Asterix in all figures signify P<0.05 by paired t test or repeated measures analysis of variance.

Figure 5A:
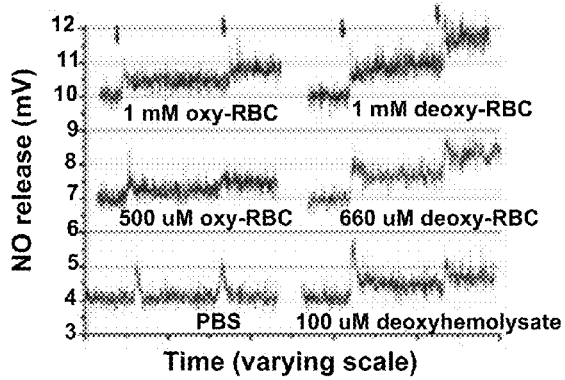
FIG. 5A shows NO release following nitrite injections into solutions of PBS ("PBS"), deoxygenated red blood cells ("deoxy-RBC"), and oxygenated red blood cells ("oxy-RBC").
Figure 5B:
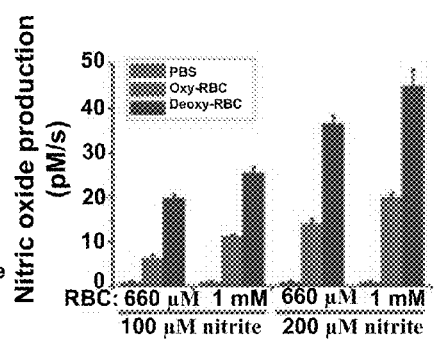
FIG. 5B shows the rate of NO formation from nitrite mixed with PBS (first bar in each set), and oxygenated and deoxygenated red blood cells (second and third bar in each set, respectively).

To determine whether free NO radical can form from the reaction of nitrite and deoxyhemoglobin, 100 and 200 μM nitrite was reacted with deoxygenated erythrocytes (5 mL volume containing a total of 660 and 1000 μM in heme) in a light protected reaction vessel purged with helium in-line with a chemiluminescent NO analyzer (Seivers, Boulder, Colo.). As shown in FIGS. 5A and 5B, the injection of nitrite into a solution of deoxygenated erythrocytes resulted in the liberation of NO into the gas phase. There was no release from nitrite in buffer control under the same conditions, and significantly less NO was released upon nitrite addition to oxygenated erythrocytes (21% and 100% oxygen). The observed rate (determined by the assessment of the area under the curve of increased steady-state NO generation following nitrite injection calculated over 120 seconds) of NO production in the 5 mL reaction volume was consistent with 47 μM NO production per second (corresponding to an estimated 300 to 500 μM NO production per second in whole blood). While NO formation rates in this experimental system may not be extrapolated to rates of NO formation in vivo, the experiments are consistent with two important concepts: 1) A fraction of free NO can escape auto-capture by the remaining heme groups; this is likely only possible because nitrite is only converted to NO by reaction with deoxyhemoglobin and its "leaving group" is the met(ferric)heme protein which will limit scavenging and inactivation of NO (Doyle et al., *J Biol Chem*, 256, 12393-12398, 1981); and 2) The rate of NO production is increased under anaerobic conditions, consistent with a nitrite-deoxyhemoglobin reaction.

Example 2

Cytoprotective Effects of Nitrite During Ischemia-Reperfusion of the Heart and Liver As demonstrated in Example 1, nitrite is reduced to NO by reaction with deoxyhemoglobin along the physiological oxygen gradient, a chemistry whose rate is oxygen and pH dependent and that potentially contributes to hypoxic vasodilation. Based on that unexpected discovery, we proposed that hypoxia-dependent NO production from nitrite in ischemic tissue might limit ischemia-reperfusion injury. This example provides a demonstration that infusions of sodium nitrite are effective to provide cytoprotection during ischemia-reperfusion of the heart and liver.

Although reperfusion of ischemic tissues provides oxygen and metabolic substrates necessary for the recovery and survival of reversibly injured cells, reperfusion itself actually results in the acceleration of cellular necrosis (Braunwald et al., *J. Clin. Invest.* 76:1713-1719, 1985). Ischemia-reperfusion is characterized by the formation of oxygen radicals upon reintroduction of molecular oxygen to ischemic tissues resulting in widespread lipid and protein oxidative modifications of cellular proteins, mitochondrial injury, and tissue apoptosis and necrosis (McCord et al., *Adv Myocardiol* 5:183-189, 1985). In addition, following reperfusion of ischemic tissues blood flow may not return uniformly to all portions of the ischemic tissues, a phenomenon that has been termed the "no-reflow" phenomenon (Kloner et al., *J Clin Invest* 54:1496-1508, 1974). Reductions in blood flow following reperfusion are thought to contribute to cellular injury and necrosis (Kloner et al., *J Clin Invest* 54:1496-1508, 1974). The sudden re-introduction of blood into ischemic tissue also results in a dramatic increase in calcium delivery to the previously ischemic tissue (i.e., "calcium paradox") resulting in massive tissue disruption, enzyme release, reductions in high energy phosphate stores, mitochondrial injury, and necrosis (Nayler, *Amer. J. Path.* 102:262, 1981; Shen et al., *Amer. J. Path* 67:417-440, 1972). Recent studies have also indicated that the ischemia-reperfusion injury is also characterized by an inappropriate inflammatory response in the microcirculation resulting in leukocyte-endothelial cell interactions that are mediated by the upregulation of both leukocyte and endothelial cell adhesion molecules (Lefer et al., *Cardiovasc Res* 32:743-751, 1996; Entman et al., *Faseb J* 5:2529-2537, 1991). Intensive research efforts have been focused on ameliorating various pathophysiological components of ischemia-reperfusion injury to limit the extent of tissue injury and necrosis.

NO, NO donors, and NO synthase activation or transgenic over-expression have been shown to exert protective effects on this process in a number of models (Lefer et al., *New Horiz* 3:105-112, 1995; Lefer et al., *Circulation* 88:2337-2350, 1993; Nakanishi et al., *Am J Physiol* 263:H1650-1658, 1992; Jones et al., *Am J Physiol Heart Circ Physiol* 286:H276-282, 2004; Jones et al., *Proc Natl Acad Sci USA* 100:4891-4896. 2003; Kanno et al., *Circulation* 101:2742-2748, 2000), but in other models appears harmful (Flogel et al., *J Mol Cell Cardiol* 31:827-836. 1999; Menezes et al., *Am J Physiol* 277: G144-151, 1999; Woolfson et al., *Circulation* 91:1545-1551, 1995; Schulz, R. et al., *Cardiovasc Res* 30:432-439, 1995). Evaluation of these studies suggests a critical effect of dose and duration of NO exposure, resulting in a narrow therapeutic safety window for NO in ischemia-reperfusion pathophysiology (Bolli, *J. Mol. Cell. Cardio.* 33:1897-1918, 2001; Wink et al., *Am J Physiol Heart Circ Physiol* 285:H2264-2276, 2003). An additional limitation is that NO formation from NO synthase requires oxygen as substrate, a molecule whose availability becomes limited during ischemia.

We therefore considered the use of nitrite in this context for the following reasons:
(1) It is a naturally occurring substance with no potentially toxic "leaving group",
(2) it is selectively reduced to NO in tissues with low oxygen tension and low pH (Bryan et al., *Proc Natl Acad Sci USA.*, 2004; Cosby et al., *Nat Med* 9:1498-1505, 2003; Nagababu et al., *J Biol Chem* 278:46349-46356, 2003; Tiravanti et al., *J Biol Chem* 279:11065-11073, 2004; Doyle et al., *J Biol Chem* 256:12393-12398, 1981; Luchsinger et al., *Proc Nati Acad Sci USA* 100:461-466, 2003),
(3) its activation does not require molecular oxygen (Cosby et al., *Nat Med* 9:1498-1505, 2003), and
(4) NO is known to maintain heme proteins in a reduced and liganded state (Herold et al., *Free Radic Biol Med* 34:531-545, 2003; Herold et al., *J Biol Inorg Chem* 6:543-555, 2001; Fernandez et al., *Inorg Chem* 42:2-4, 2003), limit free iron and heme mediated oxidative chemistry (Kanner et al., *Arch Biochem Biophys* 237: 314-321, 1985; Kanner et al., *Lipids* 20:625-628, 1985; Kanner et al., *Lipids* 27:46-49, 1992), transiently inhibit cytochome c oxidase and mitochondrial respiration (Tones et al., *FEBS Lett* 475:263-266, 2000; Brown et al., *FEBS Lett* 356:295-298, 1994; Cleeter et al., *FEBS Lett* 345:50-54, 1994; Rakhit et al., *Circulation* 103: 2617-2623, 2001), and modulate apoptotic effectors (Mannick et al., *Science* 284:651-654, 1999), all mechanisms that might participate in cytotoxicity following severe ischemia.

We evaluated the effects of nitrite therapy, compared with vehicle and nitrate controls, in well characterized murine models of hepatic and myocardial ischemia-reperfusion injury. The following description provides strong evidence for a profound protective effect of nitrite on cellular necrosis and apoptosis, which is believed to be mediated by a hypoxia-dependent bioconversion of nitrite to NO and nitros(yl)ated proteins.

Materials and Methods

Chemicals and Reagents: Sodium nitrite (S-2252) and sodium nitrate (S-8170) were obtained from the Sigma Chemical Co. (St. Louis, Mo.). Sodium nitrite and sodium nitrate were dissolved in phosphate buffered saline and the pH was adjusted to 7.4. In all experiments a final volume of 50 µL of sodium nitrite or sodium nitrate were administered to the mice to achieve final concentrations of circulating nitrite of 0.6 to 240 µM assuming a total circulating blood volume of 2 mL. Carboxy-PTIO [2-(4-Carboxyphenyl)-4,4,5,5-tetramethylimidazoline-1-oxyl-3-oxide potassium salt], a direct intravascular NO scavenger, was utilized to inhibit NO dependent effects following hepatic 1/R injury. Carboxy-PTIO (Alexis Biochemicals) was dissolved in phosphate buffered saline and administered intravenously at a dose of 1 mg/Kg in a volume of 50 µL at 30 minutes prior to hepatic ischemia. Zinc(II) Deuteroporphyrin IX-2,4-bisethyleneglycol (ZnDBG) (Alexis Biochemicals), a heme oxygenase-1 inhibitor was injected i.p. at a dose of 10 mg/Kg in a volume of 50 µL at 30 minutes prior to the induction of hepatic ischemia.

Animals: All of the mice utilized in the present studies were C57BL6/J at 8-10 weeks of age obtained from the Jackson Laboratories (Bar Harbor, Me.). In additional experiments of hepatic I/R injury we utilized mice completely deficient (−/−) in endothelial nitric oxide synthase (eNOS). eNOS−/− mice were originally generously donated from Dr. Paul Huang (Mass. General Hospital) and generated in our breeding colony at LSU-Health Sciences Center. eNOS−/− mice were utilized at 8-10 weeks of age.

Figure 6A:
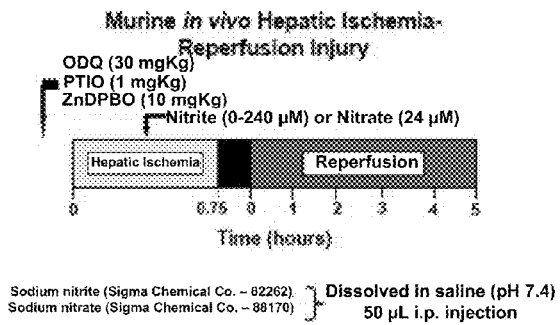
FIG. 6A illustrates the experimental protocol used for murine model of hepatic ischemia-reperfusion injury.

Hepatic Ischemia-Reperfusion (I/R) Protocol: The hepatic I/R protocol is depicted in FIG. 6A and has been described previously (Hines et al., *Biochem Biophys Res Commun* 284: 972-976, 2001; Hines et al., *Am J Physiol Gastrointest Liver Physiol* 284:G536-545, 2001). Mice were anesthetized with the combination of ketamine (100 mg/kg) and zylazine (8 mg/kg) and a midline laparotomy was performed to expose the liver. Mice were then injected with heparin (100 µg/kg, i.p.) to prevent blood clotting. The left lateral and median lobes of the liver were rendered ischemic by completely clamping the hepatic artery and the portal vein using microaneurysm clamps. This experimental model results in a segmental (70%) hepatic ischemia. This method of partial ischemia prevents mesenteric venous congestion by allowing portal decompression throughout the right and caudate lobes of the liver. The liver was then repositioned in the peritoneal cavity in its original location for 45 minutes. The liver was kept moist using gauze soaked in 0.9% normal saline. In addition, body temperature was maintained at 37° C. using a heat lamp and monitoring body temperature with a rectal temperature probe. Sham surgeries were identical except that hepatic blood flow was not reduced with a microaneurysm clamp. The duration of hepatic ischemia was 45 minutes in all experiments, following which the microaneurysm clamps were removed. The duration of hepatic reperfusion was 5 hours in the studies of serum liver transaminase levels (i.e., AST or ALT) and 24 hours for the studies of liver histopathology (such as hepatocellular infarction).

Liver Enzyme Determinations: Serum samples were analyzed for aspartate aminotransferase (AST) and alanine aminotransferase (ALT) using a spectrophotometric method (Sigma Chemical Co., St. Louis, Mo.) (Harada et al., *Proc Natl Acad Sci USA* 100:739-744, 2003). These enzymes are liver specific and are released from the liver during injury (Hines et al., *Biochem Biophys Res Commun* 284:972-976, 2001; Hines et al., *Am J Physiol Gastrointest Liver Physiol* 284:G536-545, 2001).

Liver Histopathology Studies: Histopathology of liver tissue was performed as previously reported (Hines et al., *Biochem Biophys Res Commun* 284:972-976, 2001). Liver tissue was fixed in 10% buffered formalin for 24 hours, embedded in paraffin, and 10 µM sections stained with hematoxylin and eosin. Histopathology scoring was performed in a double blinded manner on random high power fields using the following criteria:
 0—no hepatocellular damage,
 1—mild injury characterized by cytoplasmic vacuolization and focal nuclear pyknosis,
 2—moderate injury with dilated sinusoids, cytosolic vacuolization, and blurring of intercellular borders,
 3—moderate to severe injury with coagulative necrosis, abundant sinusoidal dilation, RBC extravasation into hepatic chords, and hypereosinophilia and margination of neutrophils,
 4—severe necrosis with loss of hepatic architecture, disintegration of hepatic chords, hemorrhage, and neutrophil infiltration.

Hepatocellular apoptosis was determined using the TUNEL staining kit from Roche according to the manufacturer's recommendations. Briefly, liver tissue from various treatments was fixed in buffered formalin and 10 µm sections were prepared. Sections were permeabilized on ice for 2 minutes and incubated in 50 µL TUNEL solution for 30 minutes at 37° C. Sections were then treated with 50 µL substrate solution for 10 min and mounted under glass coverslips. The number of apoptotic nuclei was determined from 5 random 40× fields per specimen. A total of six specimens per treatment group (16 slides per group) were analyzed and compared using one-way analysis of variance with Bonferroni's post-testing.

Myocardial Ischemia-Reperfusion (I/R) Protocol: Surgical ligation of the left main coronary artery (LCA) was performed similar to methods described previously (Jones et al., *Am J Physiol Heart Circ Physiol* 286:H276-282, 2004). Briefly, mice were anesthetized with intraperitoneal injections of ketamine (50 mg/kg) and pentobarbital sodium (50 mg/kg). The animals were then attached to a surgical board with their ventral side up. The mice were orally intubated with PE-90 polyethylene tubing connected to PE-240 tubing and then connected to a Model 683 rodent ventilator (Harvard Apparatus, Natick, Mass.). The tidal volume was set at 2.2 milliliters and the respiratory rate was set at 122 breaths per minute. The mice were supplemented with 100% oxygen via the ventilator side port. A median sternotomy was performed using an electric cautery and the proximal left main coronary artery was visualized and completely ligated with 7-0 silk suture mounted on a tapered needle (BV-1 ethicon). In the initial experiments of myocardial infarct size coronary occlusion was maintained for 30-minutes followed by removal of suture and reperfusion for 24 hours. In additional experiments of cardiac function, the proximal LCA was completely occluded for 45 minutes followed by suture removal and reperfusion for 48 hours. In these experiments, two-dimensional echocardiography was performed at baseline and again at 48 hours of reperfusion.

Myocardial Infarct Size Determination: At 24 hours of reperfusion, the mice were anesthetized as described previously, intubated, and connected to a rodent ventilator. A catheter (PE-10 tubing) was placed in the common carotid artery to allow for Evans Blue dye injection. A median sternotomy was performed and the left main coronary artery was re-ligated in the same location as before Evans Blue dye (1.2 mL of a 2.0% solution, Sigma Chemical Co.) was injected into the carotid artery catheter into the heart to delineate the ischemic zone from the nonischemic zone. The heart was rapidly excised and serially sectioned along the long axis in five, 1 mm thick sections that were then incubated in 1.0% 2,3,5-triphenyltetrazolium chloride (Sigma Chemical Co.) for 5 minutes at 37° C. to demarcate the viable and nonviable myocardium within the risk zone. Each of the five, 1 mm thick myocardial slices were weighed and the areas of infarction, risk, and nonischemic left ventricle were assessed by a blinded observer using computer-assisted planimetry (NIH Image 1.57). All of the procedures for the left ventricular area-at-risk and infarct size determination have been previously described (Jones et al., *Am J Physiol Heart Circ Physiol* 286:H276-282, 2004).

Echocardiographic Assessment of Left Ventricular Function: Transthoracic echocardiography of the left ventricle using a 15 MHz linear array transducer (15L8) interfaced with a *Sequoia* C256 (Acuson) was performed in additional groups of mice (n=9 vehicle and n=10 nitrite) subjected to 45 minutes of myocardial ischemia and 48 hours of reperfusion. Two-dimensional echocardiography was performed at baseline and at 48 hours of reperfusion as described previously (Jones et al., *Am J Physiol Heart Circ Physiol* 286:H276-282, 2004; Jones et al., *Proc Natl Acad Sci USA* 100:4891-4896. 2003). Ventricular parameters were measured using leading-edge technique. M-mode (sweep speed=200 mm/sec) echocardiograms were captured from parasternal, short and long-axis 2D views of the left ventricle (LV) at the mid-papillary level. LV percent fractional shortening (FS) was calculated according to the following equation: LV % FS= ((LVEDD−LVESD)/LVEDD)×100. All data were calculated from 10 cardiac cycles per experiment.

HO-1 Western Blot Analysis of homogenized liver tissue samples (50 μg total protein) was performed using mouse anti-HO-1 mAb (Stressgen, Victoria, BC) at a 1:3,000 dilution and goat anti-mouse secondary Ab (Amersham Biosciences, Piscataway, N.J.) at a 1:3,000 dilution.

Blood and Tissue Nitrite Determination: For blood nitrite measurements, 160 μL of whole blood was mixed with 40 μL of a nitrite stabilizing solution containing 80 mM ferricyanide, 20 mM N-ethylmaleimide (NEM), 200 μL diethylenetriaminepentaacetic acid (DTPA), and 0.2% NP-40 (concentrations provided are after mixing with whole blood). The nitrite in whole blood was then measured using tri-idodide-based reductive chemiluminescence as previously described and validated (Gladwin et al., *J Biol Chem* 21:21, 2002; Yang et al., *Free Radic Res* 37:1-10, 2003).

Liver tissue was homogenized using an amended protocol published by Bryan and colleagues (Bryan et al., *Proc Natl Acad Sci USA.*, 2004). Harvested liver tissue was blotted dry on filter paper, weighed, and homogenized immediately in ice-cold NEM (10 mmol/L)/DTPA (2 mmol/L) containing buffer (3:1 dilution—w/v). The buffer/tissue mix was then homogenized with a Wheaton glass-glass homogenizer. Tissue homogenates were kept on ice and analyzed within 5 minutes. The homogenate was subsequently either injected directly into triiodine to measure the sum of nitrite, mercury stable (Rx—NO) and mercury-labile (RS—NO) NO-adducts. To determine the levels of specific NO-adducts (Rx—NO and RS—NO), the sample was reacted with and without 5 mM mercuric chloride (RS—NO becomes nitrite in presence of mercuric chloride and Rx—NO is stable) and both treated with acid sulfanilamide (0.5%) to eliminate nitrite.

Statistical Analyses: Data were analyzed by two-way analysis of variance (ANOVA) with post hoc Bonferroni analysis using StatView software version 5.0 (SAS Institute, Carey, N.C.). Data are reported as means±standard error of the mean (SEM) with differences accepted as significant when $p<0.05$.

Results

Figure 6B:
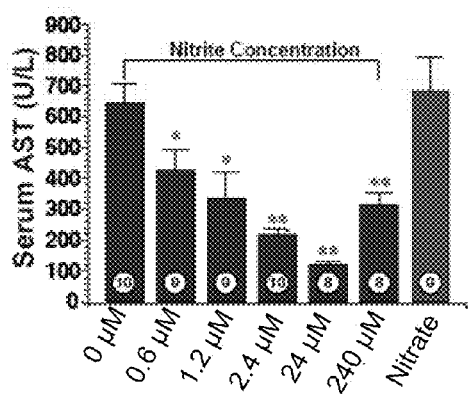
FIG. 6B is a graph showing serum AST levels in mice following hepatic ischemia-reperfusion. *$p<0.05$ vs. vehicle (0 µM) and **$p<0.01$ vs. vehicle (0 µM)
Figure 6C:
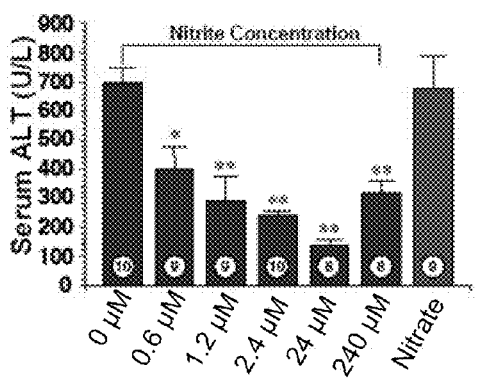
FIG. 6C is a graph showing serum ALT levels in mice following hepatic ischemia-reperfusion. *$p<0.05$ vs. vehicle (0 µM) and $p<0.01$ vs. vehicle (0 µM)
Figure 6D:
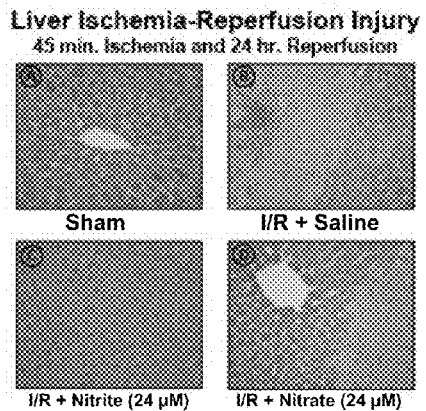
FIG. 6D is a representative photomicrographs of hepatic histopathology following 45 minutes of ischemia and 24 hours of reperfusion.
Figure 6E:
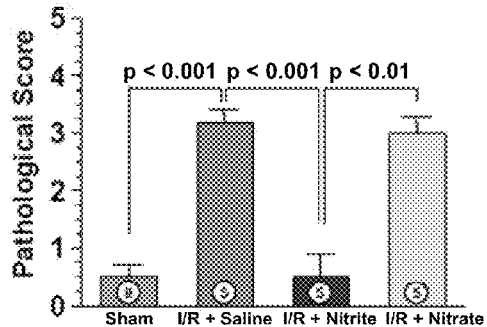
FIG. 6E is a bar graph showing pathological scoring of hepatic tissue samples following 45 minutes of ischemia and 24 hours of reperfusion.
Figure 6F:
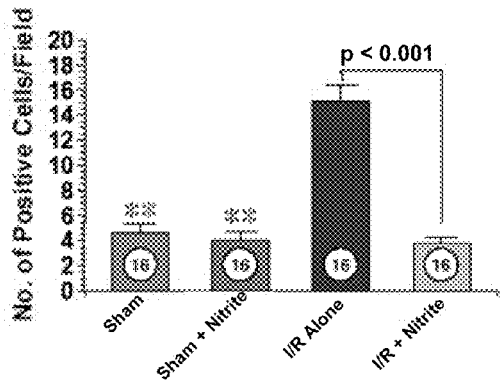
FIG. 6F is a bar graph showing hepatocellular apoptosis as measured by TUNEL staining following 45 minutes of ischemia and 24 hours of reperfusion. $p<0.001$ vs. I/R alone group

Intraperitoneal Nitrite Limits Hepatic Ischemia-Reperfusion (I/R) Injury:

Intraperitoneal delivery of 1.2-480 nmoles of sodium nitrite (0.6 μM to 240 μM estimated final concentration in a 2 mL total blood volume of the mouse) during hepatic ischemia dose-dependently limited serum elevations of liver transaminases, aspartate amino transferase (AST) and alanine amino transferase (ALT) (FIGS. 6B and 6C), with a peak effect occurring at a calculated systemic concentration of 24 μM (48 nmoles added nitrite). In sharp contrast, treatment with saline or sodium nitrate (48 nmoles) did not exert any protective effects in the setting of hepatic I/R injury. Additional studies were performed to evaluate the effects of nitrite treatment on hepatocellular injury in mice following in vivo hepatic ischemia (45 minutes) and more prolonged reperfusion (24 hours; FIGS. 6D, 6E, and 6F). The administration of nitrite at a final blood concentration of 24 μM (48 nmoles) significantly reduced hepatocellular injury at 24 hours of reperfusion compared with saline and nitrate treated animals. In addition, nitrite therapy also significantly ($p<0.001$) attenuated the extent of hepatocellular apoptosis following 45 minutes of hepatic ischemia and 24 hours of reperfusion (FIG. 6F). The extent of hepatic cell apoptosis in nitrite treated animals subjected to I/R was similar to that observed in sham operated control animals (p=NS).

Figure 7A:
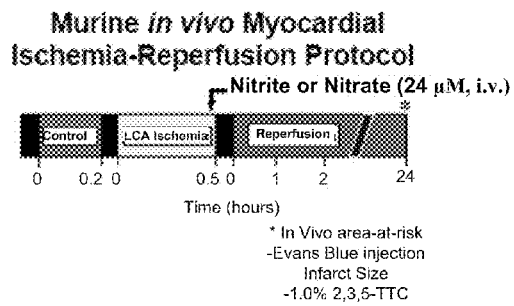
FIG. 7A illustrates the experimental protocol used for myocardial ischemia-reperfusion studies in mice.
Figure 7B:
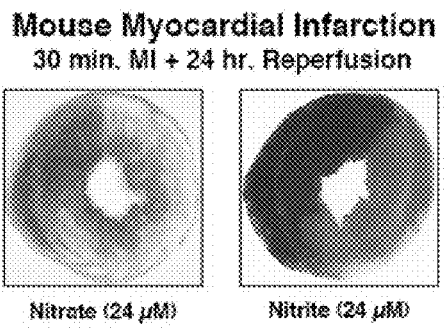
FIG. 7B is a representative photomicrographs of the murine hearts following 30 minutes of myocardial ischemia and reperfusion.
Figure 7C:
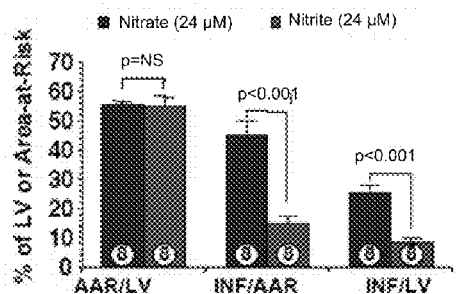
FIG. 7C is a bar graph comparing myocardial area-at-risk (AAR) per left ventricle (LV), infarct size (INF) per AAR, and infarct per left ventricle in mice treated with nitrate or nitrite.

Intraventricular Nitrite Limits Myocardial Ischemia-Reperfusion Injury:

To determine whether the potent cytoprotective effects of nitrite on liver ischemia-reperfusion injury were generalizable to other organ systems, studies were next performed to evaluate the potential cardioprotective effects of acute nitrite therapy in the setting of coronary artery occlusion and reperfusion. The experimental protocol for the myocardial I/R studies is depicted in FIG. 7A. Administration of nitrite (48 nmoles) into the left ventricular cavity at 5 minutes prior to reperfusion significantly ($p<0.001$) limited myocardial infarct size (FIGS. 7B and 7C) compared to 48 nmoles nitrate treatment. Despite similar myocardial areas-at-risk (p=NS between groups), myocardial infarct size per area-at-risk and per left ventricle were both reduced by 67% with nitrite therapy compared to nitrate.

Figure 7D:
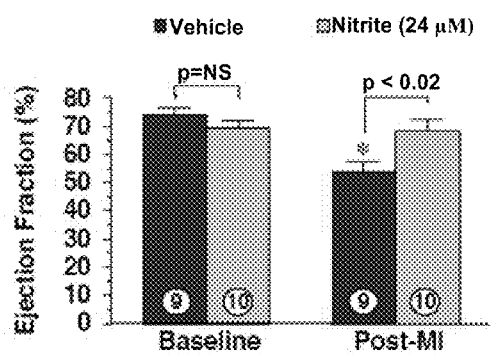
FIG. 7D is a bar graph comparing myocardial ejection fraction at baseline and following 45 minutes of myocardial ischemia and 48 hours of reperfusion.
Figure 7E:
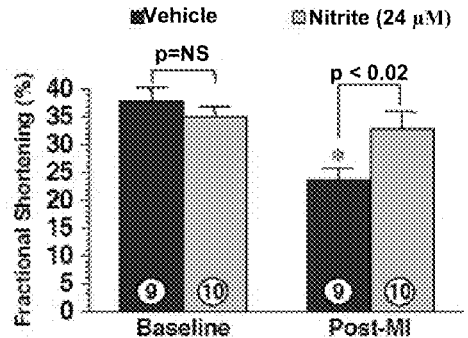
FIG. 7E is a bar graph comparing left ventricular fractional shortening at baseline and following 45 minutes of myocardial ischemia and 48 hours of reperfusion.

In additional studies, mice were subjected to 45 minutes of myocardial ischemia and 48 hours of reperfusion to evaluate the effects of nitrite treatment on left ventricular performance (FIGS. 7D and 7E). In these studies, both myocardial ejection fraction (FIG. 7D) and myocardial fractional shortening (FIG. 7E) were measured using two-dimensional echocardiography at baseline and following myocardial infarction and reperfusion. Myocardial ejection fraction was similar between the vehicle and nitrite treated study groups at baseline. Following myocardial infarction and reperfusion, ejection fraction was significantly ($p<0.001$ vs. baseline value) lower in the saline vehicle group, yet remained essentially unchanged in the nitrite treated animals (p=NS vs. baseline). Additionally, ejection fraction was significantly ($p<0.02$) greater in the nitrite group compared to the vehicle group. Similar observations were made for fractional shortening with no significant group differences at baseline. However, following myocardial infarction and reperfusion, left ventricular fractional shortening was significantly ($p<0.001$ vs. baseline) depressed in the vehicle group, but not in the nitrite group (p=NS vs. baseline) and was significantly ($p<0.02$) greater in the nitrite group compared to the vehicle group.

Figure 8B:
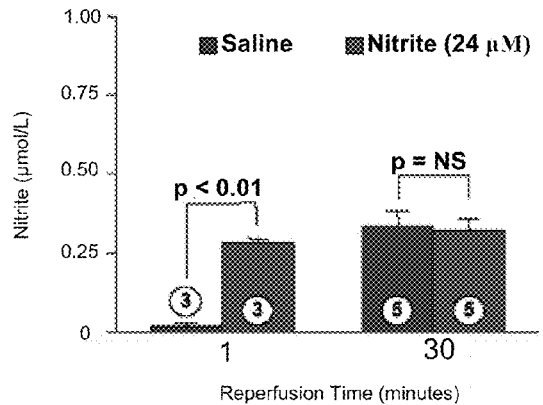
FIG. 8B shows liver tissue nitrite levels in mice (n=3-5 per group) subjected to hepatic ischemia-reperfusion (I/R) injury.
Figure 8A:
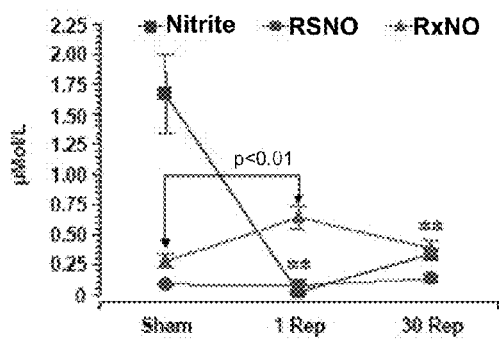
FIG. 8A shows blood nitrite, RSNO, and RxNO levels (µmol/L) in animals (n=3-5 per group) subjected to sham hepatic ischemia-reperfusion (I/R) or hepatic ischemia and either 1 or 30 minutes of reperfusion. **$p<0.001$ vs. sham
Figure 8C:
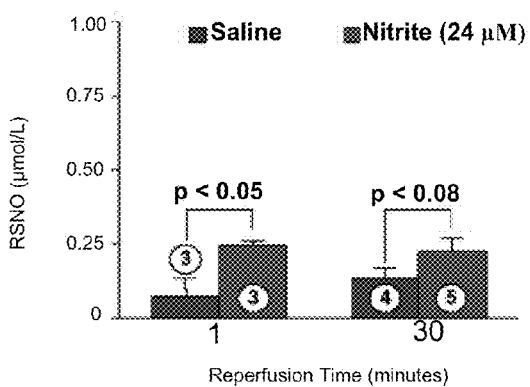
FIG. 8C shows liver tissue RSNO levels (µmol/L) in mice (n=3-5 per group) subjected to hepatic ischemia and varying periods of reperfusion.
Figure 8D:
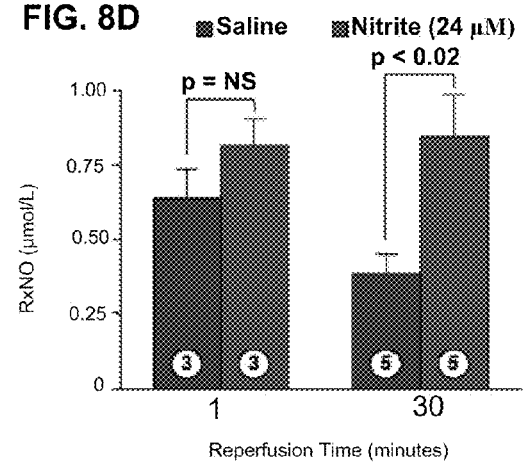
FIG. 8D shows hepatic tissue RxNO levels (µmol/L) following hepatic ischemia and reperfusion in mice (n=3-5 per group).

Nitrite-Mediated Cytoprotection is Associated with an Acute Ischemic Reduction of Nitrite to NO and S- and N-Nitrosated Proteins within the Liver:

Consistent with previously described reduction of nitrite to NO and 5-nitrosothiols in a reaction with deoxyhemoglobin and deoxygenated heme proteins (Bryan et al., *Proc Natl Acad Sci USA.*, 2004; Cosby et al., *Nat Med* 9:1498-1505, 2003; Nagababu et al., *J Biol Chem* 278:46349-46356, 2003; Doyle et al., *J Biol Chem* 256:12393-12398, 1981), one minute after reperfusion the levels of nitrite in the livers of saline (control) treated mice subjected to ischemia decreased from 1.75 μM to undetectable ($p<0.001$ vs. sham group) and levels of mercury stable NO modified proteins (likely N-nitrosamines and iron-nitrosyl proteins; RxNO) increased to approximately 750 nM (FIG. 8A; $p<0.001$). Interestingly, with nitrite treatment there was a significant ($p<0.01$ vs. saline treated controls) increase in post-reperfusion liver levels of nitrite (FIG. 8B), S-nitrosothiols (FIG. 8C) and N-nitrosamines (FIG. 8D) in the nitrite treated mice. These data are consistent with the thesis that nitrite is bioactivated during hypoxic stress and consistent with recent studies of Bryan and colleagues demonstrating an acute conversion of tissue nitrite to RSNO and RxNO after a systemic anoxic insult (*Proc Natl Acad Sci USA.*, 2004). The low levels of nitrite that are cytoprotective (1.2 nmoles at lowest dose—FIGS. 6B and 6C) and the reductive decomposition of "native" liver nitrite in the saline treated control animals (FIG. 8A) suggest that this may be a natural mechanism for hypoxic NO production and cytoprotection. Consistent with the near-physiological amounts of nitrite given, blood nitrite levels were not significantly elevated (594±83 nM to 727±40 nM; n=3; p=0.16) in mice treated with 48 nmoles of nitrite, the most effective dose.

Figure 9A:
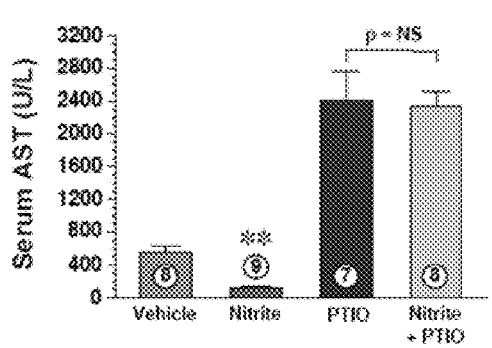
FIG. 9A is a graph, comparing serum aspartate aminotransferase (AST) levels in mice receiving saline vehicle, nitrite (24 µM), the nitric oxide (NO) scavenger PTIO, or nitrite (24 µM)+PTIO. **$p<0.01$ vs. the vehicle group.
Figure 9B:
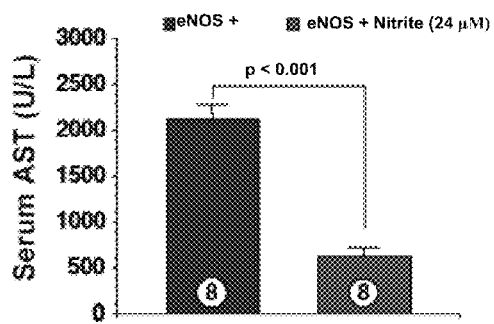
FIG. 9B is a graph comparing serum levels of AST in eNOS deficient (−/−) mice receiving saline vehicle or sodium nitrite (24 µM).
Figure 9C:
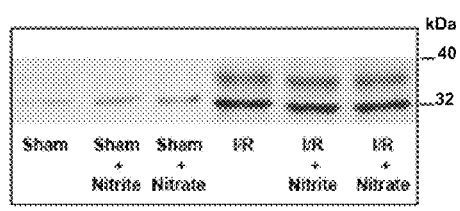
FIG. 9C is an image showing hepatic protein levels of heme oxygenase-1 (HO-1) determined using western blot analysis in sham operated animals and in animals subjected to hepatic ischemia (45 minutes) and reperfusion (5 hours).
Figure 9D:
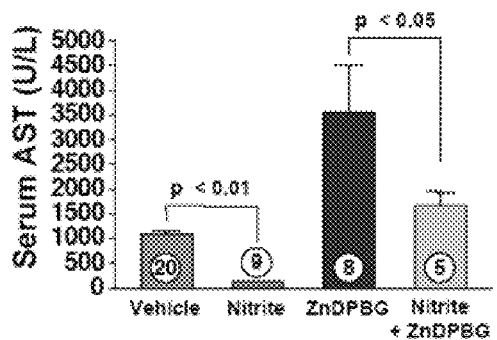
FIG. 9D is a graph comparing serum AST levels in mice treated with nitrite (24 µM) or the HO-1 inhibitor zinc deuteroporphyrin bis glycol (ZnDPBG) in the setting of hepatic ischemia reperfusion injury.

Cytoprotective Effects of Nitrite are NO Dependent, NO Synthase Independent and Heme Oxygenase Independent:

Further supporting a mechanism involving the hypoxic reduction of nitrite to NO, the NO inhibitor PTIO completely inhibited protective effects of nitrite in full factorial design experiments (FIG. 9A). In contrast, significant nitrite cytoprotection was observed in endothelial NO synthase (eNOS) deficient mice (FIG. 9B; p<0.001), suggesting that NO production from nitrite during ischemia-reperfusion is eNOS independent. While heme oxygenase 1 protein expression is significantly induced following ischemia-reperfusion in this model, and appears to confer protection (FIGS. 9C and 9D), in mice pre-treated with ZnDPBG (a specific and potent heme oxygenase 1 inhibitor) nitrite significantly limited tissue injury suggesting a heme oxygenase-independent effect (FIG. 9C; p<0.05).

Discussion

In this example, nitrite treatment significantly increased the levels of liver nitrite and nitros(yl)ated species (RSNO and RXNO), compared with saline and nitrate treated controls, and conferred a dramatic dose-dependent cytoprotective effect, limiting necrosis, apoptosis, and preserving organ function. Remarkably, the levels of nitrite added were near-physiological, with a protective effect observed at even 1.2 nmoles added nitrite (a calculated blood level of 600 nM), suggesting that this may represent an endogenous protective mechanism that buffers severe metabolic or pathophysiological stress.

Recent data suggest that nitrite concentrations vary between blood and different organs and are typically in the high nanomolar to low micromolar range. However, until recently the high concentrations required to vasodilate aortic ring preparations led to its dismissal as an important biologically active molecule. Indeed, Furchgott et al. (*J. Pharmaco. Exper. Thera.* 108:129-143, 1953) demonstrated in 1953 that 100 µM nitrite stimulated vasodilation of aortic ring preparations, a process later shown to be mediated by activation of soluble guanylate cyclase (Kimura et al., *J Biol Chem* 250: 8016-8022, 1975; Mittal et al., *J Biol Chem* 253:1266-1271, 1978; Ignarro et al., *Biochim Biophys Acta* 631:221-231, 1980; Ignarro et al., *Pharmacol Exp Ther* 218:739-749, 1981). From a physiological standpoint, the in vivo conversion of nitrite to NO was thought to be limited to the stomach and severely ischemic heart, where acidic reduction or disproportionation at very low pH produces gastric mucosal vasodilation (Gladwin et al., *J Clin Invest* 113:19-21, 2004; Bjorne et al., *J Clin Invest* 113:106-114, 2004) and apparent cardiac tissue injury and heme iron-nitrosylation (at high nitrite concentrations in ischemic ex vivo heart preparations; Tiravanti et al., *J Biol Chem* 279:11065-11073, 2004), respectively. While xanthine oxidoreductase dependent nitrite reduction can occur at very low oxygen tensions, NO production from this system is only detectable in the presence of high concentrations of superoxide dismutase (Li et al., *J Biol Chem* 279:16939-16946, 2004; Li et al., *Biochemistry* 42:1150-1159, 2001).

As described in FIG. 6 and Cosby et al. (*Nat Med* 9:1498-1505, 2003), infusions of sodium nitrite into the human circulation produced significant vasodilation at both pharmacological and near-physiological concentrations. The bioactivation of nitrite appeared to be mediated by a nitrite reductase activity of deoxygenated hemoglobin, ultimately forming NO and iron-nitrosylated hemoglobin, and to a lesser extent S-nitrosated protein species. Based on these data, a role for circulating nitrite in mediating hypoxic vasodilation was proposed, with the oxygen sensor in this case being hemoglobin (Cosby et al., *Nat Med* 9:1498-1505, 2003). It is now proposed that a similar nitrite reductase activity of deoxyhemoglobin, deoxymyoglobin and/or other deoxygenated heme proteins, accounts for the formation of nitros(yl)ated proteins and apparent NO-dependent cytoprotection observed during liver and cardiac ischemia in the present example.

Though the precise mechanism of how nitrite confers tissue protection is unclear, a critical role for NO is implicated from data shown in FIGS. 3 and 9A. Previous studies of NO and ischemia-reperfusion have yielded conflicting reports regarding the effects of NO on the severity of I/R injury, with some studies suggesting that NO actually contributed to reperfusion injury (Woolfson et al., *Circulation* 91:1545-1551, 1995; Wink et al., *Am J Physiol Heart Circ Physiol* 285: H2264-2276, 2003). Our laboratory has previously demonstrated that NO donors as well as the NO precursor, L-arginine, protect against myocardial I/R injury (Lefer et al., *New Horiz* 3:105-112, 1995; Nakanishi et al., *Am J Physiol* 263: H1650-1658, 1992; Pabla et al., *Am J Physiol* 269:H1113-1121, 1995). More recently, we demonstrated that the severity of myocardial I/R injury is markedly exacerbated in eNOS-/- mice (Jones et al., *Am J Physiol* 276:H1567-1573, 1999) whereas mice with eNOS overexpression are protected against myocardial infarction and subsequent congestive heart failure (Jones et al., *Am J Physiol Heart Circ Physiol* 286:H276-282, 2004; Jones et al., *Proc Natl Acad Sci USA* 100:4891-4896. 2003; Jones et al., *Am J Physiol* 276:H1567-1573, 1999).

Conflicting data on the effects of NO on ischemia-reperfusion injury may be related to the dose of NO and the conditions during ischemia and reperfusion (Bolli, *J. Mol. Cell. Cardio.* 33:1897-1918, 2001). It is now well appreciated that very high, non-physiological levels of NO (i.e., high micromolar and millimolar) actually promote cellular necrosis and apoptosis (Dimmeler et al., *Nitric Oxide* 4:275-281, 1997), while the demonstrated cytoprotective effects of NO typically involve nanomolar or low micromolar concentrations of NO (Lefer et al., *New Horiz* 3:105-112, 1995; Lefer et al., *Circulation* 88:2337-2350, 1993; Bolli, *J. Mol. Cell. Cardio.* 33:1897-1918, 2001). Additionally, studies investigating NO and NO-releasing agents under in vitro conditions of I/R have consistently reported deleterious effects of NO (Bolli, *J. Mol. Cell. Cardio.* 33:1897-1918, 2001), in contrast to in vivo studies of I/R that reported beneficial effects of NO therapy (Lefer et al., *New Horiz* 3:105-112, 1995; Lefer et al., *Circulation* 88:2337-2350, 1993). How NO mediates protection is also not clear, with multiple mechanisms being reported, including sGC activation, inhibition of cytochrome C oxidase and inhibition of deleterious mitochondrial calcium uptake (Tones et al., *FEBS Lett* 475:263-266, 2000; Brown et al., *FEBS Lett* 356:295-298, 1994; Cleeter et al., *FEBS Lett* 345: 50-54, 1994; Rakhit et al., *Circulation* 103:2617-2623, 2001). While these data suggest that the effects of nitrite occur secondary to NO formation, the ultimate mechanism of nitrite-dependent cytoprotection is currently unknown (Luchsinger et al., *Proc Natl Acad Sci USA* 100:461-466, 2003; Fernandez et al., *Inorg Chem* 42:2-4, 2003; Han et al., *Proc Natl Acad Sci USA* 99:7763-7768, 2002; Crawford et al., *Blood* 101:4408-4415, 2003).

An intriguing possibility is the intermediate formation of S-nitrosothiols, known to form via reactions of nitrite with deoxyhemoglobin and possibly tissue heme proteins (Bryan et al., *Proc Natl Acad Sci USA.,* 2004; Cosby et al., *Nat Med* 9:1498-1505, 2003; Nagababu et al., *J Biol Chem* 278:46349-46356, 2003). Consistent with hypoxia dependent formation of S-nitrosothiols in red blood cells and tissues from nitrite, hepatic levels of these species were significantly higher following reperfusion (one-to-thirty minutes) in livers exposed to ischemia and nitrite. Within the relative reductive environment intracellularly, S-nitrosothiols formed via nitrite readily will be reduced to NO and activate sGC. Alternatively, S-nitrosation and subsequent effects on activity of critical proteins important in I/R induced injury and apoptotic cell death may lead to protection (Mannick et al., *Science* 284:651-654, 1999).

In addition, the data reported here reveal a dynamic regulation of hepatic RxNO's, a pool of mercury stable NO-modified proteins that include N-nitrosamines and iron-nitrosyls (Bryan et al., *Proc Natl Acad Sci USA.,* 2004; Gladwin et al., *J Biol Chem* 21:21, 2002; Rassaf et al., *Free Radic Biol Med* 33:1590-1596, 2002), during ischemia-reperfusion. In saline treated groups, RxNO levels increase at 1 minutes of reperfusion and then decrease after 30 minutes reperfusion, whereas sustained elevation in RxNO levels are observed in nitrite treated mice, suggesting that maintenance of RxNO's could be important in protecting tissues from I/R injury.

In conclusion, the data presented in this example demonstrate a remarkable function for the relatively simple inorganic anion nitrite as a potent inhibitor of liver and cardiac ischemia-reperfusion injury and infarction, as shown in a mouse model system. The effects of nitrite appear NO-dependent, with a rapid conversion of nitrite to NO and nitros(yl)ated proteins following reperfusion. Considering the known safety of nitrite as a naturally occurring anion and as an FDA approved therapeutic for cyanide poisoning, these data evince a novel, safe, and inexpensive therapy for ischemia-reperfusion injury. Such a therapy could be used to prevent or modulate organ dysfunction following, for instance, coronary and peripheral vasculature reperfusion, high risk abdominal surgery (such as aortic aneurism repair that leads to renal acute tubular necrosis), cardiopulmonary resuscitation, and perhaps most importantly, solid organ transplantation.

Example 3

Inhaled Nebulized Nitrite is a Hypoxia-Sensitive NO-Dependent Selective Pulmonary Vasodilator This example provides a description of use of inhaled, nebulized nitrite (specifically, sodium nitrite) to treat neonatal pulmonary hypertension.

Based on the results presented above, it is now known that the blood anion nitrite contributes to hypoxic vasodilation via a heme-based, nitric oxide (NO) generating reaction with deoxyhemoglobin and potentially other heme proteins. This biochemical reaction can be harnessed for the treatment of neonatal pulmonary hypertension, an NO-deficient state characterized by pulmonary vasoconstriction, right-to-left shunt pathophysiology, ventilation/perfusion inhomogeneity and systemic hypoxemia. As shown in this example, inhaled sodium nitrite was delivered by aerosol to newborn lambs with hypoxic and normoxic pulmonary hypertension. Inhaled nitrite elicited a rapid and sustained reduction (~60%) in hypoxia induced pulmonary hypertension, a magnitude approaching that of the effects of 20 ppm NO gas inhalation and which was associated with the immediate appearance of increasing levels of NO in expiratory gas. Pulmonary vasodilation elicited by aerosolized nitrite was deoxyhemoglobin- and pH-dependent and was associated with increased blood levels of hemoglobin iron-nitrosylation. Significantly, from a therapeutic standpoint, short term delivery of nitrite, dissolved in saline, via nebulization produced selective and sustained pulmonary vasodilation with no appreciable increase in blood methemoglobin levels. These data support the paradigm that nitrite is a vasodilator acting via conversion to NO, a process coupled to hemoglobin deoxygenation and protonation, and further evince a novel, simple and inexpensive therapy for neonatal pulmonary hypertension.

The effect of nebulized sodium nitrite versus saline, or inhaled NO, on both hypoxia-induced and drug-induced pulmonary hypertension was compared in newborn lambs. As described in this example, inhaled nitrite forms expired NO gas and circulating iron-nitrosyl-hemoglobin, and selectively vasodilates the pulmonary circulation. This vasoactivity is associated with the level of hemoglobin desaturation and blood pH in the physiologic range, supporting the physiological and therapeutic paradigm of hemoglobin as a deoxygenation-linked nitrite reductase.

Methods

Animal protocols were approved by the Institutional Animal Research Committee of Loma Linda University and were in accordance with the National Institutes of Health guidelines for use of experimental animals.

Animal Preparation:

Following induction of anesthesia with intravenous thiopental sodium (20 mg/Kg), the newborn lambs were orotracheally intubated and anesthesia maintained with 1% halothane until catheters were placed surgically. Thereafter halothane was discontinued and anesthesia maintained with morphine (0.1 mg/kg/hr). After paralysis with vecuronium (0.1 mg/kg/hr) the lungs were mechanically ventilated with initial settings of pressures: 22/6 cm $H_2O$, frequency: 25 breaths per minute, $FiO_2$: 0.21, and inspiratory time: 0.6 seconds (Sechrist Model 100, Sechrist Industries, Anaheim Calif., USA). Initially and throughout the normoxic experiments, ventilator settings of frequency, peak inspiratory pressure, and $FiO_2$ were adjusted to maintain $SaO_2$>95%, $PaO_2$ at 90-150 Ton, and $PaCO_2$ at 35-45 Torr.

A catheter was placed in the right brachial artery to sample pre-ductal blood for gases and chemical analysis. A pediatric thermodilution catheter was passed through a femoral vein to the pulmonary artery to measure cardiac output, pulmonary artery and pulmonary capillary wedge pressure (5.0 Pediatric Swan-Ganz® thermodilution catheter, Baxter Healthcare Corporation, Irvine, Calif., USA).

Catheters were placed in the femoral artery and vein for monitoring blood pressure, heart rate, and for administration of fluids and drugs. A thermocouple was placed in the femoral vein to monitor core-body temperature which was maintained at 39 C by using a warming blanket and heat lamp throughout the experiments.

After completion of the experiments, the lambs were euthanized with a proprietary euthanasia solution (Euthasol, Western Medical Supply, Arcadia, Calif., USA). In selected experiments necropsy was performed to verify the position of catheters (which were correctly positioned in all cases) and to determine that the ductus arteriosus was closed (which was closed in all cases).

Hemodynamic Measurements:

Mean arterial pressure, mean pulmonary artery pressure, and central venous pressure were measured continuously, and pulmonary capillary wedge pressure was measured intermittently by using calibrated pressure transducers (COBE Laboratories, Lakewood, Colo.) zeroed at the midthoracic level. Cardiac output was measured at 15-minute intervals throughout the studies by thermodilution using a Com-2 thermodilution module (Baxter Medical, Irvine, Calif., USA). Five-ml injections of ice-cold saline were used. Determinations were carried out in triplicate and results were averaged for each sampling time point. Pulmonary vascular resistance and systemic vascular resistance were calculated by using standard formulas.

Blood Gas and Methemoglobin Analysis:

Arterial and mixed venous pH, $PCO_2$, and $PO_2$ were measured in blood samples (0.3 ml) collected at intervals throughout the experiments. Blood gases were measured (ABL3, Radiometer, Copenhagen, Denmark) and oxyhemoglobin saturation and hemoglobin concentration were measured using a hemoximeter (OSM2 Hemoximeter, Radiometer, Copenhagen, Denmark). Arterial and mixed venous methemoglobin concentrations were analyzed by photometry with the OSM2 Hemoximeter using the same arterial sample as in the blood gas determinations.

Delivery of Aerosolized Nitrite, Saline, or NO Gas:

Five milliliters of either aqueous sodium nitrite (1 mM solution) or saline were placed in a jet nebulizer (Hudson RCI Micro Mist Nebulizer (Hudson Respiratory Care; Temecula, Calif.), driven at a constant flow rate of 8 U/minute in all experiments. The sodium nitrite solution was nebulized at a rate of 270 µmol/minute. Aerosols were delivered to the inspiration loop of the ventilator. Using a jet nebulizer, it is generally thought that <10% of a nebulized drug deposits in the lung (Coates et al., Chest 119, 1123-30, 2001). This is the result of the dead volume of the nebulizer and the loss of drug during the expiratory phase. Lung deposition depends on particle size distribution, which is under the influence of air flow, filling volume, drug solution, and ambient temperature (Flavin et al., Pediatr Pulmonol 2, 35-9, 1986; Suarez & Hickey, Respir Care 45, 652-66, 2000; Clay et al., Thorax 38, 755-9, 1983; Clay et al., Lancet 2, 592-4, 1983). This is a simple, inexpensive, and widely available clinical nebulizer system, though other systems could be used.

NO gas was introduced into the inspiratory limb of the breathing circuit. The inspired concentration of NO was continuously measured by chemiluminescence (CLD 700 AL, Eco Physics Inc, All Arbor, Mich.) in the inspiratory limb of the ventilator loop.

Inhalation of Nitrite or Saline Aerosols During Hypoxic-Induced Pulmonary Vasoconstriction.

Seven lambs were studied in order to demonstrate that nebulized nitrite is a selective pulmonary vasodilator in hypoxic newborn lambs. After anesthesia and instrumentation, the lambs were allowed to recover for 30 to 90 minutes while relevant hemodynamic parameters were monitored. After baseline measurements were obtained, a 30-minute period of pulmonary hypertension was induced by decreasing the $FiO_2$ of the inspired gas to 0.12 for 30 minutes. Ten minutes after initiation of hypoxia, either saline or sodium nitrite aerosols were administered for the remainder of the hypoxic period. After a one-hour recovery period, a second 30-minute period of hypoxia was induced again with either saline or sodium nitrite aerosols administered during the last 20 minutes. Arterial blood samples for blood gases and analytical assays were drawn and cardiac output measurements were performed at regular intervals.

Inhalation of Nitrite During U46619-Induced Pulmonary Hypertension in Normoxic Conditions.

Six additional lambs were studied in order to evaluate the effects of nitrite nebulization on normoxic pulmonary hypertension. Stable normoxic pulmonary hypertension was induced by an infusion of a stable endoperoxide analog of thromboxane (U46619-9, 11-dideoxy-11α-epoxymethano-prostaglandin $F_{2\alpha}$, Cayman Chemicals, All Arbor, Mich.). The drug was dissolved in saline and was administered at a rate of 2 µg/kg/min into the femoral venous catheter for 30 minutes. Nitrite was nebulized for inhalation during the last 20 minutes of the infusion (FIG. 11).

Comparison of Inhaled Nitrite and NO Gas During Hypoxic-Induced Pulmonary Vasoconstriction: Efficacy and Duration of Effect.

This protocol was designed to compare the efficacy of nitrite with the clinical standard, 20 ppm inhaled NO gas. This concentration of NO gas is at the upper end of the therapeutic dose given to infants with primary pulmonary hypertension (Kinsella & Abman, Semin Perinatol 24, 387-95, 2000; Kinsella et al., Lancet 340, 819-20, 1992), and has also been shown to be effective in reversing hypoxic vasoconstriction in newborn lambs (Frostell et al., Circulation 83, 2038-47, 1991). A second purpose was to determine the duration of effect of a short nitrite nebulization versus NO gas inhalation on hemodynamic and physiological measurements during prolonged hypoxic-induced pulmonary vasoconstriction. After baseline measurements were performed, the lambs were made hypoxic as described above for 35 minutes. Ten minutes after initiation of hypoxia, a 20-minute period of NO gas inhalation was initiated (20 ppm), with continuation of hypoxia for 5 minutes after cessation of NO gas delivery. Lambs were then allowed to recover for one hour. Again, after baseline measurements were made, a second 90-minute period of hypoxia was initiated. Ten minutes after initiation of hypoxia, sodium nitrite aerosol was administered for 20 minutes, with continuation of hypoxia for 60 minutes after cessation of nitrite aerosolization (FIG. 13).

Measurement of Exhaled NO.

Exhaled NO concentration was measured with a chemiluminescence NO analyzer (NOA 280, Sievers Instruments, Inc., Boulder, Colo.). The chemiluminescence analyzer was calibrated with NO-free air and NO gas (45 parts per million) according to the manufacturer's recommendations. NO was sampled though a Teflon sidearm attached to a sampling port at the proximal end of the endotracheal tube through which flow passed to the analyzer at 250 ml/min.

In selected early experiments, nitrite was nebulized through a ventilator circuit with no lamb connected while NO was measured with the chemiluminescence NO analyzer. In no experiments did nitrite nebulization through the disconnected circuit result in an increase in NO concentration in the ventilated air.

Measurement of Plasma Nitrite and Iron-Nitrosyl-Hemoglobin.

Blood was drawn from both the brachial artery and central venous catheter and rapidly processed. Plasma was separated after centrifugation, frozen immediately on dry ice, and then stored at −70 C until assayed for nitrite using the chemiluminescence methodologies (Sievers model 280 NO-analyzer) as previously described (Cosby et al., Nat Med 9, 1498-505, 2003; Gladwin et al., J Biol Chem 277, 27818-28, 2002; Yang et al., Free Radic Res 37, 1-10, 2003). The frozen red blood cell pellet was thawed, reacted in 8 mM NEM, 100 µM DTPA, and 4 mM ferricyanide, incubated for 5 minutes, and passed through a Sephadex G25 column (Yang et al., Free Radic Res 37, 1-10, 2003; Xu et al., Proc Natl Acad Sci USA 100, 11303-8, 2003). The hemoglobin fraction from the G25 column was quantified by the method of Drabkin (*J. Biol. Chem.* 112, 51-65, 1935) and reacted in 0.1 M HCl/0.5% sulfanilamide to eliminate residual nitrite. The samples were then injected into a solution of tri-iodide ($I_3^-$) in-line with a chemiluminescent nitric oxide analyzer (Sievers, Model 280 NO analyzer, Boulder, Colo.). NO gas is striped in the tri-iodide solution stoichiometrically from iron-nitrosyl-hemoglobin (Yang et al., *Free Radic Res* 37, 1-10, 2003).

Electron Paramagnetic Resonance Spectroscopy of Whole Blood.

This was carried out at 110K using a Bruker 4131VT temperature controller on an EMX 10/12 EPR spectrometer system set at 9.4 GHz, 10 mW, 5 G modulation, 0.08 s time constant, and 84 s scan time over 600 G. Each curve represents a single 84-second scan. Concentrations of iron-nitrosyl-hemoglobin were calculated by comparing the peak-to-peak heights to a standard sample.

Data Acquisition and Analysis.

Mean arterial pressure, pulmonary artery pressure, central venous pressure, heart rate, exhaled NO concentration, and core body temperature were measured continuously. Analog signals were digitized at 100 Hz and stored using an analogue-to-digital converter (PowerLab SP, ADInstruments, Colorado Springs, Colo.) and data acquisition software (Chart v 5.02 for Macintosh, ADInstruments, Colorado Springs, Colo.). Following the experiments, arterial blood pressure, central venous pressure, heart rate, and exhaled NO measurements were averaged into 60-second blocks.

Statistical analysis. Serial measurements of physiological variables were compared by two-way ANOVA with repeated measures with group and time as the factors. Significance of differences was evaluated with a Dunnett's post-test. Significant differences from the baseline period were evaluated using one-way-ANOVA with repeated measures with individual animals and time as the factors. Significance of differences was further evaluated with a Newman-Keul's post-test. The calculations were done using GraphPad Prism (GraphPad Software Inc., San Diego, Calif., USA). Statistical significance was assumed with $P<0.05$. Data are presented as mean±SEM.

Results

Pulmonary Vasodilatory Properties of Aerosolized Nitrite During Hypoxic-Induced Pulmonary Vasoconstriction In order to determine the effect of nebulized nitrite on hypoxic pulmonary hypertension, seven newborn lambs (2-10 days of age) were instrumented under general anesthesia and maintained on mechanical ventilators and morphine infusion. Following baseline stabilization, the lambs were subjected to a 30-minute period of hypoxia by lowering $FiO_2$ to 0.12. Nebulized nitrite or saline was administered for the last 20 minutes of the hypoxic period. Initiation of hypoxia (arterial $HbO_2$~55%) was associated with rapid increases in mean pulmonary artery pressure (from 21±1 to 34±2 mmHg, $P<0.01$) (FIG. 10A, 10B) and pulmonary vascular resistance (20% ($P<0.01$)), and decreased systemic vascular resistance (~20% ($P<0.01$)). Inhalation of nebulized nitrite but not saline (FIG. 10A, 10B) resulted in a selective decrease in pulmonary artery pressure by ~60% ($P<0.01$) (FIG. 10A, 10C) and reduced pulmonary artery resistance by ~70% ($P<0.05$) but had no measurable effect on mean arterial blood pressure (FIG. 10A, 10C) or systemic vascular resistance when compared to control animals. The decrease in pulmonary artery pressure with nitrite nebulization was associated with a progressive increase in exhaled NO from 3±1 to 15±4 ppb (FIG. 10A, 10C). Cardiac output, arterial oxyhemoglobin saturation, and methemoglobin levels did not change measurably after nitrite inhalation as compared to values during the preceding ten minutes of hypoxia (FIG. 10A). Arterial $Po_2$ could not change appreciably in our system as this was experimentally clamped.

Pulmonary Vasodilating Properties of Aerosolized Nitrite During Normoxic Drug-Induced Pulmonary Vasoconstriction In order to contrast the effects of nebulized nitrite on pulmonary artery pressure in the presence of normal deoxyhemoglobin with those in the presence of reduced oxygenated hemoglobin, the effects of nebulized nitrite were studied in a separate group of six lambs subjected to pulmonary hypertension under normoxic conditions. Stable normoxic ($SaO_2$~98%) pulmonary hypertension was induced by infusion of the endoperoxide analog of thromboxane (U46619). Intravenous infusion of U46619 at a rate of 2 μg/kg/min for 30 minutes was associated with rapid increases in pulmonary artery pressure from 24±1 to 51±4 mmHg ($P<0.001$) (FIG. 11). Ten minutes after the infusion began, addition of inhalation of nebulized nitrite resulted in a selective decrease in pulmonary artery pressure by 23±6% ($P<0.05$ compared to infusion baseline), but had no effect on mean arterial blood pressure or systemic vascular resistance (FIG. 11). The decrease in pulmonary artery pressure with nitrite nebulization was associated with a progressive increase in exhaled NO from 4.8±1.2 to 10.1±2.0 ppb ($P<0.05$ compared to baseline, FIG. 11). FIG. 2 shows a comparison of the effects of nitrite inhalation after 20 minutes on hypoxic versus drug-induced normoxic pulmonary vasoconstriction. The changes in mean pulmonary artery pressure and exhaled NO were significantly larger with nitrite treatment during hypoxic conditions. Overall the effects of nitrite inhalation on normoxic (thromboxane-induced) pulmonary hypertension were less than those observed with hypoxic pulmonary hypertension (FIGS. 10, 11, 12A), consistent with a model of hypoxemic and possibly acidemic potentiation of nitrite's vasoactivity.

pH and Oxygen Dependence of the Nitrite Reductase Activity of Deoxyhemoglobin

We hypothesize that the biochemical conversion of nitrite to NO requires both deoxyhemoglobin and protonation. Thus, data from both the normoxic and hypoxic experiments were used to study the influence of hemoglobin saturation and pH on NO production from nitrite. Measurements of exhaled NO gas and NO-modified hemoglobin (iron-nitrosyl-hemoglobin) were used as both dosimeters of NO production and as a measure of the direct byproducts of the nitrite reductase reaction of nitrite and hemoglobin to produce NO. FIG. 12 shows that iron-nitrosyl-hemoglobin, measured by tri-iodide based reductive chemiluminescence (FIG. 12B) and electron paramagnetic resonance (FIG. 12C), was markedly increased by nitrite inhalation during hypoxia but not with drug-induced normoxic pulmonary vasoconstriction. As shown in FIG. 12D, change in mean pulmonary artery pressure during hypoxia after inhalation of nebulized sodium nitrite was related to blood pH, with increased vasodilation associated with decreasing pH ($r=0.57$ $P=0.055$).

Comparison with Inhaled NO and Duration of Effect.

We next compared the efficacy of nitrite with the current therapeutic standard, inhaled NO gas. After initiation of hypoxia, lambs were subjected to (20 ppm) inhaled NO gas or nebulized nitrite for 20 minutes. The data in FIG. 13 show the duration and magnitude of the effect of NO gas inhalation (FIG. 13A) or nitrite nebulization (FIG. 13B, 13C) on hemodynamic and metabolic measurements during hypoxia. Although both treatments resulted in a pronounced reduction in hypoxic pulmonary hypertension, the response to inhaled NO gas was slightly more rapid and pulmonary pressure more nearly approached baseline when contrasted to the 60-70% correction in pressure elicited by nitrite. Systemically, mean arterial blood pressure and resistance was reduced to a similar extent with both treatments during hypoxia. However, with the relative chemical stability of the nitrite anion compared with NO gas, there was sustained vasodilation for more than 60 minutes (the duration of the hypoxic challenge) after discontinuation of nitrite inhalation, whereas the termination of NO gas delivery abolished the vasodilating effect in a matter of seconds (FIG. 13A, 13B). The relatively sustained effect of nitrite nebulization might be therapeutically advantageous by allowing for intermittent therapy analogous to the treatment of asthma with beta-adrenergic agonists by meter dose inhaler. The time course of nitrite inhalation-induced pulmonary vasodilation and plasma nitrite levels are shown (FIG. 13C, 13D). In this experiment which tracked biochemical changes for a longer period that in FIG. 10 methemoglobin (MetHb) concentrations increased from 2.1±0.1% during baseline to 2.8±0.2% after nitrite nebulization (P<0.05).

Discussion

A principle finding of this example is that a brief period of inhalation of nebulized sodium nitrite solution produces rapid and selective pulmonary vasodilation during hypoxic-induced pulmonary hypertension in newborn lambs. The significant reduction in pulmonary artery pressure following nitrite nebulization was sustained when hypoxia was continued for more than an hour after termination of nitrite nebulization. In none of the experiments did nitrite inhalation produce systemic hypotension, and methemoglobin elevation was minimal From a mechanistic standpoint, nitrite administration was associated with NO production, measured by exhaled NO gas and NO-modified hemoglobin, with responses in proportion to levels of hemoglobin-oxygen desaturation and decreases in blood pH. These data support the paradigm that nitrite is an NO-dependent vasodilator whose bioactivation is coupled to hemoglobin deoxygenation and protonation.

Inhaled NO gas is the current standard for the treatment of pulmonary hypertension. FIG. 13 provides a comparison of the effects of NO gas at 20 ppm with those of aerosolized nitrite. In about 5 minutes the NO gas effectively ablated about 80% of hypoxic-induced pulmonary hypertension, an effect that was short lived but which could be reproduced when it was given again 20 minutes later. Aerosolized sodium nitrite removed about 60% of hypoxic-induced pulmonary hypertension. This response was consistently observed in each of the lambs studied and it persisted throughout the one-hour period of hypoxia that was maintained after the nitrite aerosol was discontinued. The changes in pulmonary blood flow were accompanied by corresponding changes in the calculated resistance to blood flow through the lungs, indicating that changes were in the pulmonary vasculature rather than secondary to changes in cardiac output or systemic effects that might have altered perfusion pressures.

We demonstrate herein that aerosolized nitrite is an NO producing agent in the newborn lamb that can be readily administered by nebulization and appears to exhibit a wide therapeutic-to-safety margin, with limited systemic hemodynamic changes and methemoglobin production. This presents an attractive therapeutic option to inhaled NO. Nitrite is an ideal "NO producing" agent in that it 1) is a naturally occurring compound in blood, alveolar lining fluid, and tissue, and 2) has no parent-compound leaving group, such as the diazenium diolates, that requires extensive toxicological study prior to translation to human disease, and 3) it is already approved for human use in cyanide antidote kits. These advantages are to be counterbalanced against possible problems that might occur with more prolonged delivery, including alveolar nitrite accumulation, systemic vasodilation, and the development of methemoglobinemia.

In conclusion, the data presented in this example suggest that inhaled nitrite is a potent and selective vasodilator of pulmonary circulation of the newborn lamb and further support the paradigm that nitrite, and particularly salts of nitrite, such as sodium nitrite, is an NO-dependent vasodilator whose bioactivation is coupled to hemoglobin deoxygenation and protonation. In none of our studies did inhaling nitrite produce systemic hypotension or elevate methemoglobin levels.

Example 4

Use of Nitrite Infusions for the Prevention of Cerebral Artery Vasospasm after Subarachnoid Hemorrhage This example describes a method for using nitrite infusion to prevent cerebral artery vasospasm after intracranial hemorrhage.

Subarachnoid hemorrhage (SAH) due to the rupture of intracranial aneurysms affects 28,000 Americans annually. Almost 70% of patients with aneurysmal SAH develop severe spasm of the cerebral arteries on the seventh day after SAH. Despite aggressive medical therapy, neurological deficits resulting from vasospasm continue to be a major cause of morbidity and mortality. Although the etiology of cerebral vasospasm is poorly understood, there is increasing evidence that erythrocyte hemolysis in the cerebrospinal fluid and decreased availability of nitric oxide (NO), a potent vasodilator, plays a significant role. Reversal of vasospasm by NO or NO prodrugs has been documented in several animal models.

Despite half a century of research and clinical trials, delayed cerebral vasospasm (DCV) remains the single cause of permanent neurological deficits or death in at least fifteen percent of patients following otherwise successful endovascular or surgical treatment for ruptured intracranial aneurysm. Decreased bioavailability of nitric oxide (NO) has been mechanistically associated with the development of DCV. This work was carried out to determine whether infusions of nitrite, a naturally occurring anion that reacts with deoxyhemoglobin to form NO and S-nitrosothiol, might prevent DCV via reactions with perivascular hemoglobin.

Methods

An autologous arterial blood clot was placed around the right middle cerebral artery (R MCA) of 14 anesthetized Cynomolgus monkeys at day O, Sodium nitrite solution ($NaNO_2$, 135 mg/daily and 180 mg/daily, which approximates 45 mg/kg and 60 mg/kg per day) in 0.9% saline (n=6) or saline alone (n=8) was infused intravenously for 14 days in awake animals via an ambulatory MiniMed Infusion Pump, at 2 µl/minute. Cerebral arteriogram was performed before clot placement and on days 7 and 14, for assessment of DCV. Arteriographic vasospasm was defined as a 25% or greater reduction in the proximal 14 mm of the R MCA area as measured on the AP projection of the cerebral arteriogram (blinded assessment). Mean arterial blood pressure was measured and blood samples were collected daily from day 0; the cerebral spinal fluid samples were collected on day 0, 7, and 14.

Results

Figure 14:
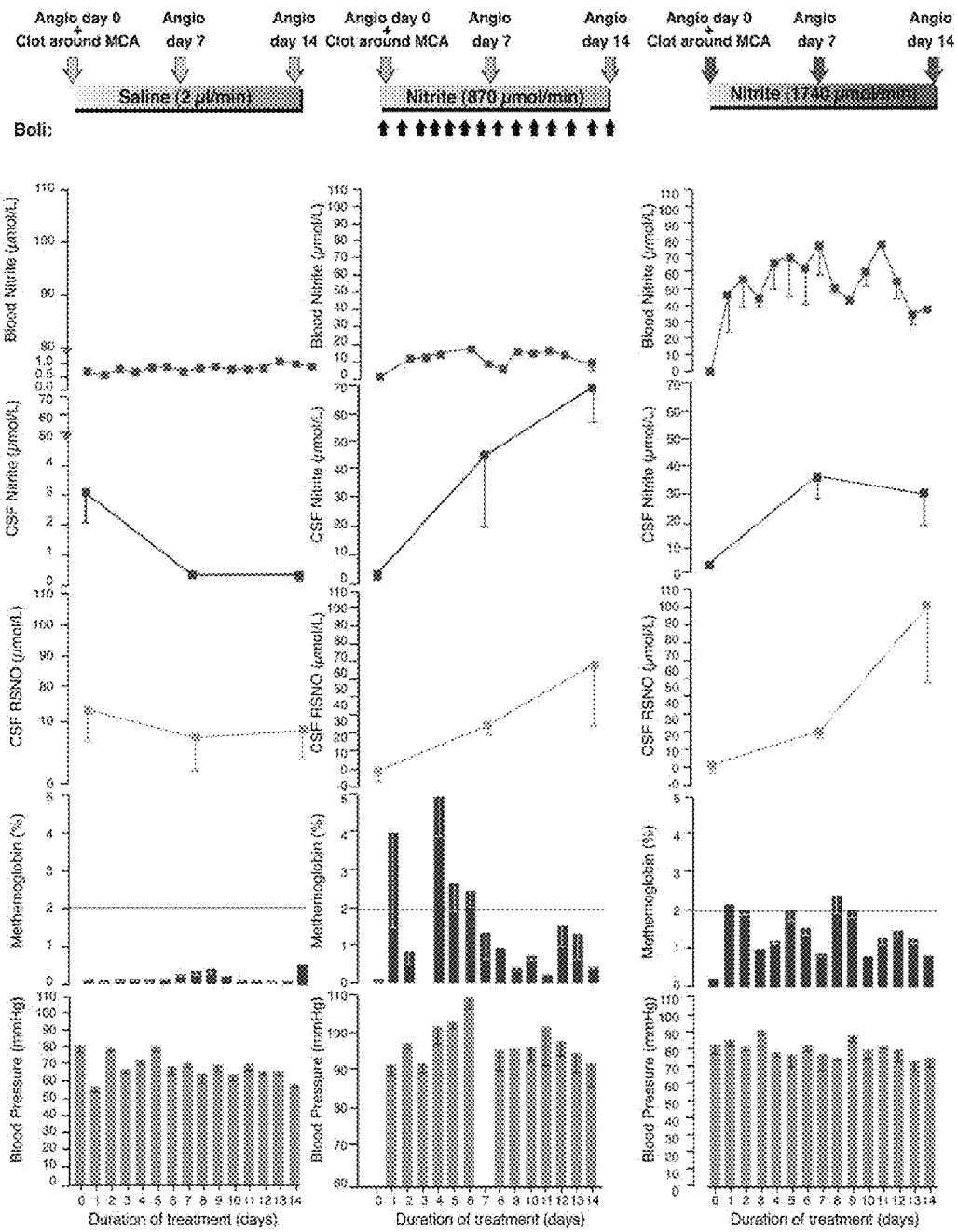
FIG. 14 is a multi-column (panel) figure depicting experiment design, biochemical and clinical results in a series of non-human primates that received intravenous nitrite to examine its effects on the development of vasospasm of the cerebral arteries and resulting ischemia. Each of the three columns represents a separate experimental group (control, low nitrite, and high nitrite). This figure describes experimental design (upper row: arrows pointing down marking the events; small arrows pointing up in the middle column representing daily boluses of nitrite), biochemical results (linear graphs: red, nitrite levels in blood; blue, nitrite levels in CSF; green, levels of nitrosylated protein/albumin in CSF; the brown bar graph represents the methemoglobin levels in blood), and mean blood pressure (the last grey bar graph) in samples collected during the experiment.
Figure 15C:
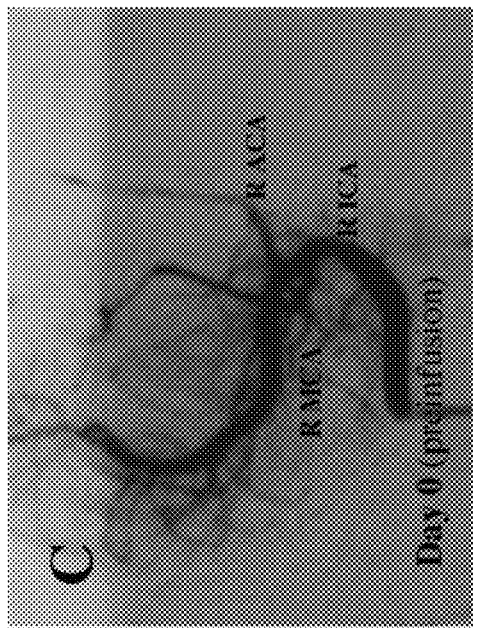
FIG. 15A, 15C) and on day 7 after SAH (FIG. 15B, 15D) in two animals: one control treated with intravenous infusion of saline at 2 µl/min for 14 days (FIG. 15A, 15B) and one treated with intravenous nitrite at 870 mmol/min for 14 days (FIG. 15C, 15D).
Figure 15D:
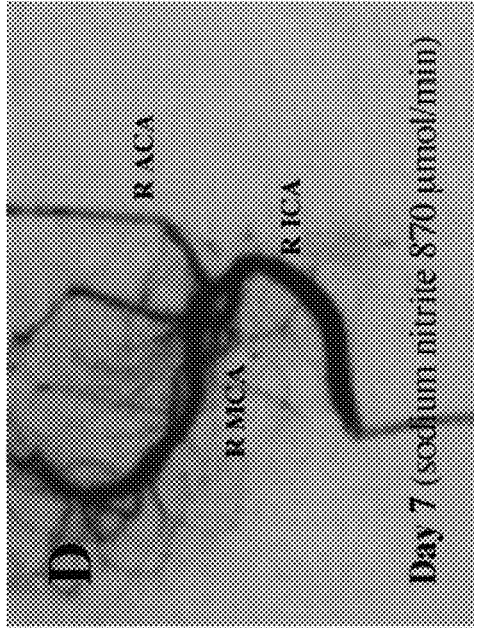
FIG. 15 presents characteristic cerebral arteriograms before SAH (Day 0 (preinfusion)
In FIG. 15B, the arrows point to the right middle cerebral artery (R MCA) in spasm. R ICA, the right internal carotid artery, R ACA, the right anterior cerebral artery.
Figure 15A:
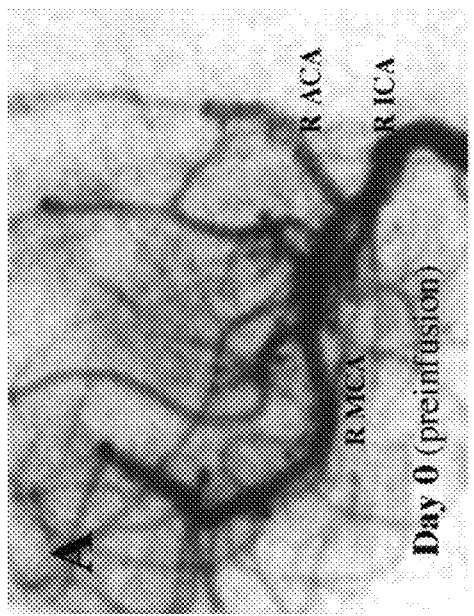
Figure 15B:
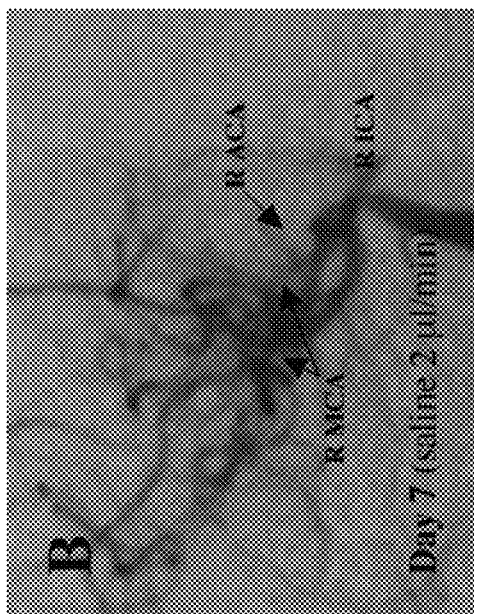

In control animals, cerebral spinal fluid nitrite levels decreased from 3.1±1.5 µM to 0.4±0.1 µM at 7 days and 0.4±0.4 µM at 14 days (FIG. 14), and all eight animals developed significant vasospasm of the R MCA (FIGS. 15 and 16), complicated by stroke and death in one animal.

Nitrite infusions were associated with increases in plasma cerebrospinal fluid nitrite and blood methemoglobin concentrations without systemic hypotension (FIG. 14), and significantly reduced the severity of vasospasm (FIGS. 15 and 16; no animals developed significant vasospasm; mean reduction in the R MCA area on day 7 after SAH was 8±9% versus 45±5%; P<0.001). Pharmacological effects of nitrite infusion were associated with bioconversion of cerebrospinal fluid nitrite to S-nitrosothiol, a potent vasodilating NO donor intermediate of nitrite bioactivation. There was no clinical or pathological evidence of nitrite toxicity.

CONCLUSIONS

Subacute sodium nitrite infusions prevent DCV in a primate model of SAH, and do so without toxicity. These data evince a novel, safe, inexpensive, and rationally designed therapy for DCV, a disease for which no current preventative therapy exists.

While in the foregoing specification this invention has been described in relation to certain preferred embodiments thereof, and many details have been set forth for purposes of illustration, it will be apparent to those skilled in the art that the invention is susceptible to additional embodiments, and that certain of the details described herein may be varied considerably without departing from the basic principles of the invention.

The invention claimed is:

1. A method for treating cerebral artery vasospasm in a subject, comprising injecting a therapeutically effective amount of non-acidified sodium nitrite to said subject whereby the non-acidified sodium nitrite contacts blood in the subject, wherein the sodium nitrite is administered to a circulating concentration of about 0.6 to 240 μM, thereby treating cerebral artery vasospasm in the subject.

2. The method of claim 1, wherein the sodium nitrite is administered by intravenous, intramuscular, intraperitoneal, intraarterial, or subcutaneous injection.

3. The method of claim 2, wherein the sodium nitrite is administered by intravenous injection.

4. The method of claim 3, wherein the sodium nitrite is administered at a rate of about 45 to 60 mg/kg per day.

5. The method of claim 1, wherein the sodium nitrite is administered in combination with at least one additional agent.

6. The method of claim 1, wherein the subject is a human.

7. The method of claim 1, wherein the non-acidified sodium nitrite is administered to the subject in an amount and for a sufficient period of time to reach a circulating concentration in blood of the subject of no more than about 25 μM, no more than about 20 μM, or no more than about 16 μM, thereby treating or ameliorating cerebral artery vasospasm in the subject.

8. The method of claim 1, wherein the sodium nitrite is administered to a circulating concentration of 10 to 60 μM.

9. A method of treating cerebral artery vasospasm in a subject, comprising injecting a therapeutically effective amount of non-acidified sodium nitrite to said subject whereby the non-acidified sodium nitrite contacts blood in the subject, wherein the sodium nitrite is administered to a circulating concentration of no more than about 100 μM, thereby treating cerebral artery vasospasm in the subject.

10. The method of claim 9, wherein the sodium nitrite is administered to a circulating concentration of no more than about 50 μM.

11. The method of claim 9, wherein the sodium nitrite is administered to a circulating concentration of no more than about 20 μM.

12. The method of claim 9, wherein the sodium nitrite is administered to a circulating concentration of no more than about 16 μM.

13. The method of claim 9, wherein the sodium nitrite is administered by intravenous, intramuscular, intraocular, intraperitoneal, intraarterial or subcutaneous injection.

14. The method of claim 13, wherein the sodium nitrite is administered by intravenous injection.

15. The method of claim 14, wherein the sodium nitrite is administered at a rate of about 45 to 60 mg/kg per day.

16. The method of claim 9, wherein the sodium nitrite is administered in combination with at least one additional agent.

17. The method of claim 9, wherein the subject is a human.

* * * * *

UNITED STATES PATENT AND TRADEMARK OFFICE
CERTIFICATE OF CORRECTION

PATENT NO. : 8,927,030 B2
APPLICATION NO. : 12/748184
DATED : January 6, 2015
INVENTOR(S) : Gladwin et al.

It is certified that error appears in the above-identified patent and that said Letters Patent is hereby corrected as shown below:

In the Claims:

Claim 2 (column 55, line 37), "intramuscular, intraperitoneal" should be –intramuscular, intraocular, intraperitoneal–

Signed and Sealed this
Twenty-second Day of March, 2016

Michelle K. Lee
*Director of the United States Patent and Trademark Office*